US011414426B2

(12) United States Patent
Fabbro et al.

(10) Patent No.: US 11,414,426 B2
(45) Date of Patent: Aug. 16, 2022

(54) TREATMENT OF SKIN DISORDERS

(71) Applicant: PIQUR THERAPEUTICS AG, Basel (CH)

(72) Inventors: Doriano Fabbro, Arlesheim (CH); Petra Hillmann-Wüllner, Zürich (CH); Anton Stütz, Altmünster (AT)

(73) Assignee: TORQUR AG, Basel (CH)

( * ) Notice: Subject to any disclaimer, the term of this patent is extended or adjusted under 35 U.S.C. 154(b) by 158 days.

(21) Appl. No.: 16/765,077

(22) PCT Filed: Nov. 22, 2018

(86) PCT No.: PCT/EP2018/082211
§ 371 (c)(1),
(2) Date: May 18, 2020

(87) PCT Pub. No.: WO2019/101853
PCT Pub. Date: May 31, 2019

(65) Prior Publication Data
US 2021/0107913 A1 Apr. 15, 2021

(30) Foreign Application Priority Data
Nov. 23, 2017 (EP) ..................... 17203386

(51) Int. Cl.
*C07D 491/08* (2006.01)
*C07D 413/14* (2006.01)
(Continued)

(52) U.S. Cl.
CPC ......... *C07D 491/08* (2013.01); *C07D 413/14* (2013.01); *C07D 417/14* (2013.01); *C07D 491/16* (2013.01)

(58) Field of Classification Search
CPC .. C07D 491/08; C07D 413/14; C07D 417/14; C07D 491/16
See application file for complete search history.

(56) References Cited

U.S. PATENT DOCUMENTS 10,640,516 B2 * 5/2020 Cmiljanovic ........ C07D 491/20
10,993,947 B2 * 5/2021 Fabbro .................... A61P 17/02
(Continued)

FOREIGN PATENT DOCUMENTS

WO  WO 2010/052569 A2  5/2010
WO  WO 2012/109423 A1  8/2012
(Continued)

OTHER PUBLICATIONS

Patani et al. Chem. Rev. 1996, 96, 3147-3176 (Year: 1996).*
(Continued)

*Primary Examiner* — Matthew P Coughlin
(74) *Attorney, Agent, or Firm* — Medler Ferro Woodhouse & Mills PLLC

(57) ABSTRACT

The present invention relates to a compound of formula (I), wherein $X^1$, $X^2$ and $X^3$ are, independently of each other, N or CH; with the proviso that at least two of $X^1 X^2$ and $X^3$ are N; Y is N or CH; W is H or F; with the proviso that when W is F, then Xi, $X^2$ and $X^3$ are N; $R^1$ and $R^2$ are independently of each other (i) a morpholinyl of formula (II) wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures wherein the arrows denote the bonds in formula (II); or (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —$CH_2$—O—$CH_2$— or —O—$CH_2CH_2$—O—; with the proviso that at least one of $R^1$ and $R^2$ is a morpholinyl of formula II; and prodrugs, metabolites, tautomers, solvates and pharmaceutically acceptable salts thereof, for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars.

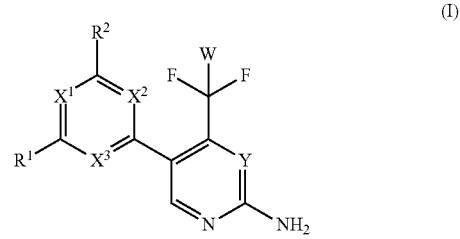

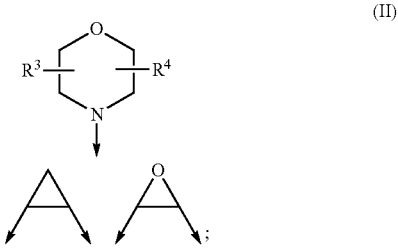

20 Claims, 5 Drawing Sheets

(51) Int. Cl.
    *C07D 417/14*   (2006.01)
    *C07D 491/16*   (2006.01)

(56) References Cited

U.S. PATENT DOCUMENTS

| | | | |
|---|---|---|---|
| 11,186,591 B2 * | 11/2021 | Cmiljanovic | ........ C07D 239/48 |
| 2011/0275762 A1 * | 11/2011 | Cmiljanovic | ............ A61P 7/02 |
| | | | 525/50 |
| 2014/0309221 A1 * | 10/2014 | Zhao | .................... C07D 401/04 |
| | | | 514/232.2 |
| 2015/0065431 A1 * | 3/2015 | Xu | ....................... A61K 31/685 |
| | | | 514/18.6 |

FOREIGN PATENT DOCUMENTS

| | | | |
|---|---|---|---|
| WO | WO 2015/181052 A1 | 12/2015 | |
| WO | WO 2016/075130 A1 | 5/2016 | |
| WO | WO-2016075130 A1 * | 5/2016 | ......... C07D 491/056 |
| WO | WO-2016187157 A1 * | 11/2016 | ................ A61P 9/00 |
| WO | WO 2017/198347 A1 | 11/2017 | |

OTHER PUBLICATIONS

Sheridan, R.P. J. Chem. Inf. Comput. Sci. 2002, 42, 103-108 (Year: 2002).*
Wang et al. Genes & Development 2013, 27, 1568-1580 (Year: 2013).*
The International Search Report issued in International Application No. PCT/EP2018/082211 dated Feb. 13, 2019.

* cited by examiner

TREATMENT OF SKIN DISORDERS

The present invention relates, in particular, to compounds for use in treatment of a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus, angiofibroma, preferably facial angiofibroma, and scars and pharmaceutical compositions thereof.

RELATED ART

Mammalian target of rapamycin (mTOR) is a large serine/threonine specific protein kinases which can combine with protein binding partners to form one of two functionally distinct mTOR complexes: mTORC1 and mTORC2 which regulate different cellular processes. mTOR can be inhibited by either inhibition of upstream kinases like PI3K and/or AKT or by directly inhibiting the mTOR kinase either allosterically (by rapamycin) or by ATP site directed inhibitors (Saxton R A, Sabatini D M (2017) *Cell* 168: 960-976).

While the rapamycin-FKBP12 complex directly inhibits mTORC1, mTORC2 is characterized by its insensitivity to acute rapamycin treatment. The immunosuppressive action of rapamycin is largely attributed to its ability to block T cell activation, a key aspect of the adaptive immune response a feature that has been exploited in the use of rapamycin derivatives in transplantation (Saxton R A, Sabatini D M (2017) *Cell* 168: 960-976). In contrast ATP site directed mTOR inhibitors (mTORKi) inhibit both mTORC1 and mTORC2 (Liu Q, et al. (2012) *Methods Mol Biol* 821: 447-460).

Recent advances in the understanding of the mTOR signaling pathway and its downstream effects in vascular proliferation have broadened the clinical applications of mTOR inhibitors in many challenging genodermatoses like tuberous sclerosis complex and pachyonychia congenita, complex vascular anomalies, and inflammatory dermatoses (A. L. Fogel et al., J Am Acad Dermatol 2015; 72:879-89 and references cited therein).

Tuberous sclerosis (TSC) is a rare autosomal dominant multi-system genodermatosis characterized by the formation of multi-systemic hamartomas. TSC is a genetic disorder (1 in 6,000 individuals) involving the TSC1 (encoding hamartin) and/or TSC2 genes (encoding tuberin) that causes benign tumors to grow in the brain and on other vital organs such as the kidneys, heart, eyes, lungs, and skin. Both mTOR and TSC1/TSC2 proteins are downstream of the PI3K/PKB pathway and the TSC1/TSC2 complex is a negative regulator of the mTOR pathway whose loss of function leads to overactivation of the mTOR pathway. Mutations in either TSC1 or TSC2 are found in 80% of patients resulting in mTOR hyperactivity leading to the formation of hamartomas throughout the body. Lesions can occur in the kidneys, brain, heart, liver, lungs and skin, which are responsible for the decreased life expectancy. Benign skin lesions occur in nearly all TSC patients and dermatological signs appear early and are typical of the disease. The first skin symptoms correspond to pigmented spots acquired or present in the first months of life which appear as innumerable pink papules that progressively enlarge and multiply over time. The lesions, which are highly visible markers of disease, may spontaneously bleed, impair vision, and cause emotional distress.

Angiofibromas (AF) are benign tumors of fibrous tissue containing numerous dilated vascular blood vessels can cause recurrent bleeding and facial disfigurement, and they are associated with high psychological morbidity for these patients. Facial angiofibromas ("adenoma sebaceum", a rash of reddish spots or bumps) appear on the nose and cheeks in a butterfly-form distribution. They consist of blood vessels and fibrous tissue. This socially embarrassing rash starts to appear during childhood and can be removed using dermabrasion or laser treatment; cutaneous hamartomas of TSC (angiofibromas and periungual fibromas) are composed of clusters of epithelial and mesenchymal cells. Periungual fibromas, also known as Koenen's tumors, these are small fleshy tumors that grow around and under the toenails or fingernails and may need to be surgically removed if they enlarge or cause bleeding. These are very rare in childhood but common by middle age. They can be induced by nail-bed trauma (Salido-Vallejo R et al., JC (2014) *Actas Dermosifiliogr.* 105:558-68).

Whereas the diagnostic of AF has significantly improved, it is not the same for the TSC treatment which remains symptomatic. Current treatment of facial AFs, include destructive approaches such as dermabrasion, surgical excision, and laser therapy which are not effective in preventing early lesion as these treatments are not permanent and skin lesions reappear a few months. Many TSC patients have numerous large AFs that tend to recur despite destructive approaches, and develop many new lesions at a rapid rate. Furthermore, it is necessary to balance aggressive therapy against the risk of significant permanent scarring. In light of all the risks and possible complications, TSC patients' recalcitrant tumors present a significant therapeutic challenge (Salido-Vallejo R et al., JC (2014) *Actas Dermosifiliogr.* 105:558-68).

In recent years, systemic allosteric mTORC1 inhibitors with the rapalogs Sirolimus and Everolimus have been used to treat the complications of TSC but their use has been limited because of side effects. Systemic rapalog therapy is associated with significant side effects, and drug holidays are often necessary (summarized in A. L. Fogel et al., J Am Acad Dermatol 2015; 72:879-89). Topical formulations have been developed to reduce adverse events and provide targeted therapy to cutaneous disease, and case reports describe the off-label use of topical rapalog formulations for a variety of dermatologic conditions (A. L. Fogel et al., J Am Acad Dermatol 2015; 72:879-89; Salido-Vallejo R et al., JC (2014) *Actas Dermosifiliogr.* 105:558-68; Balestri R, et al M (2015). *Journal of the European Academy of Dermatology and Venereology* 29: 14-20, Viswanath V, et al. (2016). *Indian Journal of Dermatology* 61: 119-119).

Birt-Hogg-Dubé syndrome (BHD) has similar clinical manifestations to TSC, but is caused by mutations in the gene that encodes folliculin, which interacts with the mTOR signaling pathway (Schaffer J V, et al (2005). *Journal of the American Academy of Dermatology* 53: S108-S111, Luijten M N, et al., Hum Mol Genet. 2013; 22:4383-4397). mTOR inhibitors have been hypothesized as a potential treatment for BHD, and a phase III clinical trial using topical sirolimus to treat the cutaneous fibro-folliculomas of BHD has recently been conducted (Steense Mv. in: U. N. I. o. Health editor. Online2013. Available at: http://clinicaltrials.gov/ct2/show/NCT00928798?term=birtlhogg1dube&rank=2). One case report describes topical sirolimus for the treatment of familial multiple discoid fibromas, an extremely rare genodermatosis with a yet unidentified genetic mutation that has recently been described as a clinical and genetic entity distinct from BHD.

PTEN hamartoma tumor syndrome which is due to the loss of function of phosphatase and tensin homolog (PTEN)

is a collection of rare clinical syndromes including Cowden disease, Bannayan-Riley-Ruvalcaba syndrome, and Lhermitte-Duclos syndrome, which are all characterized by the presence of hamartomas in multiple organs and an increased susceptibility to a variety of neoplasms and significant mucocutaneous manifestations (Pilarski R, Eng C. J Med Genet. 2004; 41:323-326). Proof-of-concept studies have shown efficacy using rapalog TOR inhibitors (allosteric mTORC1 inhibitors) therapy (Squarize C H, et al., Cancer Res. 2008; 68:7066-7072; Marsh D J, et al., Nat Clin Pract Oncol. 2008; 5:357-361). A phase II open-label trial assessing oral sirolimus in the treatment of Cowden and other PTEN hamartoma tumor syndromes has recently been completed in the United States and the publication of results are forthcoming (Rajan A. in: T. U. S. N. I. o. Health editor: http://www.clinicaltrials.gov/ct2/show/results/NCT00971789?term=pten1rapamycin&rank=1&sect=X736015 #outcome2).

Hereditary keratinopathy. The inducible keratin genes, including K6, K16, and K17, which are involved in the pathogenesis of pachyonychia congenital can be transcriptionally down-regulated by mTOR inhibitors (Hickerson R P, et al. J Dermatol Sci. 2009; 56:82-88; Chamcheu J C, et al. Arch Biochem Biophys. 2011; 508:123-137). A pilot study of systemic sirolimus treatment showed marked clinical reduction in painful plantar calluses and improvement of quality of life, although treatment was eventually discontinued because of gastrointestinal and mucocutaneous toxicities (Hickerson R P, et al. J Dermatol Sci. 2009; 56:82-88). This preliminary study represents a potential breakthrough, as this condition is refractory to statin, retinoid, and urea therapy, and no effective treatments are currently available (Hickerson R P, et al. J Dermatol Sci. 2009; 56:82-88; Peramo A, Marcelo C L. Arch Dermatol Res. 2013; 305: 163-171). A preliminary case study demonstrated notable improvement after topical sirolimus treatment was initiated. A phase Ib clinical trial using topical sirolimus is currently underway.

Vascular anomalies. Cutaneous vascular lesions have differential diagnosis and on the basis of their clinical appearance, natural history, and histopathology. Vascular malformations are divided into arterio-venous, capillary, lymphatic, venous and combined lesions (Mulliken and Glowacki, 1982). Lymphatic and other vascular malformative/overgrowth disorders are caused by somatic mutations in PIK3CA or like in venous malformations (VMs) which are composed of ectatic veins with scarce smooth muscle cell coverage lesions by activating mutations in the endothelial cell tyrosine kinase receptor TIE2. Sirolimus has recently been used in cancer treatment as an antiangiogenic agent, and is associated with reduced levels of VEGF, decreased responsiveness to VEGF signaling by vascular endothelial cells, and down-regulation of protein kinase B (AKT) signaling, resulting in decreased angiogenesis and reduced vascular permeability (Guba M et al., Nat Med. 2002; 8:128-135; Kwon Y S, et al., Invest Ophthalmol Visl Sci. 2005; 46:454-460; Perry B, et al., Arch Dermatol. 2007; 143:504-506; Phung T L, et al., Lasers Surg Med. 2008; 40:1-5).

Port-wine stains (PWS). PWS are congenital vascular malformations, and most cases have been associated with GNAQ mutations (Shirley M D, et al. N Engl J Med. 2013; 368:1971-1979). Increased signaling through S6 phosphorylation were shown in more than 70% of specimens from patients with Sturge-Weber syndrome, suggesting a possible role for TOR inhibitors in the treatment of vascular proliferation in these patients (Shirazi F, et al. Lymph Res Biol. 2007; 5:233-236). Currently, the treatment of choice for PWS is pulsed dye laser therapy with epidermal cooling, but repeated treatment during childhood is usually needed, and general anesthesia is often necessary when treatment is performed on a large body surface area. Complete clearance of PWS lesions is often difficult and rarely achieved (Nelson J S, et al. Lasers Surg Med. 1996; 19:224-229). It has been hypothesized that the failure of complete clearance is caused by regeneration and revascularization of photocoagulated blood vessels, and adjuvant systemic allosteric mTORC1 inhibitor therapy has been found to be beneficial in animal models and human case studies (Jia W, et al., Lasers Surg Med. 2010; 42:105-112; Tan W, et al. Lasers Surg Med. 2012; 44:796-804; Loewe R, et al., J Cutan Pathol. 2010; 37(Suppll):76-82). The practical use of systemic therapy is still questionable, because of considerations of risk-benefit ratio, especially in young children. To date there has been no assessment of the benefit of pulsed dye laser combined with topical sirolimus treatment, and trials in human subjects are eagerly awaited.

Infantile hemangioma (IH). IH have the potential to cause significant morbidity depending on size, anatomical location, and associated systemic manifestation. Although beta-blockers are becoming the standard of care in IH, 10% of patients have only partial or no responses to treatment, and patients presenting with IH caused by underlying PHACE (posterior fossa brain malformations, hemangiomas, arterial anomalies, cardiac abnormalities, and eye abnormalities) syndrome may be at increased risk for adverse events secondary to decreased vascular perfusion during beta-blocker therapy (Metry D, et al., Pediatr Dermatol. 2013; 30:71-89). The antiangiogenic properties of mTOR inhibitors make them potential candidates for the management of complex hemangiomas, which is supported by a case report of successful treatment using systemic sirolimus in a patient with refractory PHACE syndrome (Kaylani S, et al., Pediatr Dermatol. 2013; 30:e194-e197).

Complex vascular anomalies. The vascular proliferative disease kaposiform hemangioendothelioma can result in significant mass effect, platelet consumption, and high mortality caused by coagulopathy, particularly in young children (Blatt J, et al. Pediatr Blood Cancer. 2010; 55:1396-1398). These are believed to be associated with mutations in AKT and VEGF, which may be modifiable by PI3K/mTOR inhibitors. Alternative therapies for this condition are sought as surgical resection may often not be feasible because of excessive tissue infiltration and risk of bleeding. Several recent reports describe tumor regression and stabilization of platelet counts after systemic sirolimus therapy when patients failed to respond to other alternative therapies.

Blue rubber bleb nevus syndrome. Another vascular malformation disease, blue rubber bleb nevus syndrome, is characterized primarily by small, compressible, blue to purple nevi-like venous malformations in the skin, which may be caused by activating mutations in TIE2, a gene involved in vascular development (Nobuhara Y, et al., Surg today. 2006; 36:283-286). Given the association between TIE2 and the PI3K/mTOR pathway, PI3K/mTOR inhibitor therapy is now being investigated in these patients, with case reports showing clinical improvement (Yuksekkaya H, et al., Pediatrics. 2012; 129:e1080-e1084). Initial successes using sirolimus for the treatment of life-threatening vascular anomalies, including kaposiform hemangioendotheliomas and venous and lymphatic malformations have prompted a phase II clinical trial (Hammill A M, et al. Pediatr Blood Cancer. 2011; 57:1018-1024).

Given the unfavorable side-effect profile of systemic rapalog allosteric mTORC1 inhibitor therapy, it is conceivable that either topical therapy alone or the combination of low-dose systemic therapy and topical therapy may prove to be a beneficial alternative for many dermatologic diseases.

To date there are no approved targeted pharmacological therapies in many challenging disorders such as tuberous sclerosis complex, pachyonychia congenita, complex vascular anomalies, and inflammatory dermatoses. Recent advances in the understanding of the mTOR signaling pathway and its downstream effects in vascular proliferation have indicate clinical applications of allosteric mTORC1 inhibitors. Although the systemic treatment with rapamycin has shown some effects, its use has been limited because of concerns about systemic side effects. To mitigate the side effects of systemic allosteric mTORC1 inhibitors for dermatologic applications topical delivery of rapamycin and analogs may allow for effective long-term therapy while avoiding systemic toxicities. Thus, everolimus, an orally bioavailable variant of rapamycin (Afinitor/Certican/Votubia/Zortress) initially developed to prevent allograft rejection following solid organ transplantation and subependymal giant cell astrocytoma (SEGA) associated TSC and renal angiomyolypoma associated with TSC, has been used in off-label indications including topical treatment of facial angiofibromas as has been sirolimus itself (Haemel A K, et al. Arch Dermatol. 2010; 146:715-718; Koenig M K, et al. Drugs R D. 2012; 12:121-126). Moreover, US 2013-0225630 discloses the use of rapamycin by topical application for treating facial angiofibromas. However, topical application of rapamycin and its analogs is still considered undesirable by physicians, particularly on children face.

Thus there is a high unmet medical need for therapies and treatments of skin disorders resulting from excess of angiogenesis and/or fibrogenesis, such as angiofibromas and periungual fibromas, and thus in particular of skin disorders associated with tuberous sclerosis complex (TSC), other genodermatoses and complex vascular anomalies.

SUMMARY OF THE INVENTION

It has now surprisingly been found that the compounds of formula (I) are selective and specific inhibitors of mTOR and/or are dual inhibitors of PI3K/mTOR. Thus, beside the selectivity and specificity for inhibiting mTOR, the inventive compounds of formula (I) includes an additional mode of action allowing an advantageous pharmacological and toxicological profile. Preferred inventive compounds of formula (I) has been found to show a lower immunosuppressive potential than sirolimus. Moreover, it has been further found that the compounds of formula (I) have not only favorable skin penetration properties but, in addition, show a superior skin penetration as compared to sirolimus as evidenced by comparative in vivo skin penetration studies in identical experimental formulations. Furthermore, the chemical stability of the inventive compounds under stress conditions have been found to be significantly higher than sirolimus.

As a consequence and taking the reported beneficial effects of sirolimus and its analogs despite its unwarranted side effects into account, supports the beneficial usage of the inventive compounds of formula (I) for use in a method of treating a skin disorder in a subject.

Thus, in a first aspect, the invention provides for a compound of formula (I) for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars; and said compound of formula (I) is

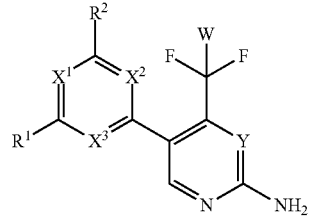

wherein
$X^1$, $X^2$ and $X^3$ are, independently of each other, N or CH; with the proviso that at least two of $X^1$, $X^2$ and $X^3$ are N;
Y is N or CH;
W is H or F; with the proviso that when W is F, then $X^1$, $X^2$ and $X^3$ are N;
$R^1$ and $R^2$ are independently of each other
 (i) a morpholinyl of formula (II)

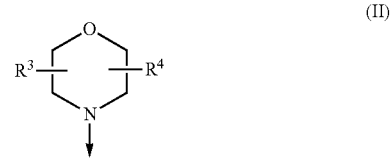

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—C$_1$-C$_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

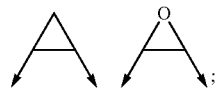

wherein the arrows denote the bonds in formula (II); or
 (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxyC$_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —CH$_2$—O—CH$_2$— or —O—CH$_2$CH$_2$—O—;
with the proviso that at least one of $R^1$ and $R^2$ is a morpholinyl of formula II;
and prodrugs, metabolites, tautomers, solvates and pharmaceutically acceptable salts thereof.

In a very preferred embodiment of the present invention, said method of treating a skin disorder in a subject is a method of topically treating a skin disorder in a subject.

In a further aspect, the present invention provides for a pharmaceutical composition for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, wherein said pharmaceutical composition comprises the inventive compounds of formula (I) together with pharmaceutically acceptable carrier, and wherein preferably said pharmaceutical composition is suitable for oral, pulmonary, rectal, colonic, parenteral, intracisternal, intravaginal, intraperitoneal, ocular, otic, local, systemic, buccal, nasal, or topical administration, and wherein further preferably said pharmaceutical composition is suitable for oral and topical administration, wherein again further preferably said pharmaceutical composition is suitable for topical administration. Thus, in a preferred embodiment, said inventive pharmaceutical composition for use is pharmaceutical composition for use in a method of topically treating a skin disorder in a subject.

In a further aspect, the invention provides for a compound of formula (I) for use in a method of treating, preferably topically treating, a disorder of skin angiogenesis and/or fibrogenesis, preferably in the treatment, preferably topical treatment of a skin disorder involving excessive angiogenesis and/or fibrogenesis.

In a further aspect, the invention provides for a compound of formula (I) for use in a method of treating, preferably topically treating, a skin disorder, wherein said skin disorder is an angiofibroma, preferably a facial angiofibroma.

In another aspect, the present invention provides for a compound of formula (I) for use in a method of treating Tuberous Sclerosis Complex (TSC).

The preferred embodiments of the compounds of formula (I) should independently apply to all aspects of the present invention and will not be repeated for each and any aspect.

DETAILED DESCRIPTION OF THE INVENTION

Figure 1:
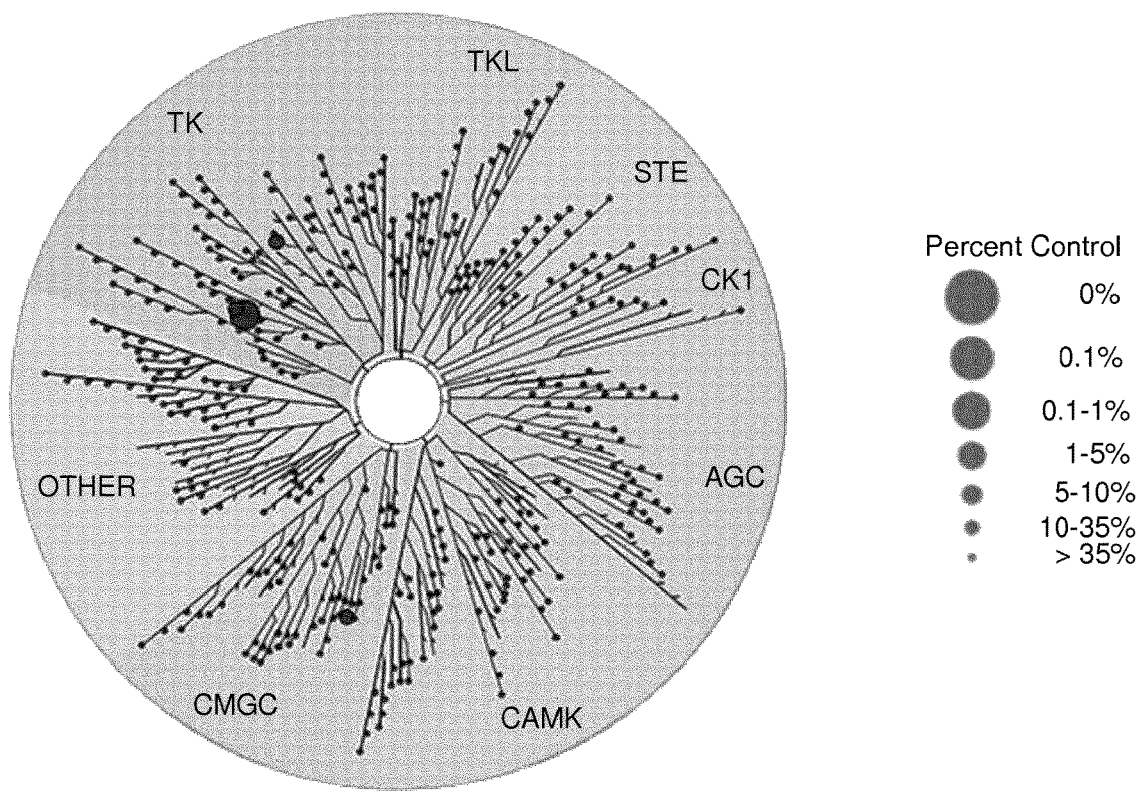
FIG. 1: Treespot of Compound 1*. The human kinome is represented as circular phylogenetetic tree with the 8 main groups of typical protein kinases and 9 groups of atypical protein kinases. The mutant variants of some protein kinases are also shown, as well as the lipid kinase panel, which is not integral part of the human kinome. The results are reported as a map (Treespot), which allows visualizing compound interactions across the human kinome and lipid kinase panel. Kinases found to bind to Compound 1* are marked with circles, where larger circles indicate higher-affinity.
Figure 1:
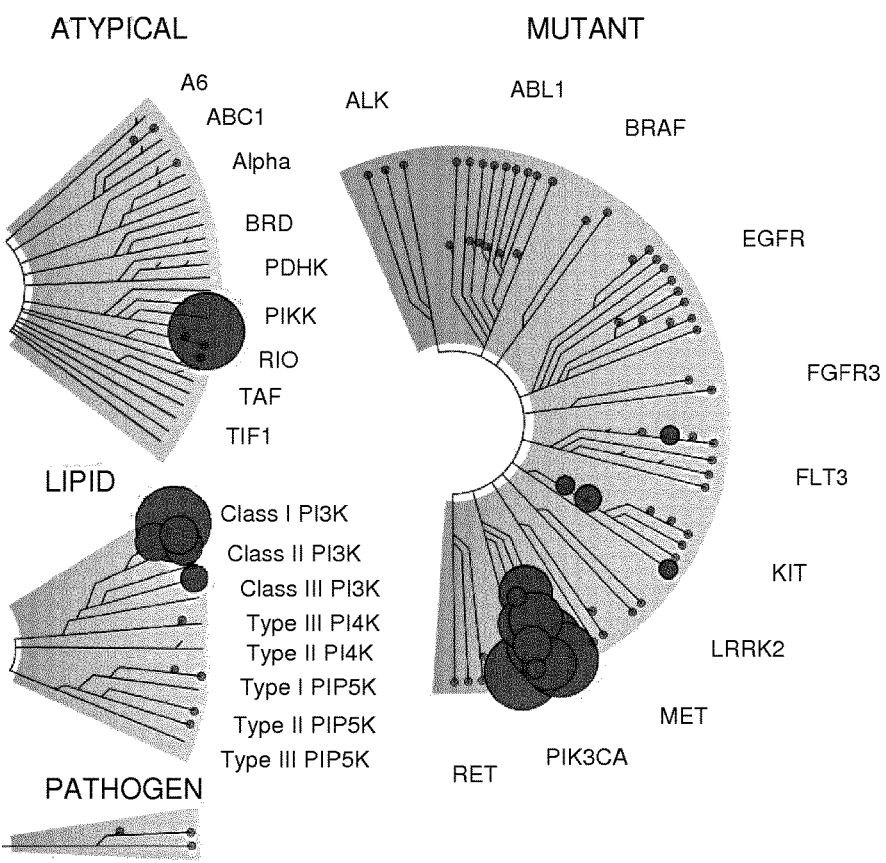

Reference will now be made in detail to the presented and further aspects and the presented and further embodiments of the invention, examples of which are illustrated in the accompanying structures and formulas. While the invention will be described in conjunction with the enumerated embodiments, it will be understood that they are not intended to limit the invention to those embodiments. One skilled in the art will recognize many methods and materials similar or equivalent to those described herein, which could be used in the practice of the present invention. The present invention is in no way limited to the methods and materials herein described.

Features, integers and characteristics, described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Unless defined otherwise, all technical and scientific terms used herein have the same meanings as commonly understood by one of ordinary skill in the art to which this invention belongs.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

The terms "comprising", "having", and "including" are to be construed as open-ended terms (i.e., meaning "including, but not limited to,") unless otherwise noted.

The terms "individual," "subject" or "patient" are used herein interchangeably. In a preferred embodiment, the subject is a human.

The phrase "pharmaceutically acceptable salt" as used herein, refers to pharmaceutically acceptable organic or inorganic salts of a compound of the invention, in particular acid addition salts. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate (mesylate), ethanesulfonate, benzenesulfonate, p-toluenesulfonate, and pamoate salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

The term "protecting group" refers to a substituent that is commonly employed to block or protect a particular functionality during the reaction of other functional groups on the compound. For example, an "amino-protecting group" is a substituent attached to an amino group that blocks or protects the amino functionality in the compound. Suitable amino-protecting groups include acetyl, trifluoroacetyl, tert-butoxycarbonyl (BOC), benzyloxycarbonyl and 9-fluorenylmethylenoxycarbonyl (Fmoc). For a general description of protecting groups and their use, see T. W. Greene, Protective Groups in Organic Synthesis, John Wiley & Sons, New York, 1991.

The terms "compound of this invention" and "compounds of the present invention" and "compounds of formula (I)" include stereoisomers, geometric isomers, tautomers, solvates, pharmaceutically acceptable salts, and solvates of the salts thereof.

The terms "treatment"/"treating" as used herein include: (1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (2) inhibiting the state, disorder or condition (e.g. arresting, reducing or delaying the development of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment. In one embodiment, the terms "treatment"/"treating" as used herein, refer to a therapeutic treatment. In another embodiment, the terms "treatment"/"treating" as used herein, refer to a prophylactic treatment.

The term "mammal" includes, but is not limited to, humans, mice, rats, guinea pigs, monkeys, dogs, cats, horses, cows, pigs, and sheep. The term "mammal", as used herein, preferably refers to humans.

As used herein, the term "systemic administration" refers to administration of a compound according to the invention, such that the compound becomes widely distributed in the body in significant amounts and has a biological effect, e.g. its desired effect, in the blood and/or reaches its desired site of action via the vascular system. Typical systemic routes of administration include administration by (1) introducing the compound directly into the vascular system or (2) oral, pulmonary, or intramuscular administration wherein the compound is adsorbed, enters the vascular system, and is carried to one or more desired site(s) of action via the blood.

The terms "oral", "orally", and "oral administration", as used herein, refer to orally ingesting a compound of the present invention.

The terms "topical administration" or "administered topically" are used in its broadest sense to include administration to a surface on the body that is generally open to the surroundings. This includes not only the skin but also the nasal and oral passages and the genitalia. Thus, topical administration can include application to the skin, application to the nasal passages, application to the oral cavity (including the upper throat), and application to the genitalia. Topical formulations have been available in a variety of forms, including creams, ointments, solutions, lotions, suspensions, pastes, emulsions, gels, sprays, foams, and the like. Water miscible creams have generally been employed for moist or weeping lesions, whereas ointments have been generally chosen for dry, lichenified or scaly lesions or where a more occlusive effect has been required. Lotions have generally been useful when minimal application to a large or hair-bearing area has been required or for the treatment of exudative lesions. Topical administration may also involve the use of transdermal administration such as transdermal patches or iontophoresis devices.

The term "parenteral" as used herein includes subcutaneous injections, intravenous, intramuscular, intrasternal injection, or infusion techniques.

The expression "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "dual PI3K/mTOR" inhibitor as used herein refers to a compound capable of inhibiting a Type I PI3K kinase and mTOR kinase activity by at least 2 µM preferably by at least 1 µM.

The term "prodrug" as used in this application refers to a precursor or derivative form of a compound of the invention that may have improved properties such as better solubility, reduced cytotoxicity or increased bioavailability compared to the parent compound or drug and is capable of being activated or converted into the more active parent form. The prodrugs of this invention include, but are not limited to, derivatives of the amino group connected to the pyridine or pyrimidine nucleus in which one or two hydrogens are replaced by a suitable substituent, or derivatives of the ring amino function if $R^2$ is piperazin-1-yl. Examples of such prodrugs are compounds acylated by an amino acid selected from the 20 most often occurring natural L-alpha-amino acids, acylated by a dipeptide such as L-Ala-L-Ala, by carbonic acid, sulfuric acid or phosphoric acid, as well as pharmaceutically acceptable salts thereof.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. In particular, compounds of formula (I) as defined hereinbefore, which are oxygenated or hydroxylated at any one position in the morpholine, piperazine or thiomorpholine ring $R^1$ and/or $R^2$ are considered metabolites. Further metabolites considered are thiomorpholine S-oxides and thiomorpholine S,S-dioxides. Accordingly, the invention is also directed to metabolites of compounds of the invention, including compounds produced by a process comprising contacting a compound of this invention with a mammal for a period of time sufficient to yield a metabolic product thereof.

In a first aspect, the invention provides a compound of formula (I)

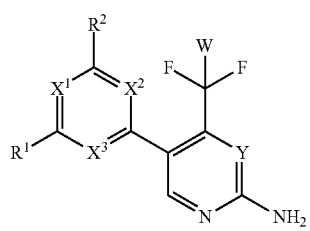

(I)

wherein
$X^1$, $X^2$ and $X^3$ are, independently of each other, N or CH; with the proviso that at least two of $X^1$, $X^2$ and $X^3$ are N;
Y is N or CH;
W is H or F; with the proviso that when W is F, then $X^1$, $X^2$ and $X^3$ are N;
$R^1$ and $R^2$ are independently of each other
  (i) a morpholinyl of formula (II)

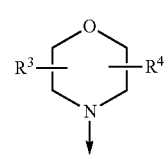

(II)

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from C1-$C_3$alkylene optionally substituted with 1 to 4 F, —$CH_2$—O—$CH_2$—, —$CH_2$—NH—$CH_2$—, or any of the structures

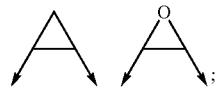

wherein the arrows denote the bonds in formula (II); or
  (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —$CH_2$—O—$CH_2$— or —O—$CH_2CH_2$—O—;
with the proviso that at least one of $R^1$ and $R^2$ is a morpholinyl of formula II;
and prodrugs, metabolites, tautomers, solvates and pharmaceutically acceptable salts thereof; for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, preferably hypertrophic scars. In a very preferred embodiment of the present invention, said method of treating a skin disorder in a subject is a method of topically treating a skin disorder in a subject. $R^3$ and $R^4$ denotes two independent substitutions and substituents, as defined herein, of said morpholinyl of formula (II) which are either both on the same carbon atom of said morpholinyl of formula (II) or on different carbon atoms of said morpholinyl of formula (II), and, hereby further, either on the same carbon-carbon bridge or on different carbon-carbon bridges linking the heteroatoms of said morpholinyl of formula (II). Typically and preferably, when $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

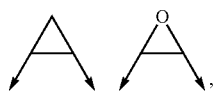

wherein the arrows denote the bonds in formula (II), then said bivalent residue —$R^5R^6$— and said bonds denoted by said arrows are linked to carbon atoms located on different carbon-carbon bridges linking the heteroatoms of said morpholinyl of formula (II).

Each alkyl moiety either alone or as part of a larger group such as alkoxy is a straight or branched chain and is preferably $C_1$-$C_3$alkyl, more preferably $C_1$-$C_2$alkyl. Examples include in particular methyl, ethyl, n-propyl and prop-2-yl (iso-propyl). Examples of an alkoxy include in particular methoxy, ethoxy, n-propoxy and iso-propoxy. As described herein, alkoxy may include further substituents such as halogen atoms leading to haloalkoxy moieties.

The term "alkoxyalkyl" refers to an R—O—R' moiety in which the R and R' groups are alkyl groups as defined herein. Examples include methoxymethyl, methoxyethyl, ethoxyethyl and methoxypropyl.

Each alkylene moiety is a straight or branched chain and is, particularly for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—, preferably —$CH_2$—, —$CH_2$—$CH_2$— or —$CH(CH_3)$—.

Each haloalkyl moiety either alone or as part of a larger group such as haloalkoxy is an alkyl group substituted by one or more of the same or different halogen atoms. Haloalkyl moieties include for example 1 to 5 halo substituents, or 1 to 3 halo substituents. Examples include in particular fluoromethyl, difluoromethyl, trifluoromethyl, chlorodifluoromethyl and 2,2,2-trifluoro-ethyl.

Each haloalkenyl moiety either alone or as part of a larger group such as haloalkenyloxy is an alkenyl group substituted by one or more of the same or different halogen atoms. Examples include 2-difluoro-vinyl and 1,2-dichloro-2-fluoro-vinyl. Haloalkenyl moieties include for example 1 to 5 halo substituents, or 1 to 3 halo substituents.

Each cycloalkyl moiety can be in mono- or bi-cyclic form, typically and preferably in mono-cyclic form, and preferably contains 3 to 6 carbon atoms. Preferred examples of monocyclic cycloalkyl groups include in particular cyclopropyl, cyclobutyl, cyclopentyl and cyclohexyl.

The term "heterocyclic ring" refers to a saturated or partially unsaturated carbocyclic ring containing one to three heteroatoms selected from nitrogen, oxygen and sulfur as ring members. Such rings do not contain adjacent oxygen atoms, adjacent sulfur atoms, or adjacent oxygen and sulfur atoms within the ring. Preferred examples include in particular tetrahydrofuranyl, pyrrolidinyl, pyrazolidinyl, imidazolidinyl, piperidinyl, piperazinyl, dioxanyl, morpholinyl, oxazolidinyl and isooxazolidinyl.

Where a group is said to be optionally substituted, preferably there are optionally 1-3 substituents, more preferably optionally 1-2 substituents.

Certain compounds of formula (I) may contain one or two or more centers of chirality and such compounds may be provided as pure enantiomers or pure diastereoisomers as well as mixtures thereof in any ratio. The compounds of the invention also include all tautomeric forms of the compounds of formula (I).

In a preferred embodiment, the present invention provides for the compound of formula (I) as defined herein and tautomers, solvates and pharmaceutically acceptable salts thereof, for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, preferably hypertrophic scars.

In another preferred embodiment, the present invention provides for the compound of formula (I) for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, preferably hypertrophic scars, wherein $X^1$, $X^2$ and $X^3$ are N.

In another preferred embodiment, (i) said $X^1$ and said $X^2$ are N, and said $X^3$ is CH; (ii) said $X^1$ and said $X^3$ are N, and said $X^2$ is CH; or (iii) said $X^2$ and said $X^3$ are N, and said $X^1$ is CH, and preferably tautomers, solvates and pharmaceutically acceptable salts thereof. In another embodiment, (i) said $X^1$ and said $X^2$ are N, and said $X^3$ is CH; or (ii) said $X^2$ and said $X^3$ are N, and said $X^1$ is CH, and preferably tautomers, solvates and pharmaceutically acceptable salts thereof. In another preferred embodiment, said $X^1$ and said $X^3$ are N, and said $X^2$ is CH; and preferably tautomers, solvates and pharmaceutically acceptable salts thereof.

In another preferred embodiment, the present invention provides for the compound of formula (I) for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, preferably hypertrophic scars, wherein W is H.

In another preferred embodiment, the present invention provides for the compound of formula (I) for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, preferably hypertrophic scars, wherein W is F.

In another preferred embodiment, said Y is N, and preferably tautomers, solvates and pharmaceutically acceptable salts thereof. In another preferred embodiment, said Y is CH, and preferably tautomers, solvates and pharmaceutically acceptable salts thereof.

In another preferred embodiment, said $R^1$ and said $R^2$ are independently of each other selected from

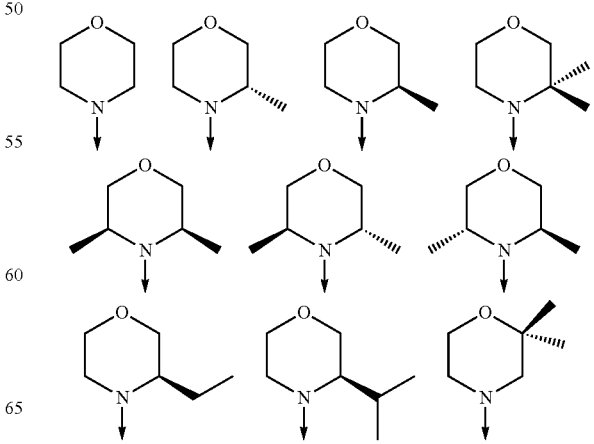

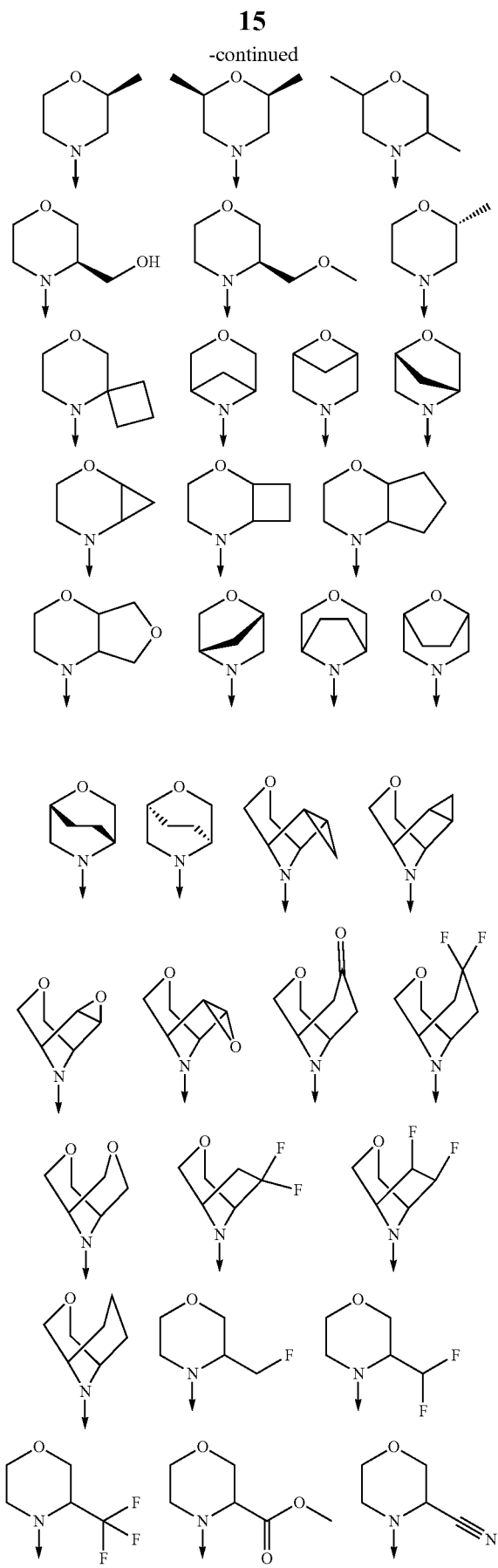
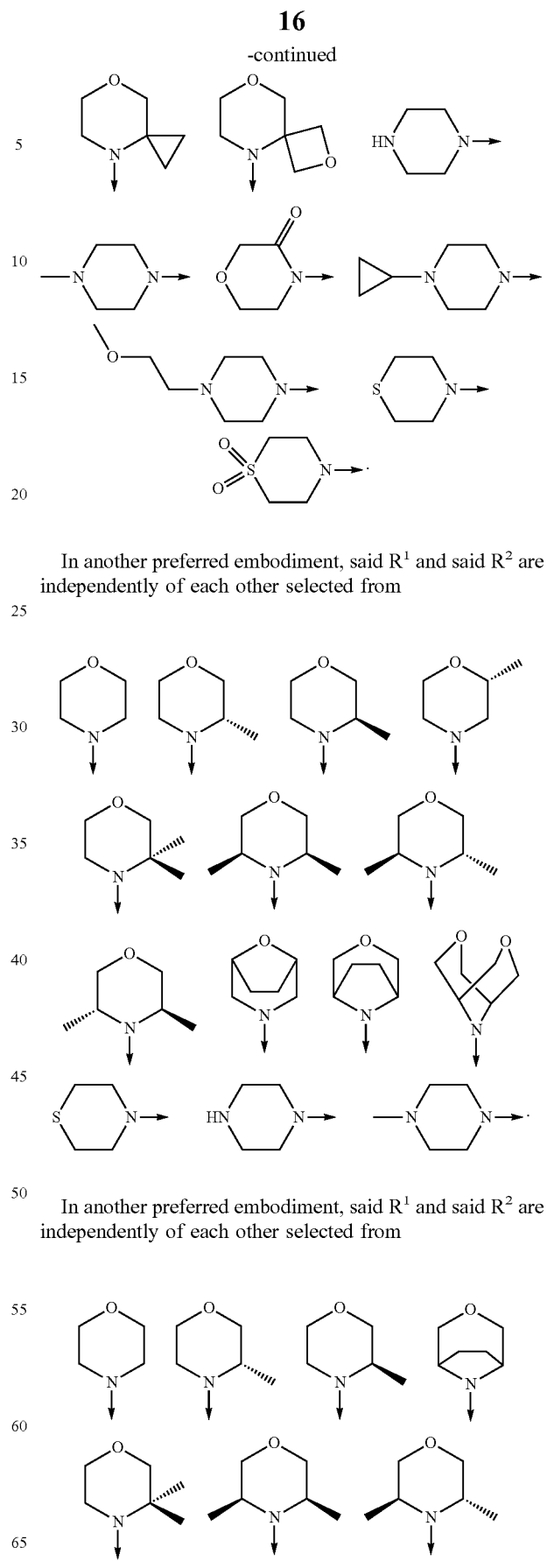
In another preferred embodiment, said $R^1$ and said $R^2$ are independently of each other selected from
In another preferred embodiment, said $R^1$ and said $R^2$ are independently of each other selected from

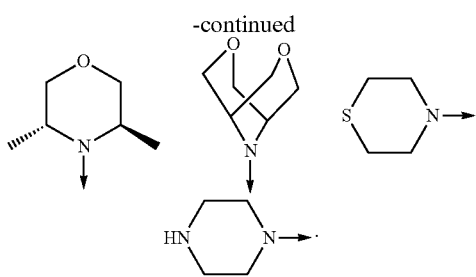

In another preferred embodiment, said R¹ and said R² are independently of each other selected from

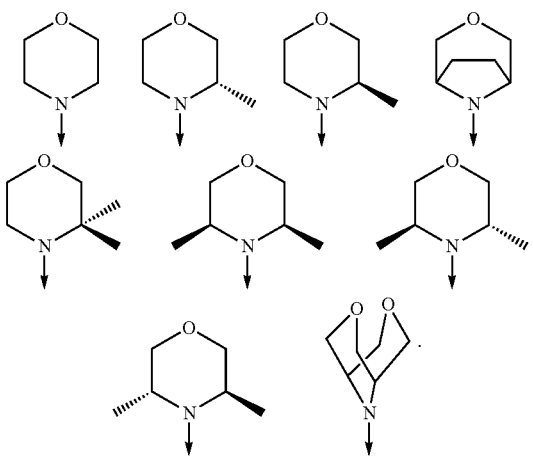

In another preferred embodiment, said compound is selected from 1, 1*, 2, 2*, 3, 4, 5, 6, 6*, 7, 7*, 8, 8*, 9, 9*, 10, 11, 12, 12*, 13, 13*, 14, 15, 16, 17, 18, 19, 20, 20*, 21, 21*, 22, 23, 24, 25, 26, 27, 28, 29, 30, 31, 32, 33, 34, 37, 38, 39, 40, 41, 42, 44, 45, 46, 47, 50, 51, 52, 53, 54, 55, 56, 66, 67, 68, 69, 70, 71, 77, 78, 79, 80, 82, 83, 84, 85, 86 and 88, and tautomers, solvates and pharmaceutically acceptable salts thereof.

In another preferred embodiment, said compound is selected from 1, 1*, 2, 2*, 3, 4, 5, 6, 6*, 7, 7*, 8, 8*, 9, 9*, 10, 11, 12, 12*, 13, 13*, 14, 15, 16, 17, 18, 19, 20, 20*, 21, 21*, 22, 23, 24, 25, 26, 27, 28, 29, 30, 31, 32, 33, 34, 37, 38, 39, 40, 41, 42, 44, 45, 46, 47, 82, 83, 84, 85, 86 and 88, and tautomers, solvates and pharmaceutically acceptable salts thereof.

In another preferred embodiment, said compound is selected from 1, 1*, 2, 2*, 3, 4, 6*, 7, 7*, 8, 8*, 9, 9*, 12*, 13, 13*, 20*, 21*, 37, 38, 39, 40, 41, 42, 43, 44, 45, 46, 47, 82, 83, 84, 85, 86 and 88; and tautomers and pharmaceutically acceptable salts thereof.

In another preferred embodiment, said compound is selected from 1, 2, 3, 4, 7, 8, 9, 13, 37, 38, 39, 40, 41, 42, 43, 44, 45, 46, 47, 82, 83, 84, 85, 86 and 88, and tautomers, solvates and pharmaceutically acceptable salts thereof.

In another preferred embodiment, said compound is selected from 1, 1*, 2, 2*, 3, 4, 6*, 7, 7*, 8, 8*, 9, 9*, 12*, 13, 13*, 20*, 21* and 44, and tautomers, solvates and pharmaceutically acceptable salts thereof.

In another preferred embodiment, said compound is selected from 1, 1*, 2, 2*, 3, 4, 6*, 7, 7*, 8, 8*, 9, 9*, 12*, 13, 13*, 20*, 21*, and tautomers, solvates and pharmaceutically acceptable salts thereof.

In another preferred embodiment, said compound is selected from 1, 2, 3, 4, 7, 8, 9, 13 and 44, and tautomers, solvates and pharmaceutically acceptable salts thereof.

In another preferred embodiment, said compound is selected from
1: 4-(difluoromethyl)-5-(4,6-dimorpholino-1,3,5-triazin-2-yl)pyridin-2-amine;
2: 4-(difluoromethyl)-5-(4,6-dimorpholino-1,3,5-triazin-2-yl)pyrimidin-2-amine;
3: 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
4: 5-(4-(3-oxa-8-azabicyclo[3.2.1]octan-8-yl)-6-morpholino-1,3,5-triazin-2-yl)-4-(difluoromethyl)pyridin-2-amine;
7: 5-(4,6-bis((S)-3-methylmorpholino)-1,3,5-triazin-2-yl)-4-(difluoromethyl)pyrimidin-2-amine;
8: (S)-4-(difluoromethyl)-5-(4-(3-methylmorpholino)-6-morpholino-1,3,5-triazin-2-yl)pyridin-2-amine;
9: (S)-4-(difluoromethyl)-5-(4-(3-methylmorpholino)-6-morpholino-1,3,5-triazin-2-yl)pyrimidin-2-amine;
13: 4-(difluoromethyl)-5-(4-morpholino-6-(piperazin-1-yl)-1,3,5-triazin-2-yl)pyrimidin-2-amine; and
44: 4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine.

In another preferred embodiment, said compound is selected from 1, 2, 3, 4, 7, 8, 9 and 13, and tautomers, solvates and pharmaceutically acceptable salts thereof.

In another preferred embodiment, said compound is selected from 1*, 2*, 6*, 7*, 8*, 9*, 12*, 13*, 20* and 21*, and tautomers, solvates and pharmaceutically acceptable salts thereof.

In another preferred embodiment, said compound is selected from 1*, 2*, 6*, 7*, 8*, 9* and 20*, and tautomers, solvates and pharmaceutically acceptable salts thereof.

In another preferred embodiment, said compound is selected from
1*: 5-(4,6-dimorpholino-1,3,5-triazin-2-yl)-4-(trifluoromethyl)pyridin-2-amine;
2*: 5-(4,6-dimorpholino-1,3,5-triazin-2-yl)-4-(trifluoromethyl)pyrimidin-2-amine;
6*: 5-[4,6-bis[(3S)-3-methylmorpholin-4-yl]-1,3,5-triazin-2-yl]-4-(trifluoromethyl)pyridin-2-amine;
7*: 5-[4,6-bis[(3S)-3-methylmorpholin-4-yl]-1,3,5-triazin-2-yl]-4-(trifluoromethyl)pyrimidin-2-amine;
8*: 5-[4-[(3S)-3-methylmorpholin-4-yl]-6-morpholino-1,3,5-triazin-2-yl]-4-(trifluoromethyl)pyridin-2-amine;
9*: 5-[4-[(3S)-3-methylmorpholin-4-yl]-6-morpholino-1,3,5-triazin-2-yl]-4-(trifluoromethyl)pyrimidin-2-amine; and
20*: 5-(4-morpholino-6-thiomorpholino-1,3,5-triazin-2-yl)-4-(trifluoromethyl)pyridin-2-amine.

In another preferred embodiment, said compound is selected from 1*, 2; 2*, 3; 6*, 7*, 8; 8*, 9*, 20* and 44, and tautomers, solvates and pharmaceutically acceptable salts thereof.

In another preferred embodiment, said compound is selected from 1*, 2; 2*, 3; 6*, 7*, 8; 8*, 9*, 12*, 13*, 20* and 21*, and tautomers, solvates and pharmaceutically acceptable salts thereof.

In another preferred embodiment, said compound is selected from 2, 3, 8 and 44, and tautomers, solvates and pharmaceutically acceptable salts thereof.

In another preferred embodiment, said compound is selected from 2, 3, and 8, and tautomers, solvates and pharmaceutically acceptable salts thereof.

In another very preferred embodiment, said compound is selected from 3, 8 and 44, and tautomers, solvates and pharmaceutically acceptable salts thereof.

In another very preferred embodiment, said compound is selected from 3 and 8; and tautomers, solvates and pharmaceutically acceptable salts thereof.

In another very preferred embodiment, said compound is selected from 3, 8, 44 and 1*; and tautomers, solvates and pharmaceutically acceptable salts thereof.

In another very preferred embodiment, said compound is selected from 3, 8, and 1*; and tautomers, solvates and pharmaceutically acceptable salts thereof.

In another very preferred embodiment, said compound is selected from 3, 44 and 1*, and tautomers, solvates and pharmaceutically acceptable salts thereof.

In another very preferred embodiment, said compound is selected from 3 and 1*, and tautomers, solvates and pharmaceutically acceptable salts thereof.

In another very preferred embodiment, said compound of formula (I) is 2.

In another very preferred embodiment, said compound of formula (I) is 2; and tautomers, solvates and pharmaceutically acceptable salts thereof.

In another very preferred embodiment, said compound of formula (I) is 3.

In another very preferred embodiment, said compound of formula (I) is 3; and tautomers, solvates and pharmaceutically acceptable salts thereof.

In another very preferred embodiment, said compound of formula (I) is 8.

In another very preferred embodiment, said compound of formula (I) is 8; and tautomers, solvates and pharmaceutically acceptable salts thereof.

In another very preferred embodiment, said compound of formula (I) is 44.

In another very preferred embodiment, said compound of formula (I) is 44; and tautomers, solvates and pharmaceutically acceptable salts thereof.

In another very preferred embodiment, said compound of formula (I) is 1*.

In another very preferred embodiment, said compound of formula (I) is 1*; and tautomers, solvates and pharmaceutically acceptable salts thereof.

In another preferred embodiment, said $R^1$ and $R^2$ are independently of each other a morpholinyl of formula (II). In one preferred embodiment, said $R^1$ is equal to $R^2$. In another preferred embodiment, said $R^1$ is not equal to $R^2$.

In another preferred embodiment, said W is H, and said $R^1$ and $R^2$ are independently of each other a morpholinyl of formula (II). In one preferred embodiment, said $R^1$ is equal to $R^2$.

In another preferred embodiment, said $R^1$ is not equal to $R^2$.

In another preferred embodiment, said W is F, said $R^1$ and $R^2$ are independently of each other a morpholinyl of formula (II). In one preferred embodiment, said $R^1$ is equal to $R^2$. In another preferred embodiment, said $R^1$ is not equal to $R^2$.

In another preferred embodiment, said $R^1$ and $R^2$ are independently of each other a morpholinyl of formula (II) and said saturated 6-membered heterocyclic ring Z.

In another preferred embodiment, said W is H, and said $R^1$ and $R^2$ are independently of each other a morpholinyl of formula (II) and said saturated 6-membered heterocyclic ring Z.

In another preferred embodiment, said W is F, and said $R^1$ and $R^2$ are independently of each other a morpholinyl of formula (II) and said saturated 6-membered heterocyclic ring Z.

In another preferred embodiment, within said morpholinyl of formula (II)

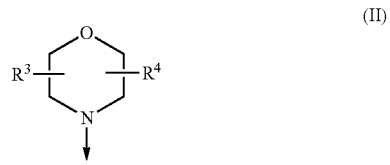

(II)

$R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

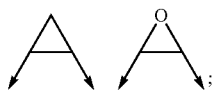

wherein the arrows denote the bonds in formula (II).

In another preferred embodiment, within said morpholinyl of formula (II)

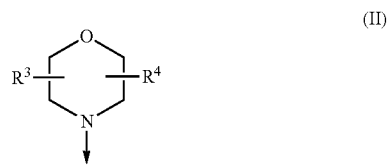

(II)

$R^3$ and $R^4$ are independently of each other H, $C_1$-$C_2$alkyl, preferably methyl, optionally substituted with one or two, preferably one, OH; $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—CH$_2$—, —CH$_2$—NH—CH$_2$—, or any of the structures

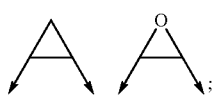

wherein the arrows denote the bonds in formula (II).

In the instance that R3 and R4 together form a bivalent residue and are bound to vicinal carbon atoms annulated morpholinyl substituents are formed. In the instance that R3 and R4 together form a bivalent residue and are spanning across the morpholine ring bridged morpholinyl substituents are formed. In the instance that R3 and R4 together form a bivalent residue and are bound to the same carbon atom of the morpholine, spiro morpholinyl substituents are formed.

In a preferred embodiment, $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

and forming a bridged morpholinyl substituent.

In another preferred embodiment, said $R^1$ and $R^2$ are independently of each other a morpholinyl of formula (II), wherein $R^3$ and $R^4$ form together a bivalent residue leading to a bridged morpholinyl, wherein $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

wherein the arrows denote the bonds in formula (II).

In a further preferred embodiment, said morpholinyl of formula (II)

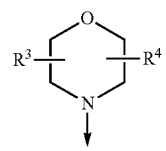

(II)

is independently of each other a morpholinyl of said formula (II), wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

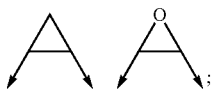

wherein the arrows denote the bonds in formula (II).

In a further preferred embodiment, said morpholinyl of formula (II)

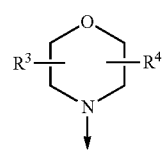

(II)

is independently of each other a morpholinyl of said formula (II), wherein $R^3$ and $R^4$ are independently of each other H, $C_1$-$C_2$alkyl, preferably methyl; $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

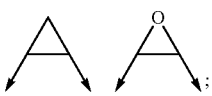

wherein the arrows denote the bonds in formula (II).

In a further preferred embodiment, said morpholinyl of formula (II) is independently of each other a morpholinyl of said formula (II), wherein $R^3$ and $R^4$ are independently of each other H or $CH_3$.

In a further preferred embodiment, said morpholinyl of formula (II) is independently of each other a morpholinyl of said formula (II), wherein $R^3$ and $R^4$ are independently of each other $C_1$-$C_2$alkyl, preferably methyl; $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

wherein the arrows denote the bonds in formula (II).

In a further preferred embodiment, said morpholinyl of formula (II) is independently of each other a morpholinyl of said formula (II), wherein $R^3$ and $R^4$ are independently of each other $C_2$-$C_3$alkyl, $CH_2OH$, $CH_2CH_2OH$, CH2F, $CHF_2$, $CF_3$, $CH_2CF_3$, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

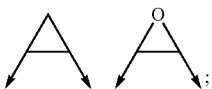

wherein the arrows denote the bonds in formula (II).

In a further preferred embodiment, said morpholinyl of formula (II) is independently of each other selected from

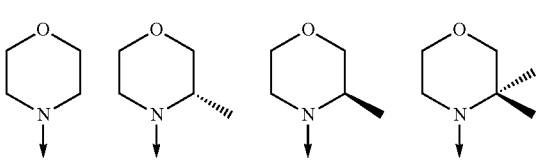

-continued

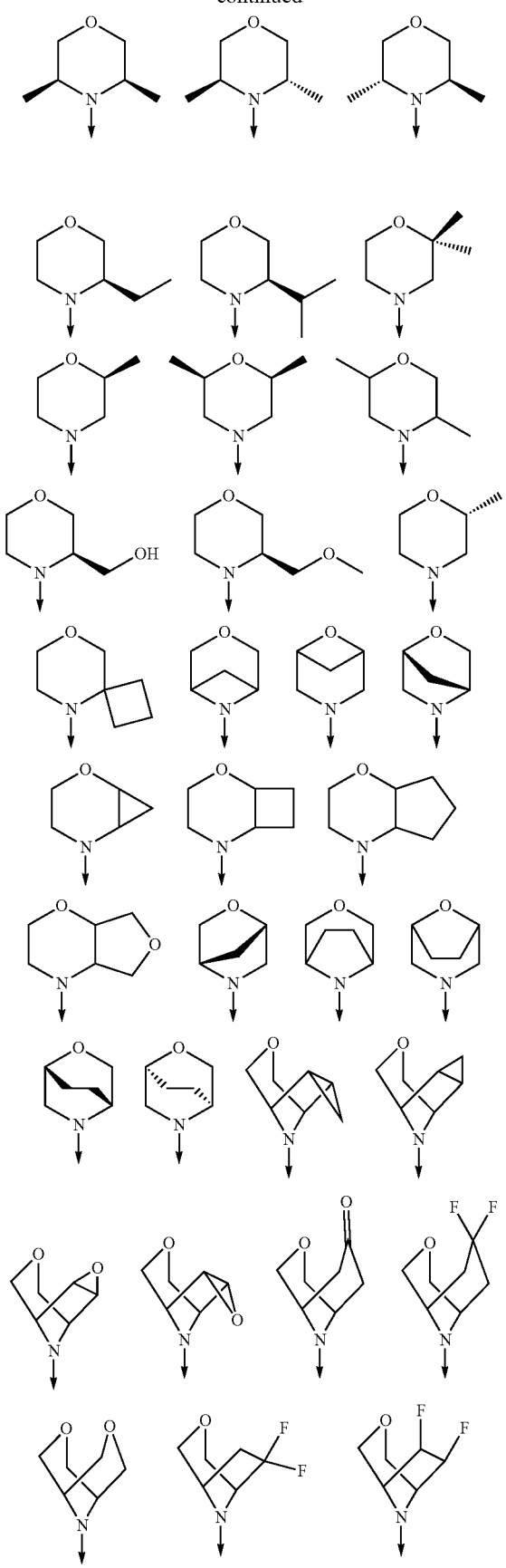

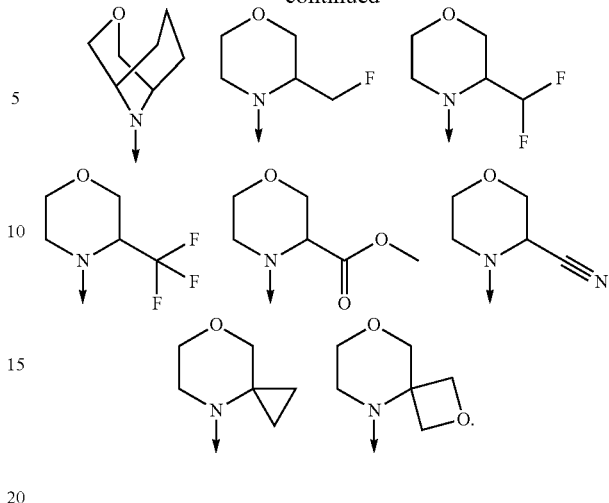

In a further preferred embodiment, said morpholinyl of formula (II) is independently of each other selected from

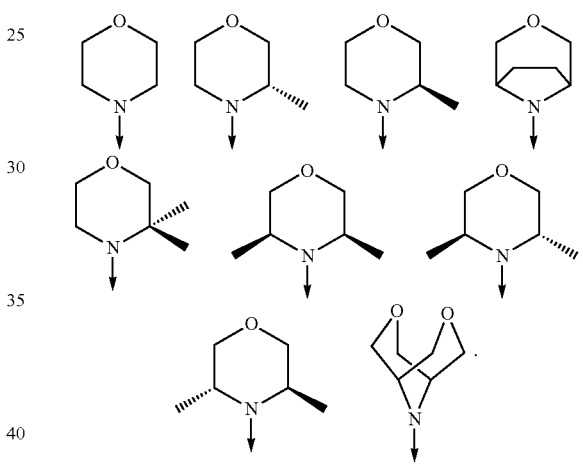

In a further preferred embodiment, said heterocyclic ring Z is a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl, $CH_2H$, $CH_2CH_2OH$, $CH_2F$, $CHF_2$, $CF_3$, $CH_2CF_3$, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —$CH_2$—O—$CH_2$— or —O—$CH_2CH_2$—O—;

In a further preferred embodiment, said heterocyclic ring Z is selected from

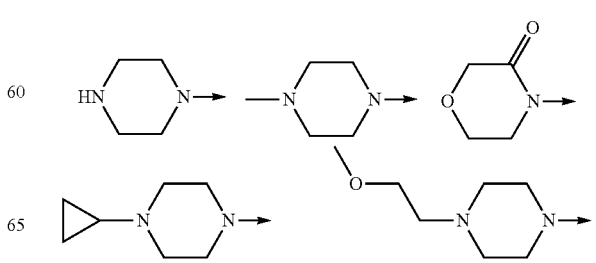

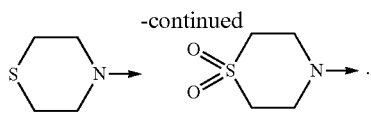

In another preferred embodiment of the present invention, said $R^1$ and said $R^2$ are independently of each other a morpholinyl of formula (II)

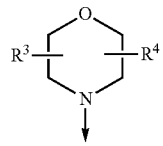

(II)

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

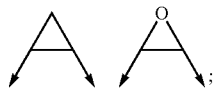

wherein the arrows denote the bonds in formula (II).
In another preferred embodiment of the present invention, said $R^1$ and said $R^2$ are independently of each other a morpholinyl of formula (II)

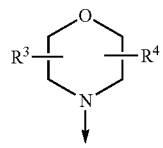

(II)

wherein the arrow denotes the bond in formula (I); and
wherein $R^3$ and $R^4$ are independently of each other H, $C_1$-$C_2$alkyl, preferably methyl, optionally substituted with one or two, preferably one, OH; $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

wherein the arrows denote the bonds in formula (II).
In a further preferred embodiment, said $R^1$ is equal to said $R^2$, and said $R^1$ and said $R^2$ are independently of each other a morpholinyl of formula (II)

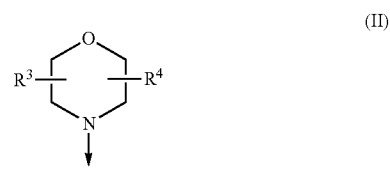

(II)

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

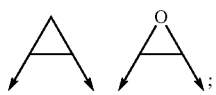

wherein the arrows denote the bonds in formula (II).
In a further preferred embodiment of the present invention, said $R^1$ and said $R^2$ are independently of each other a morpholinyl of formula (II)

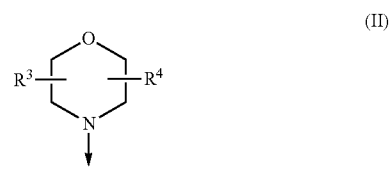

(II)

wherein the arrow denotes the bond in formula (I); and
wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

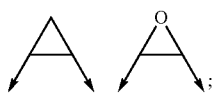

wherein the arrows denote the bonds in formula (II).
In a further preferred embodiment of the present invention, said $R^1$ and said $R^2$ are independently of each other a morpholinyl of formula (II)

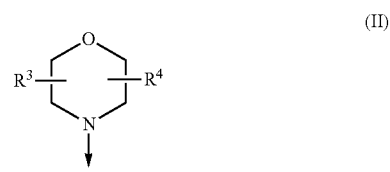

(II)

wherein the arrow denotes the bond in formula (I); and
wherein $R^3$ and $R^4$ are independently of each other H, $C_1$-$C_2$alkyl, preferably methyl; $CH_2OH$, $CH_2CH_2OH$, CH2F, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

wherein the arrows denote the bonds in formula (II).

In a further preferred embodiment of the present invention, $R^1$ is equal to $R^2$, and said $R^1$ and said $R^2$ are a morpholinyl of formula (II)

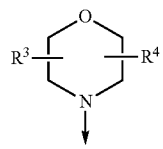

(II)

wherein the arrow denotes the bond in formula (I); and
wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

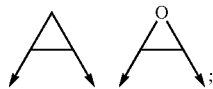

wherein the arrows denote the bonds in formula (II).

In a further preferred embodiment of the present invention, $R^1$ is equal to $R^2$, and said $R^1$ and said $R^2$ are a morpholinyl of formula (II)

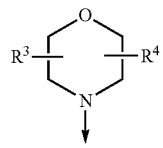

(II)

wherein the arrow denotes the bond in formula (I); and
wherein $R^3$ and $R^4$ are independently of each other H, $C_1$-$C_2$alkyl, preferably methyl; $CH_2OH$, $CH_2CH_2OH$, CH2F, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

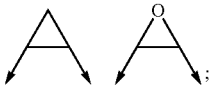

wherein the arrows denote the bonds in formula (II).

In another aspect and preferred embodiment, the present invention provides for a compound of (I) for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, preferably hypertrophic scars;

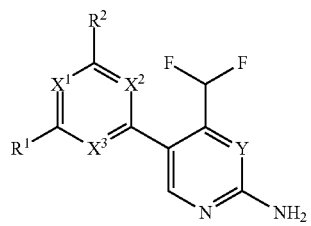

(I)

wherein
$X^1$, $X^2$ and $X^3$ are, independently of each other, N or CH; with the proviso that at least two of $X^1$, $X^2$ and $X^3$ are N; Y is N or CH; and wherein
$R^1$ and $R^2$ are independently of each other a morpholinyl of formula (II)

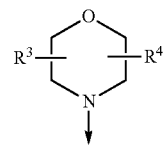

(II)

wherein the arrow denotes the bond in formula (I); and $R^1$ is not equal to $R^2$, and at least one of said $R^1$ and said $R^2$ are a morpholinyl of formula (II),

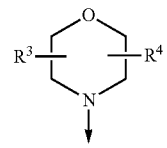

(II)

wherein $R^3$ and $R^4$ are independently of each other $C_2$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

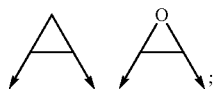

wherein the arrows denote the bonds in formula (II).

In another aspect and preferred embodiment, the present invention provides for a compound of (I) for use in a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, preferably hypertrophic scars;

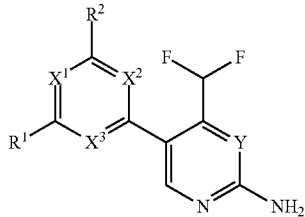

wherein
$X^1$, $X^2$ and $X^3$ are, independently of each other, N or CH; with the proviso that at least two of $X^1$, $X^2$ and $X^3$ are N; Y is N or CH; and wherein
$R^1$ and $R^2$ are independently of each other a morpholinyl of formula (II)

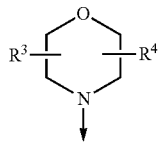

wherein the arrow denotes the bond in formula (I); and $R^1$ is not equal to $R^2$, and at least one of said $R^1$ and said $R^2$ are a morpholinyl of formula (II),

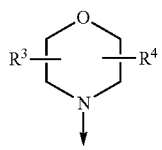

wherein $R^3$ and $R^4$ are independently of each other $C_1$-$C_2$alkyl, preferably methyl; $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

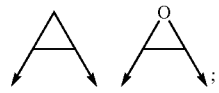

wherein the arrows denote the bonds in formula (II).
Preferably, said $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

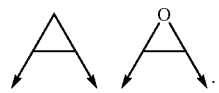

In another preferred embodiment, $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl.

In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl.

In another preferred embodiment, $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$, $X^2$ and $X^3$ are N; and tautomers, solvates and pharmaceutically acceptable salts thereof. In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$, $X^2$ and $X^3$ are N; and tautomers, solvates and pharmaceutically acceptable salts thereof. Preferably Y is N or CH; $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, or 4-thiomorpholinyl; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a further preferred embodiment, $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^3$ are N, and $X^2$ is CH; and tautomers, solvates and pharmaceutically acceptable salts thereof. In a further preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^3$ are N, and $X^2$ is CH; and tautomers, solvates and pharmaceutically acceptable salts thereof. Preferably Y is N or CH; $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-y, 4-methylpiperazin-1-yl, or 4-thiomorpholinyl; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-y, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^2$ are N, and $X^3$ is CH; and tautomers, solvates and pharmaceutically acceptable salts thereof. In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^2$ and $X^3$ are N, and $X^1$ is CH; and tautomers, solvates and pharmaceutically acceptable salts thereof. In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^2$ and $X^3$ are N, and $X^1$ is CH; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, 3,5-dimethyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, said skin disorder is a genodermatosis. In a further preferred embodiment, said genodermatosis is selected from tuberous sclerosis complex (TSC), Birt-Hogg-Dubé (BHD, phosphatase and tensin homolog (PTEN) hamartoma tumor syndrome, and hereditary keratinopathy, wherein preferably said genodermatosis is selected from a skin disorder associated with tuberous sclerosis complex (TSC), a skin disorder associated with Birt-Hogg-Dubé (BHD, phosphatase and tensin homolog (PTEN) hamartoma tumor syndrome, and hereditary keratinopathy.

In a further preferred embodiment, said genodermatosis is tuberous sclerosis complex (TSC). In a further preferred embodiment, said genodermatosis is Birt-Hogg-Dubé (BHD or also named hereditary fibroma). In a further preferred embodiment, said genodermatosis is phosphatase and tensin homolog (PTEN) hamartoma tumor syndrome (PHTS). In a further preferred embodiment, said genodermatosis is hereditary keratinopathy, In a further preferred embodiment, said genodermatosis is hereditary keratinopathy, wherein said hereditary keratinopathy is pachyonychia congenita. In a further preferred embodiment, said genodermatosis is a skin disorder associated with tuberous sclerosis complex (TSC). In a further preferred embodiment, said genodermatosis is a skin disorder associated with Birt-Hogg-Dubé (BHD).

In a further preferred embodiment, said skin disorder associated with tuberous sclerosis complex (TSC) is an angiofibroma (AF). In a very preferred embodiment, said skin disorder associated with tuberous sclerosis complex (TSC) is a facial angiofibroma. In a further preferred embodiment, said skin disorder associated with tuberous sclerosis complex (TSC) is a hamartoma. In a further preferred embodiment, said skin disorder associated with tuberous sclerosis complex (TSC) is a periungual fibroma. In another preferred embodiment, said skin disorder associated with Birt-Hogg-Dubé (BHD) are fibrofolliculomas of BHD. In a further preferred embodiment, said skin disorder is hereditary keratinopathy. In a further preferred embodiment, said skin disorder is pachyonychia congenita.

In a further preferred embodiment, said PTEN hamartoma tumor syndrome (PHTS) is selected from Cowden syndrome (CS), Bannayan-Riley-Ruvalcaba syndrome (BRRS), PTEN-related Proteus syndrome (PS), Lhermitte-Duclos syndrome and Proteus-like syndrome. In a further preferred embodiment, said PTEN hamartoma tumor syndrome (PHTS) is Cowden syndrome (CS). In a further preferred embodiment, said PTEN hamartoma tumor syndrome (PHTS) is Bannayan-Riley-Ruvalcaba syndrome (BRRS). In a further preferred embodiment, said PTEN hamartoma tumor syndrome (PHTS) is PTEN-related Proteus syndrome (PS). In a further preferred embodiment, said PTEN hamartoma tumor syndrome (PHTS) is Lhermitte-Duclos syndrome. In a further preferred embodiment, said PTEN hamartoma tumor syndrome (PHTS) is Proteus-like syndrome. In a further preferred embodiment, said hereditary keratinopathy, wherein preferably said hereditary keratinopathy is pachyonychia congenita.

In a further preferred embodiment, said skin disorder is PTEN hamartoma tumor syndrome (PHTS), wherein preferably said PTEN hamartoma tumor syndrome (PHTS) is selected from Cowden syndrome (CS), Bannayan-Riley-Ruvalcaba syndrome (BRRS), PTEN-related Proteus syndrome (PS), Lhermitte-Duclos syndrome and Proteus-like syndrome. In a further preferred embodiment, said skin disorder is Cowden syndrome (CS). In a further preferred embodiment, said skin disorder is Bannayan-Riley-Ruvalcaba syndrome (BRRS). In a further preferred embodiment, said skin disorder is PTEN-related Proteus syndrome (PS). In a further preferred embodiment, said skin disorder is Lhermitte-Duclos syndrome. In a further preferred embodiment, said skin disorder is Proteus-like syndrome. In a further preferred embodiment, said skin disorder is skin fibrosis. In a further preferred embodiment, said skin disorder is hamartoma. In a further preferred embodiment, said skin disorder is periungual fibroma.

In a further preferred embodiment, said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy.

In a further preferred embodiment, said skin disorder is a vascular anomaly, wherein said vascular anomaly is selected from port-wine stain (PWS), infantile hemangioma, blue rubber bleb nevus syndrome and a complex vascular anomaly.

In a preferred embodiment, said skin disorder is a vascular anomaly. In a further preferred embodiment, said vascular anomaly is selected from port-wine stain (PWS), infantile hemangioma, blue rubber bleb nevus syndrome and a complex vascular anomaly. In a further preferred embodiment, said vascular anomaly is port-wine stain (PWS or also named as Sturge Weber syndrome). In a further preferred embodiment, said vascular anomaly is infantile hemangioma. In a further preferred embodiment, said vascular anomaly is blue rubber bleb nevus syndrome. In a further preferred embodiment, said vascular anomaly is a complex vascular anomaly. In a further preferred embodiment, said vascular anomaly is a complex vascular anomaly, wherein said complex vascular anomaly is kaposiform hemangioendothelioma.

In a further preferred embodiment, said skin disorder is selected from port-wine stain (PWS), infantile hemangioma, blue rubber bleb nevus syndrome and a complex vascular anomaly. In a further preferred embodiment, said skin disorder is port-wine stain (PWS or also named as Sturge Weber syndrome). In a further preferred embodiment, said skin disorder is infantile hemangioma. In a further preferred embodiment, said skin disorder is blue rubber bleb nevus syndrome. In a further preferred embodiment, said skin disorder is a complex vascular anomaly. In a further preferred embodiment, said skin disorder is a complex vascular anomaly, wherein said complex vascular anomaly is kaposiform hemangioendothelioma. In a further preferred embodiment, said skin disorder is kaposiform hemangioendothelioma.

In a further preferred embodiment, said skin disorder is selected from scleroderma, sclerodermatous chronic graft-versus-host disease, lichen sclerosus, lichen planus, lichen ruber planus and scars, preferably hypertrophic scars.

In a preferred embodiment, said skin disorder is scleroderma. In a further preferred embodiment, said skin disorder is sclerodermatous chronic graft-versus-host disease. In a further preferred embodiment, said skin disorder is lichen sclerosus. In a further preferred embodiment, said skin disorder is lichen planus. In a further preferred embodiment, said skin disorder is lichen ruber planus. In a further preferred embodiment, said skin disorder is a scar.

In a further preferred embodiment, said skin disorder is a hypertrophic scar. In a further very preferred embodiment, said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars.

In a very preferred embodiment, said skin disorder is an angiofibroma (AF). In a further very preferred embodiment, said skin disorder is a facial angiofibroma.

In a very preferred embodiment, said compound of formula (I) for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein said compound of formula (I) is administered topically to the subject.

In a further preferred embodiment, said inventive compound of formula (I) for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein said compound of formula (I) is administered topically to the subject.

In a further preferred embodiment, said inventive compound of formula (I) for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein said compound of formula (I) is administered topically to the subject.

In a further preferred embodiment, said inventive compound of formula (I) for use in a method of treating a skin disorder in a subject, wherein said skin disorder is an angiofibroma (AF), preferably a facial angiofibroma, wherein said compound of formula (I) is administered topically to the subject.

In a further preferred embodiment, said inventive compound of formula (I) for use in a method of treating a skin disorder in a subject, wherein said compound of formula (I) is administered systemically, preferably orally to the subject.

In a very preferred embodiment, said compound of formula (I) for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein said compound of formula (I) is administered systemically, preferably orally to the subject.

In a further preferred embodiment, said inventive compound of formula (I) for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein said compound of formula (I) is administered systemically, preferably orally to the subject.

In a further preferred embodiment, said inventive compound of formula (I) for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein said compound of formula (I) is administered systemically, preferably orally to the subject.

In a further preferred embodiment, said inventive compound of formula (I) for use in a method of treating a skin disorder in a subject, wherein said skin disorder is an angiofibroma (AF), preferably a facial angiofibroma, wherein said compound of formula (I) is administered systemically, preferably orally to the subject.

In a preferred embodiment, said compound of formula (I) is selected from 2, 3, 8, 1* and 44; and tautomers, solvates and pharmaceutically acceptable salts thereof, or alternatively, said compound of formula (I) is selected from 2, 3, 8 and 1*; and tautomers, solvates and pharmaceutically acceptable salts thereof; for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein preferably said compound of formula (I) is administered topically to the subject.

In a preferred embodiment, said compound of formula (I) is selected from 2, 3, 8, and 44; and tautomers, solvates and pharmaceutically acceptable salts thereof, or alternatively, said compound of formula (I) is selected from 2, 3, and 8; and tautomers, solvates and pharmaceutically acceptable salts thereof, for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein preferably said compound of formula (I) is administered topically to the subject.

In a further preferred embodiment, said compound is 1* and tautomers, solvates and pharmaceutically acceptable salts thereof, for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein preferably said compound of formula (I) is administered topically to the subject.

In a further preferred embodiment, said compound is 44 and tautomers, solvates and pharmaceutically acceptable salts thereof, for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein preferably said compound of formula (I) is administered topically to the subject.

In a further preferred embodiment, said compound of formula (I) is selected from 2, 3, 8, 1* and 44; and tautomers, solvates and pharmaceutically acceptable salts thereof, or alternatively, said compound of formula (I) is selected from: 2, 3, 8 and 1*; and tautomers, solvates and pharmaceutically acceptable salts thereof, for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein preferably said compound of formula (I) is administered topically to the subject.

In a further preferred embodiment, said compound of formula (I) is selected from 2, 3, 8, and 44; and tautomers, solvates and pharmaceutically acceptable salts thereof, or alternatively, said compound of formula (I) is selected from 2, 3 and 8; and tautomers, solvates and pharmaceutically acceptable salts thereof, for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein preferably said compound of formula (I) is administered topically to the subject.

In a further preferred embodiment, said compound of formula (I) is 1* and tautomers, solvates and pharmaceutically acceptable salts thereof, for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein preferably said compound of formula (I) is administered topically to the subject.

In a further preferred embodiment, said compound of formula (I) is 44 and tautomers, solvates and pharmaceutically acceptable salts thereof, for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein preferably said compound of formula (I) is administered topically to the subject.

In a preferred embodiment, said compound of formula (I) is selected from 2, 3, 8, 1* and 44; and tautomers, solvates and pharmaceutically acceptable salts thereof, or alternatively, said compound of formula (I) is selected from 2, 3, 8 and 1*; and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, said compound of formula (I) is selected from 2, 3, 8, and 44; and tautomers, solvates and pharmaceutically acceptable salts thereof, or alternatively, said compound of formula (I) is selected from 2, 3 and 8; and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a further preferred embodiment, said compound of formula (I) is 1* and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a further preferred embodiment, said compound of formula (I) is 44 and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, said compound of formula (I) is selected from 2, 3, 8, 1* and 44; and tautomers, solvates and pharmaceutically acceptable salts thereof, or alternatively, said compound of formula (I) is selected from 2, 3, 8 and 1*; and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a preferred embodiment, said compound of formula (I) is selected from 2, 3, 8, and 44; and tautomers, solvates and pharmaceutically acceptable salts thereof, or alternatively, said compound of formula (I) is selected from 2, 3 and 8; and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a further preferred embodiment, said compound of formula (I) is 1* and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a further preferred embodiment, said compound of formula (I) is 44 and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a further very preferred embodiment, said compound of formula (I) is 1* and tautomers, solvates and pharmaceutically acceptable salts thereof, for use in a method of treating a skin disorder in a subject, wherein said skin disorder is an angiofibroma (AF), preferably a facial angiofibroma, wherein said compound of formula (I) is administered topically to the subject.

In a further very preferred embodiment, said compound of formula (I) is 44 and tautomers, solvates and pharmaceutically acceptable salts thereof, for use in a method of treating a skin disorder in a subject, wherein said skin disorder is an angiofibroma (AF), preferably a facial angiofibroma, wherein said compound of formula (I) is administered topically to the subject.

In a further very preferred embodiment, said compound of formula (I) is 1* and tautomers, solvates and pharmaceutically acceptable salts thereof, for use in a method of treating a skin disorder in a subject, wherein said skin disorder is facial angiofibroma, wherein said compound of formula (I) is administered topically to the subject.

In a further very preferred embodiment, said compound of formula (I) is 44 and tautomers, solvates and pharmaceuti-cally acceptable salts thereof, for use in a method of treating a skin disorder in a subject, wherein said skin disorder is facial angiofibroma, wherein said compound of formula (I) is administered topically to the subject.

In a further very preferred embodiment, said compound of formula (I) is 1* for use in a method of treating a skin disorder in a subject, wherein said skin disorder is an angiofibroma (AF), preferably a facial angiofibroma, wherein said compound of formula (I) is administered topically to the subject.

In a further very preferred embodiment, said compound of formula (I) is 44* for use in a method of treating a skin disorder in a subject, wherein said skin disorder is an angiofibroma (AF), preferably a facial angiofibroma, wherein said compound of formula (I) is administered topically to the subject.

In a further very preferred embodiment, said compound of formula (I) is 1* for use in a method of treating a skin disorder in a subject, wherein said skin disorder is facial angiofibroma, wherein said compound of formula (I) is administered topically to the subject.

In a further very preferred embodiment, said compound of formula (I) is 44 for use in a method of treating a skin disorder in a subject, wherein said skin disorder is facial angiofibroma, wherein said compound of formula (I) is administered topically to the subject.

In a preferred embodiment, said compound of formula (I) is 3; and tautomers, solvates and pharmaceutically acceptable salts thereof, for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein said compound of formula (I) is administered topically to the subject.

In a preferred embodiment, said compound of formula (I) is 8; and tautomers, solvates and pharmaceutically acceptable salts thereof, for use in a method of treating a skin disorder in a subject, wherein said skin disorder is a genodermatosis, wherein said genodermatosis is selected from tuberous sclerosis complex (TSC), Birt-Hogg-Dubé (BHD, phosphatase and tensin homolog (PTEN) hamartoma tumor syndrome (PHTS), and hereditary keratinopathy, wherein said compound of formula (I) is administered topically to the subject.

In a further preferred embodiment, said compound of formula (I) is 3; and tautomers, solvates and pharmaceutically acceptable salts thereof, for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein said compound of formula (I) is administered topically to the subject.

In a further preferred embodiment, said compound of formula (I) is 8; and tautomers, solvates and pharmaceutically acceptable salts thereof, for use in a method of treating a skin disorder in a subject, wherein said skin disorder is a vascular anomaly, wherein said vascular anomaly is selected from port-wine stain (PWS), infantile hemangioma, blue rubber bleb nevus syndrome and a complex vascular anomaly, and wherein said compound of formula (I) is administered topically to the subject.

In a preferred embodiment, said compound of formula (I) is 3; and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein said compound of formula (I) is administered topically to the subject.

In a preferred embodiment, said compound of formula (I) is 8; and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein said compound of formula (I) is administered topically to the subject.

In a preferred embodiment, said compound of formula (I) is 3; and tautomers, solvates and pharmaceutically acceptable salts thereof, for use in a method of treating a skin disorder in a subject, wherein said skin disorder is an angiofibroma (AF), preferably a facial angiofibroma, wherein said compound of formula (I) is administered topically to the subject.

In a preferred embodiment, said compound of formula (I) is 8; and tautomers, solvates and pharmaceutically acceptable salts thereof, for use in a method of treating a skin disorder in a subject, wherein said skin disorder is an angiofibroma (AF), preferably a facial angiofibroma, wherein said compound of formula (I) is administered topically to the subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, there is provided a compound of formula (I) according to the invention, wherein said $R^1$ and $R^2$ are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, there is provided a compound of formula (I) according to the invention, wherein W is H, and wherein R1 and R2 are independently of each other a morpholinyl of formula (II); and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, there is provided a compound of formula (I) according to the invention, wherein W is H, and wherein said $R^1$ and $R^2$ are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, there is provided a compound of formula (I) according to the invention, wherein W is F, and wherein R1 and R2 are independently of each other a morpholinyl of formula (II); and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, there is provided a compound of formula (I) according to the invention, wherein W is F, and wherein said $R^1$ and $R^2$ are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is selected from a skin disorder associated with tuberous sclerosis complex (TSC) or Birt-Hogg-Dubé (BHD, an angiofibroma (AF), preferably a facial angiofibroma, fibrofolliculoma of BHD, phosphatase and tensin homolog (PTEN) hamartoma tumor syndrome (PHTS), Cowden syndrome (CS), Bannayan-Riley-Ruvalcaba syndrome (BRRS), PTEN-related Proteus syndrome (PS), Lhermitte-Duclos syndrome, Proteus-like syndrome, hereditary keratinopathy, pachyonychia congenita, vascular anomaly, skin fibrosis, hamartoma, periungual fibroma, a vascular anomaly, port-wine stain (PWS), infantile hemangioma, blue rubber bleb nevus syndrome, a complex vascular anomaly, kaposiform hemangioendothelioma, scleroderma, sclerodermatous chronic graft-versus-host disease, lichen sclerosus, lichen planus, lichen ruber planus and scars, preferably hypertrophic scars, wherein preferably said compound of formula (I) is administered topically to the subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in a method of treating a skin disorder in a subject, wherein said skin disorder is an angiofibroma (AF), preferably a facial angiofibroma, wherein said compound of formula (I) is administered topically to the subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in a method of treating a skin disorder in a subject, wherein said skin disorder is facial angiofibroma, wherein said compound of formula (I) is administered topically to the subject.

In a preferred embodiment, there is provided a compound of formula (I) according to the invention, wherein said $R^1$ and $R^2$ are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a preferred embodiment, there is provided a compound of formula (I) according to the invention, wherein W is H, and wherein R1 and R2 are independently of each other a morpholinyl of formula (II); and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a preferred embodiment, there is provided a compound of formula (I) according to the invention, wherein W is H, and wherein said $R^1$ and $R^2$ are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a preferred embodiment, there is provided a compound of formula (I) according to the invention, wherein W is F, and wherein R1 and R2 are independently of each other a morpholinyl of formula (II); and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a preferred embodiment, there is provided a compound of formula (I) according to the invention, wherein W is F, and wherein said $R^1$ and $R^2$ are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is an angiofibroma (AF), preferably a facial angiofibroma, wherein preferably said compound of formula (I) is administered topically to the subject.

In a preferred embodiment, there is provided a compound of formula (I) according to the invention, wherein said $R^1$ and R² are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is facial angiofibroma, wherein said compound of formula (I) is administered topically to the subject.

In a preferred embodiment, there is provided a compound of formula (I) according to the invention, wherein W is H, and wherein R1 and R2 are independently of each other a morpholinyl of formula (II); and tautomers, solvates and pharmaceutically acceptable salts thereof, for use in a method of treating a skin disorder in a subject, wherein said skin disorder is facial angiofibroma, wherein said compound of formula (I) is administered topically to the subject.

In a preferred embodiment, there is provided a compound of formula (I) according to the invention, wherein W is H, and wherein said R¹ and R² are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is facial angiofibroma, wherein said compound of formula (I) is administered topically to the subject.

In a preferred embodiment, there is provided a compound of formula (I) according to the invention, wherein W is F, and wherein R1 and R2 are independently of each other a morpholinyl of formula (II); and tautomers, solvates and pharmaceutically acceptable salts thereof, for use in a method of treating a skin disorder in a subject, wherein said skin disorder is facial angiofibroma, wherein said compound of formula (I) is administered topically to the subject.

In a preferred embodiment, there is provided a compound of formula (I) according to the invention, wherein W is F, and wherein said R¹ and R² are independently of each other a morpholinyl of formula (II) and said saturated 6-membered heterocyclic ring Z; and tautomers, solvates and pharmaceutically acceptable salts thereof, for use in a method of treating a skin disorder in a subject, wherein said skin disorder is facial angiofibroma, wherein said compound of formula (I) is administered topically to the subject.

In a preferred embodiment, there is provided a compound of formula (I) according to the invention, wherein R1 is equal to R2; and tautomers, solvates and pharmaceutically acceptable salts thereof.

In a preferred embodiment, there is provided a compound of formula (I) according to the invention, wherein R1 is not equal to R2; and tautomers, solvates and pharmaceutically acceptable salts thereof.

In a further aspect, the invention provides for a method of treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars, comprising administering an effective amount of said compound of formula (I) to said subject. In a very preferred embodiment, said skin disorder is an angiofibroma (AF), preferably a facial angiofibroma, wherein preferably said effective amount of said compound of formula (I) is administered topically to the subject.

In a particularly preferred embodiment, there is provided a method of treating a skin disorder in a subject, comprising administering an effective amount of a compound of formula (I) according to the invention to said subject, wherein said compound of formula (I) is selected from 2, 3, 8, 44 and 1*, preferably 1* or 44; and tautomers, solvates and pharmaceutically acceptable salts thereof, or alternatively, said compound is selected from 2, 3, 8 and 1*, preferably 1*; and tautomers, solvates and pharmaceutically acceptable salts thereof; and wherein said skin disorder is an angiofibroma (AF), preferably a facial angiofibroma, wherein preferably said effective amount of said compound of formula (I) is administered topically to the subject.

In a particularly preferred embodiment, there is provided a method of treating a skin disorder in a subject, comprising administering an effective amount of a compound of formula (I) according to the invention to said subject, wherein said compound of formula (I) is 1*; and tautomers, solvates and pharmaceutically acceptable salts thereof; and wherein said skin disorder is an angiofibroma (AF), preferably a facial angiofibroma, wherein preferably said effective amount of said compound of formula (I) is administered topically to the subject.

In a particularly preferred embodiment, there is provided a method of treating a skin disorder in a subject, comprising administering an effective amount of a compound of formula (I) according to the invention to said subject, wherein said compound of formula (I) is 44; and tautomers, solvates and pharmaceutically acceptable salts thereof; and wherein said skin disorder is an angiofibroma (AF), preferably a facial angiofibroma, wherein preferably said effective amount of said compound of formula (I) is administered topically to the subject.

In yet a further aspect, the invention provides for the use of a compound of formula (I) for the manufacture of a medicament for treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars. In a particularly preferred embodiment, said compound is selected from 2, 3, 8, 44 and 1*, preferably 1* or 44; and tautomers, solvates and pharmaceutically acceptable salts thereof, or alternatively, is selected from 2, 3, 8 and 1*, preferably 1*; and tautomers, solvates and pharmaceutically acceptable salts thereof; and wherein said skin disorder is an angiofibroma (AF), preferably a facial angiofibroma, wherein preferably said effective amount of said compound of formula (I) is administered topically to the subject.

In yet a further aspect, the invention provides for the use of a compound of formula (I) for the manufacture of a medicament for treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars. In a particularly preferred embodiment, said compound is 1*, and tautomers, solvates and pharmaceutically acceptable salts thereof; and wherein said skin disorder is an angiofibroma (AF), preferably a facial angiofibroma, wherein preferably said effective amount of said compound of formula (I) is administered topically to the subject.

In yet a further aspect, the invention provides for the use of a compound of formula (I) for the manufacture of a medicament for treating a skin disorder in a subject, wherein said skin disorder is a genodermatosis, a vascular anomaly or a skin disorder selected from scleroderma, sclerodermatous chronic graft-versus-host disease, lichen sclerosus, lichen planus, lichen ruber planus and scars. In a particularly preferred embodiment, said compound is 44, and tautomers, solvates and pharmaceutically acceptable salts thereof; and wherein said skin disorder is an angiofibroma (AF), preferably a facial angiofibroma, wherein preferably said effective amount of said compound of formula (I) is administered topically to the subject.

Most preferred for the present invention are the following compounds shown by formula: (The names of the corresponding structures were produced using ChemDraw Ultra, version 13.0.1 as well as lower and upper software versions thereof, CambridgeSoft Corp., Cambridge Mass.).

| Compound | | |
|---|---|---|
| 1 | 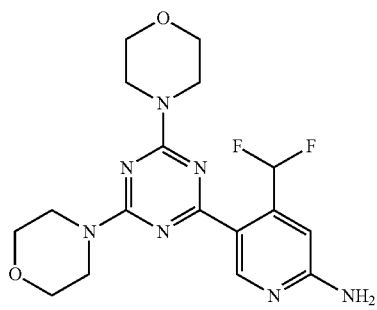 | 4-(difluoromethyl)-5-(4,6-dimorpholino-1,3,5-triazin-2-yl)pyridin-2-amine |
| 1* | 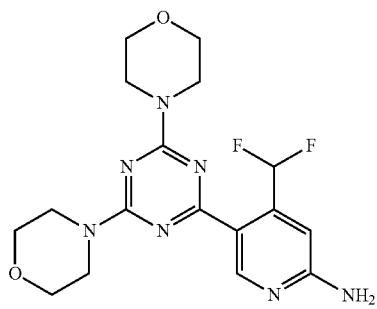 [SMILES: Nc1cc(C(F)F)c(-c2nc(N3CCOCC3)nc(N3CCOCC3)n2)cn1] | 5-(4,6-dimorpholino-1,3,5-triazin-2-yl)-4-(trifluoromethyl)pyridin-2-amine |
| 2 | 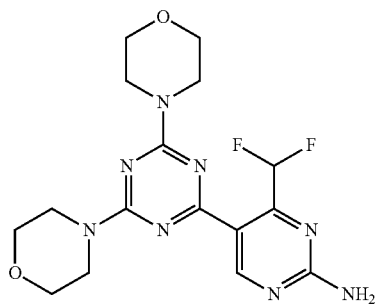 [SMILES: Nc1ncc(-c2nc(N3CCOCC3)nc(N3CCOCC3)n2)c(C(F)F)n1] | 4-(difluoromethyl)-5-(4,6-dimorpholino-1,3,5-triazin-2-yl)pyrimidin-2-amine |
| 2* | 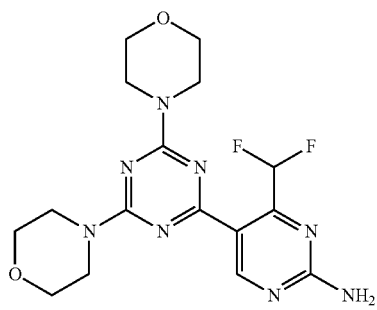 [SMILES: Nc1ncc(-c2nc(N3CCOCC3)nc(N3CCOCC3)n2)c(C(F)F)n1] | 5-(4,6-dimorpholino-1,3,5-triazin-2-yl)-4-(trifluoromethyl)pyrimidin-2-amine |
| 3 | 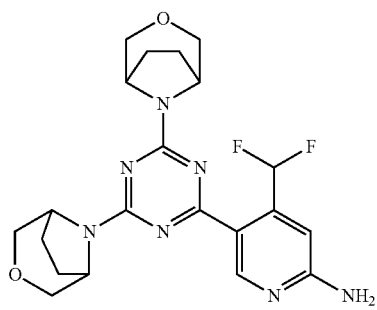 [SMILES: Nc1cc(C(F)F)c(-c2nc(N3C4CCC3COC4)nc(N3C4CCC3COC4)n2)cn1] | 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine |

| Compound | | |
|---|---|---|
| 4 | 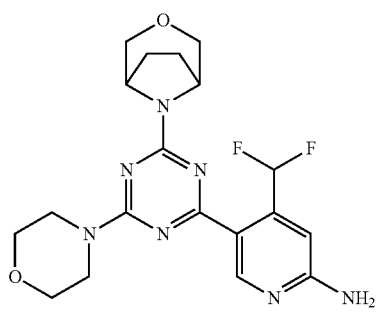 | 5-(4-(3-oxa-8-azabicyclo[3.2.1]octan-8-yl)-6-morpholino-1,3,5-triazin-2-yl)-4-(difluoromethyl)pyridin-2-amine |
| 5 | 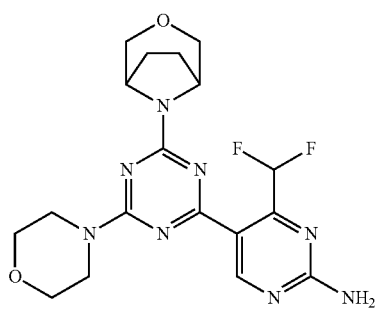 [SMILES: Nc1ncc(-c2nc(N3CCOCC3)nc(N3C4CCC3COC4)n2)c(C(F)F)n1] | 5-(4-(3-oxa-8-azabicyclo[3.2.1]octan-8-yl)-6-morpholino-1,3,5-triazin-2-yl)-4-(difluoromethyl)pyrimidin-2-amine |
| 6 | 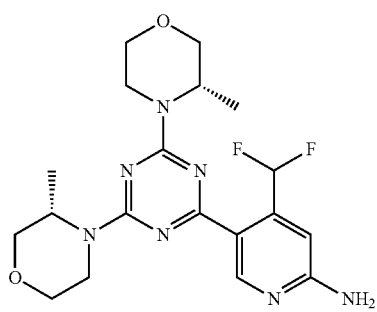 | 5-(4,6-bis((S)-3-methylmorpholino)-1,3,5-triazin-2-yl)-4-(difluoromethyl)pyridin-2-amine |
| 6* | 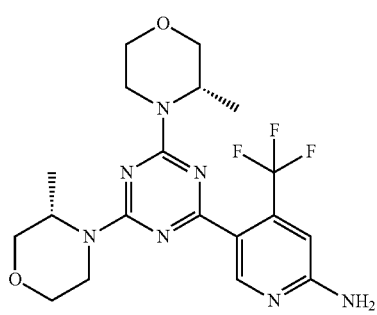 [SMILES: C[C@H]1COCCN1c1nc(-c2cnc(N)cc2C(F)(F)F)nc(N2CCOC[C@@H]2C)n1] | 5-[4,6-bis[(3S)-3-methylmorpholin-4-yl]-1,3,5-triazin-2-yl]-4-(trifluoromethyl)pyridin-2-amine |
| 7 | 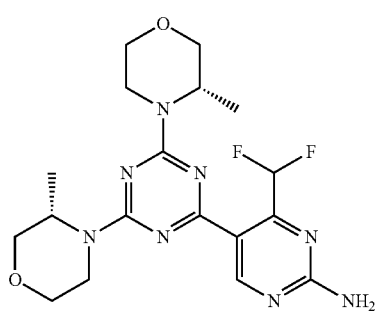 [SMILES: C[C@H]1COCCN1c1nc(-c2cnc(N)nc2C(F)F)nc(N2CCOC[C@@H]2C)n1] | 5-(4,6-bis((S)-3-methylmorpholino)-1,3,5-triazin-2-yl)-4-(difluoromethyl)pyrimidin-2-amine |

| Compound | | |
|---|---|---|
| 7* | 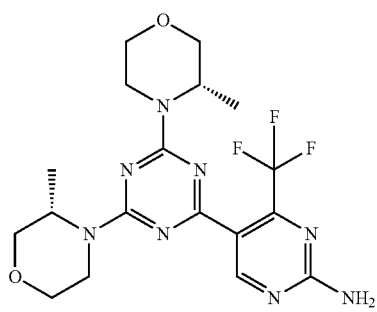 [SMILES: C[C@H]1COCCN1c1nc(-c2cnc(N)nc2C(F)(F)F)nc(N2CCOC[C@@H]2C)n1] | 5-[4,6-bis[(3S)-3-methylmorpholin-4-yl]-1,3,5-triazin-2-yl]-4-(trifluoromethyl)pyrimidin-2-amine |
| 8 | 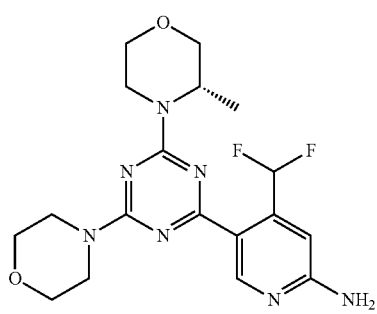 [SMILES: C[C@H]1COCCN1c1nc(-c2cnc(N)cc2C(F)F)nc(N2CCOCC2)n1] | (S)-4-(difluoromethyl)-5-(4-(3-methylmorpholino)-6-morpholino-1,3,5-triazin-2-yl)pyridin-2-amine |
| 8* | 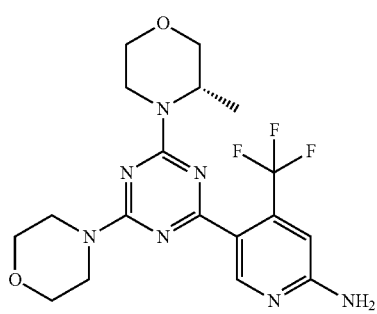 | 5-[4-[(3S)-3-methylmorpholin-4-yl]-6-morpholino-1,3,5-triazin-2-yl]-4-(trifluoromethyl)pyridin-2-amine |
| 9 | 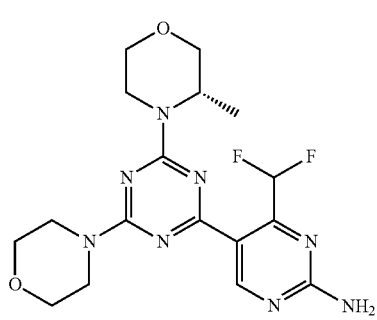 [SMILES: C[C@H]1COCCN1c1nc(-c2cnc(N)nc2C(F)F)nc(N2CCOCC2)n1] | (S)-4-(difluoromethyl)-5-(4-(3-methylmorpholino)-6-morpholino-1,3,5-triazin-2-yl)pyrimidin-2-amine |
| 9* | 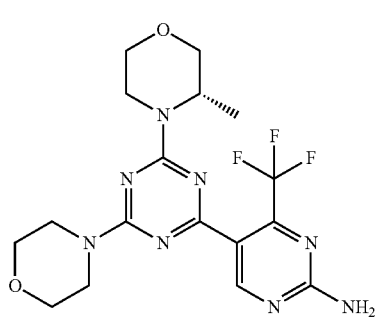 [SMILES: C[C@H]1COCCN1c1nc(-c2cnc(N)nc2C(F)(F)F)nc(N2CCOCC2)n1] | 5-[4-[(3S)-3-methylmorpholin-4-yl]-6-morpholino-1,3,5-triazin-2-yl]-4-(trifluoromethyl)pyrimidin-2-amine |

| Compound | | |
|---|---|---|
| 10 | 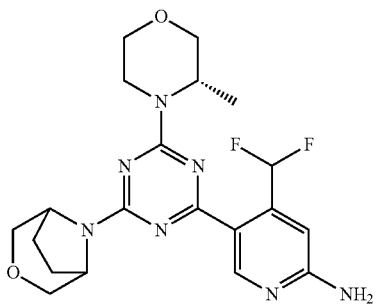 [SMILES: C[C@H]1COCCN1c1nc(-c2cnc(N)cc2C(F)F)nc(N2C3CCC2COC3)n1] | 5-(4-(3-oxa-8-azabicyclo[3.2.1]octan-8-yl)-6-((S)-3-methylmorpholino)-1,3,5-triazin-2-yl)-4-(difluoromethyl)pyridin-2-amine |
| 11 | 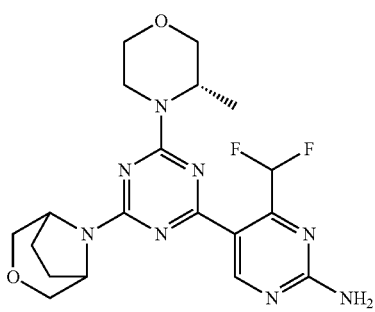 [SMILES: C[C@H]1COCCN1c1nc(-c2cnc(N)nc2C(F)F)nc(N2C3CCC2COC3)n1] | 5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine |
| 12 | 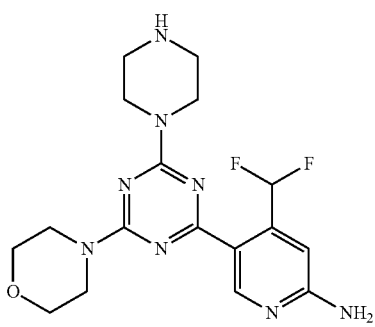 [SMILES: Nc1cc(C(F)F)c(-c2nc(N3CCNCC3)nc(N3CCOCC3)n2)cn1] | 4-(difluoromethyl)-5-(4-morpholino-6-(piperazin-1-yl)-1,3,5-triazin-2-yl)pyridin-2-amine |
| 12* | 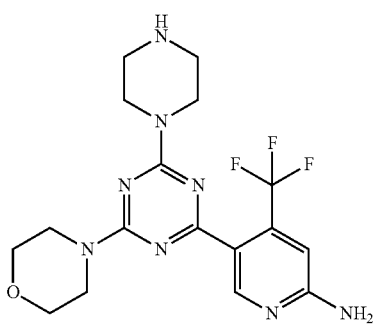 [SMILES: Nc1cc(C(F)(F)F)c(-c2nc(N3CCNCC3)nc(N3CCOCC3)n2)cn1] | 5-(4-morpholino-6-piperazin-1-yl-1,3,5-triazin-2-yl)-4-(trifluoromethyl)pyridin-2-amine |
| 13 | 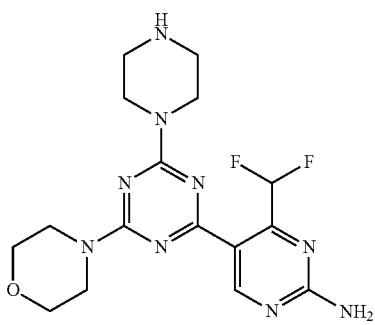 [SMILES: Nc1ncc(-c2nc(N3CCNCC3)nc(N3CCOCC3)n2)c(C(F)F)n1] | 4-(difluoromethyl)-5-(4-morpholino-6-(piperazin-1-yl)-1,3,5-triazin-2-yl)pyrimidin-2-amine |

-continued
| Compound | | |
|---|---|---|
| 13* | 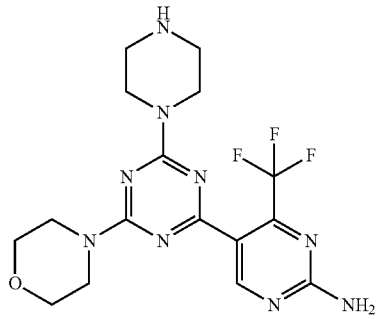 [SMILES: Nc1ncc(-c2nc(N3CCNCC3)nc(N3CCOCC3)n2)c(C(F)(F)F)n1] | 5-(4-morpholino-6-piperazin-1-yl)-1,3,5-triazin-2-yl)-4-(trifluoromethyl)pyrimidin-2-amine |
| 14 | 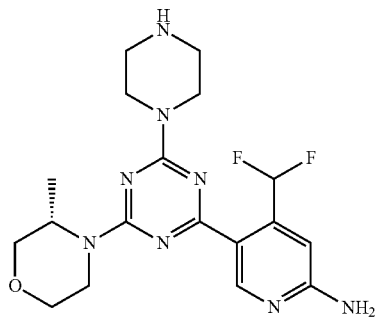 [SMILES: C[C@H]1COCCN1c1nc(-c2cnc(N)cc2C(F)F)nc(N2CCNCC2)n1] | (S)-4-(difluoromethyl)-5-(4-(3-methylmorpholino)-6-(piperazin-1-yl)-1,3,5-triazin-2-yl)pyridin-2-amine |
| 15 | 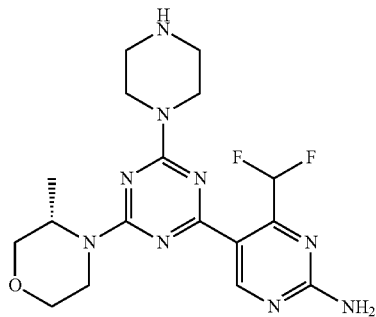 [SMILES: C[C@H]1COCCN1c1nc(-c2cnc(N)nc2C(F)F)nc(N2CCNCC2)n1] | (S)-4-(difluoromethyl)-5-(4-(3-methylmorpholino)-6-(piperazin-1-yl)-1,3,5-triazin-2-yl)pyrimidin-2-amine |
| 16 | 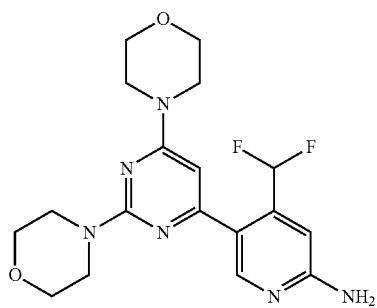 [SMILES: Nc1cc(C(F)F)c(-c2cc(N3CCOCC3)nc(N3CCOCC3)n2)cn1] | 4-(difluoromethyl)-5-(2,6-dimorpholinopyrimidin-4-yl)pyridin-2-amine |

-continued
| Compound | | |
|---|---|---|
| 17 | 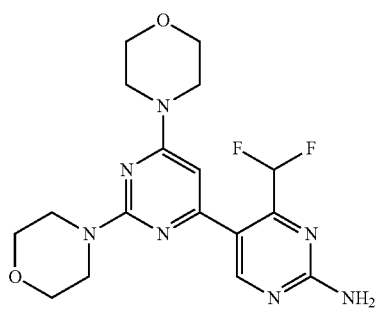 [SMILES: Nc1ncc(-c2cc(N3CCOCC3)nc(N3CCOCC3)n2)c(C(F)F)n1] | 4'-(difluoromethyl)-2,6-dimorpholino-[4,5'-bipyrimidin]-2'-amine |
| 18 | 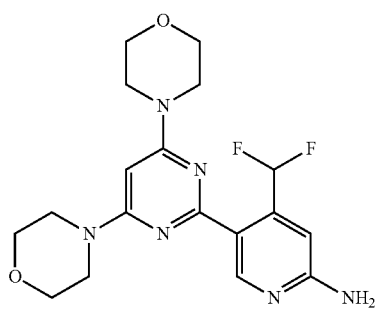 [SMILES: Nc1cc(C(F)F)c(-c2nc(N3CCOCC3)cc(N3CCOCC3)n2)cn1] | 4-(difluoromethyl)-5-(4,6-dimorpholino-pyrimidin-2-yl)pyridin-2-amine |
| 19 | 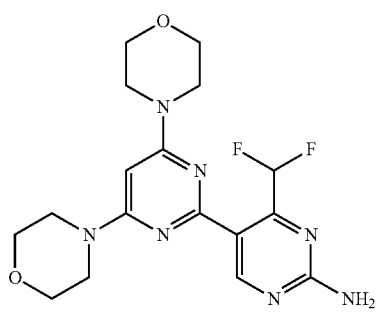 | 4'-(difluoromethyl)-4,6-dimorpholino-[2,5'-bipyrimidin]-2'-amine |
| 20 | 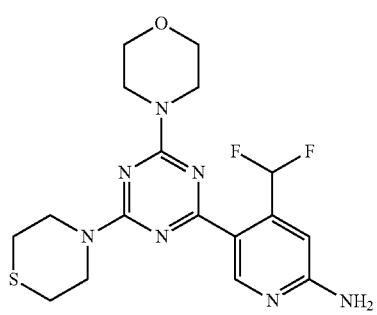 [SMILES: Nc1cc(C(F)F)c(-c2nc(N3CCOCC3)nc(N3CCSCC3)n2)cn1] | 4-(difluoromethyl)-5-(4-morpholino-6-thiomorpholino-1,3,5-triazin-2-yl)pyridin-2-amine |
| 20* | 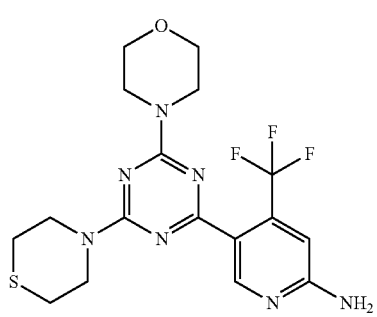 [SMILES: Nc1cc(C(F)(F)F)c(-c2nc(N3CCOCC3)nc(N3CCSCC3)n2)cn1] | 5-(4-morpholino-6-thiomorpholino-1,3,5-triazin-2-yl)-4-(trifluoromethyl)pyridin-2-amine |

-continued

| Compound | | |
|---|---|---|
| 21 | 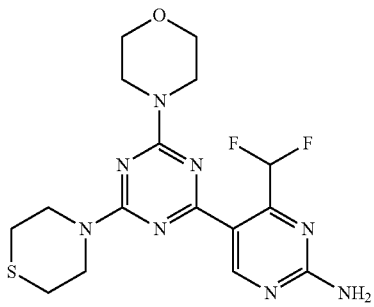 | 4-(difluoromethyl)-5-(4-morpholino-6-thiomorpholino-1,3,5-triazin-2-yl)pyrimidin-2-amine |
| 21* | 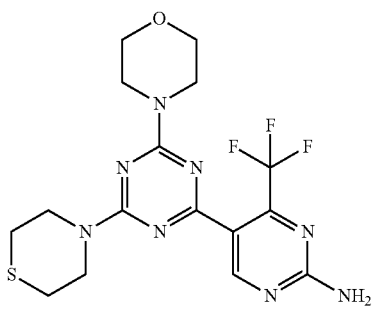 [SMILES: Nc1ncc(-c2nc(N3CCOCC3)nc(N3CCSCC3)n2)c(C(F)(F)F)n1] | 5-(4-morpholino-6-thiomorpholino-1,3,5-triazin-2-yl)-4-(trifluoromethyl)pyrimidin-2-amine |
| 22 | 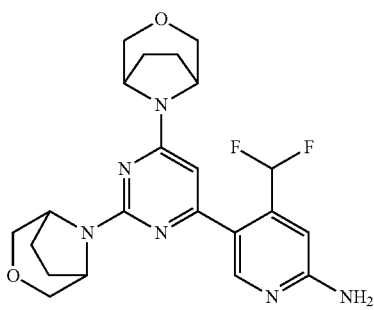 | 5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine |
| 23 | 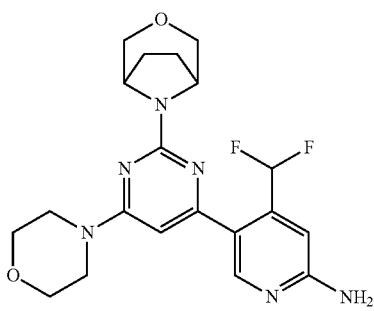 [SMILES: Nc1cc(C(F)F)c(-c2cc(N3CCOCC3)nc(N3C4CCC3COC4)n2)cn1] | 5-(2-(3-oxa-8-azabicyclo[3.2.1]octan-8-yl)-6-morpholinopyrimidin-4-yl)-4-(difluoromethyl)pyridin-2-amine |
| 24 | 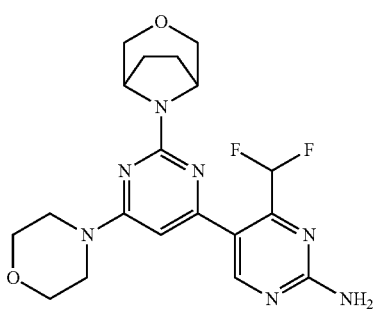 [SMILES: Nc1ncc(-c2cc(N3CCOCC3)nc(N3C4CCC3COC4)n2)c(C(F)F)n1] | 2-(3-oxa-8-azabicyclo[3.2.1]octan-8-yl)-4'-(difluoromethyl)-6-morpholino-[4,5'-bipyrimidin]-2'-amine |

-continued

| Compound | | |
|---|---|---|
| 25 | 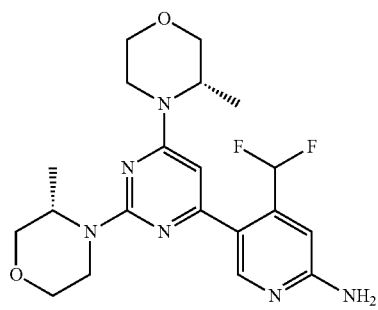 [SMILES: C[C@H]1COCCN1c1cc(-c2cnc(N)cc2C(F)F)nc(N2CCOC[C@@H]2C)n1] | 5-(2,6-bis((S)-3-methylmorpholino)-pyrimidin-4-yl)-4-(difluoromethyl)pyridin-2-amine |
| 26 | 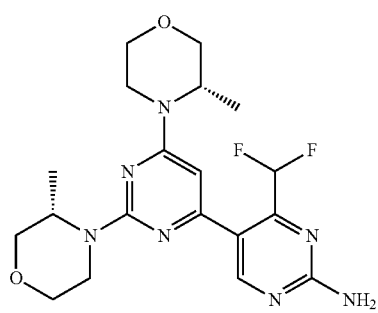 | 4'-(difluoromethyl)-2,6-bis((S)-3-methylmorpholino)-[4,5'-bipyrimidin]-2'-amine |
| 27 | 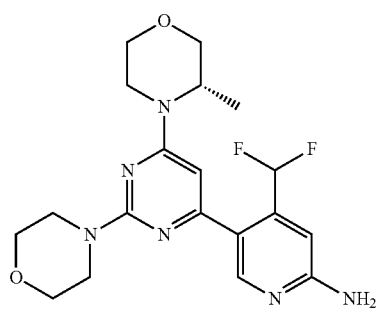 | (S)-4-(difluoromethyl)-5-(6-(3-methylmorpholino)-2-morpholinopyrimidin-4-yl)pyridin-2-amine |
| 28 | 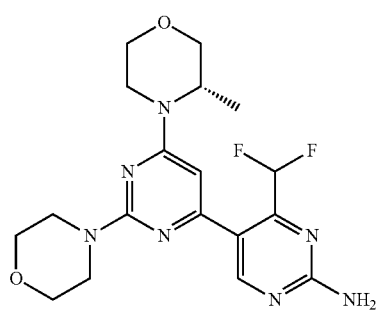 [SMILES: C[C@H]1COCCN1c1cc(-c2cnc(N)nc2C(F)F)nc(N2CCOCC2)n1] | (S)-4'-(difluoromethyl)-6-(3-methylmorpholino)-2-morpholino-[4,5'-bipyrimidin]-2'-amine |
| 29 | 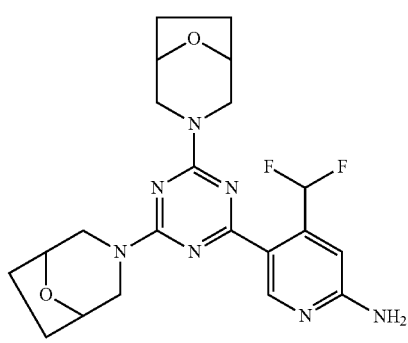 [SMILES: Nc1cc(C(F)F)c(-c2nc(N3CC4CCC(C3)O4)nc(N3CC4CCC(C3)O4)n2)cn1] | 5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine |

| Compound | | |
|---|---|---|
| 30 | 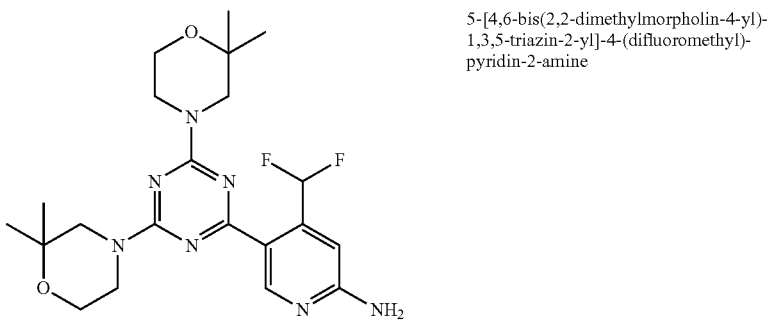 | 5-[4,6-bis(2,2-dimethylmorpholin-4-yl)-1,3,5-triazin-2-yl]-4-(difluoromethyl)-pyridin-2-amine |
| 31 | 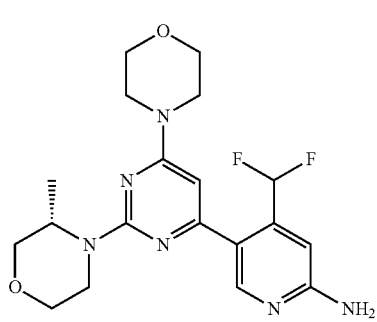 | (S)-4-(difluoromethyl)-5-(2-(3-methylmorpholino)-6-morpholinopyrimidin-4-yl)pyridin-2-amine |
| 32 | 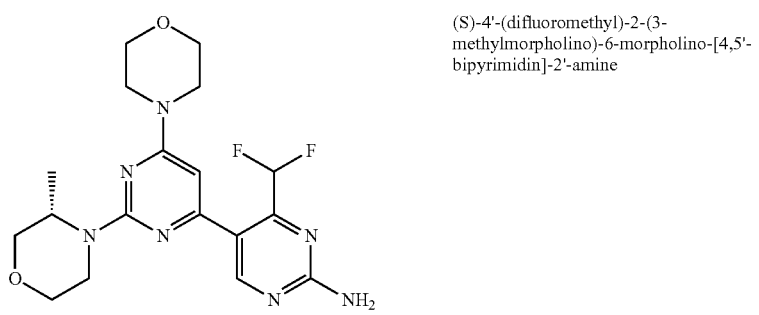 | (S)-4'-(difluoromethyl)-2-(3-methylmorpholino)-6-morpholino-[4,5'-bipyrimidin]-2'-amine |
| 33 | 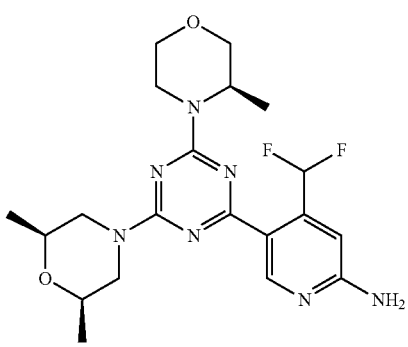 [SMILES: C[C@@H]1CN(c2nc(-c3cnc(N)cc3C(F)F)nc(N3CCOC[C@H]3C)n2)C[C@H](C)O1] | 4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine |

| Compound | | |
|---|---|---|
| 34 | 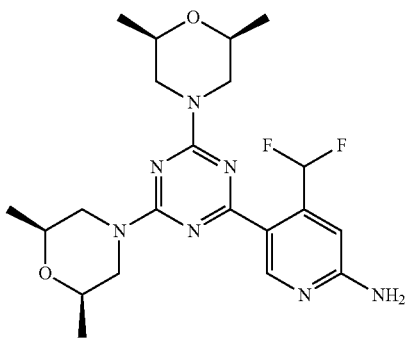 [SMILES: C[C@@H]1CN(c2nc(-c3cnc(N)cc3C(F)F)nc(N3C[C@@H](C)O[C@@H](C)C3)n2)C[C@H](C)O1] | 5-[4,6-bis[(2R,6S)-2,6-dimethylmorpholin-4-yl]-1,3,5-triazin-2-yl]-4-(difluoromethyl)pyridin-2-amine |
| 37 | 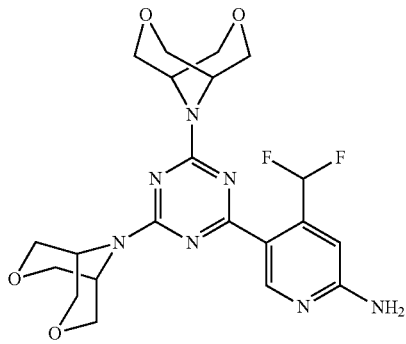 [SMILES: Nc1cc(C(F)F)c(-c2nc(N3C4COCC3COC4)nc(N3C4COCC3COC4)n2)cn1] | 5-[4,6-bis(3,7-dioxa-9-azabicyclo[3.3.1]nonan-9-yl)-1,3,5-triazin-2-yl]-4-(difluoromethyl)pyridin-2-amine |
| 38 | 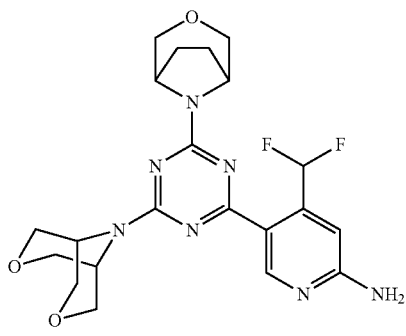 [SMILES: Nc1cc(C(F)F)c(-c2nc(N3C4CCC3COC4)nc(N3C4COCC3COC4)n2)cn1] | 4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine |
| 39 | 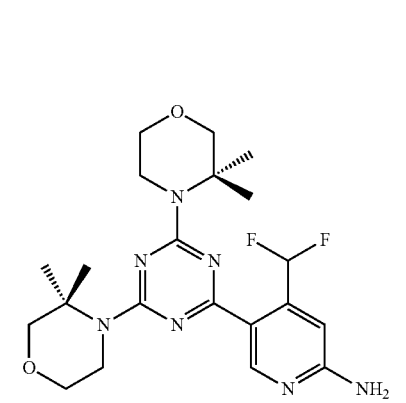 | 5-[4,6-bis(3,3-dimethylmorpholin-4-yl)-1,3,5-triazin-2-yl]-4-(difluoromethyl)-pyridin-2-amine |

| Compound | | |
|---|---|---|
| 40 | 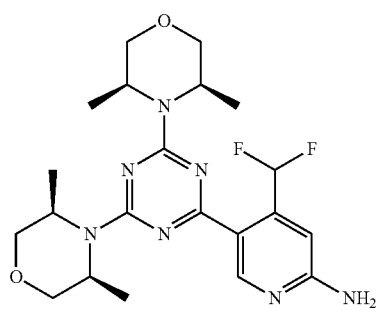 [SMILES: C[C@@H]1COC[C@H](C)N1c1nc(-c2cnc(N)cc2C(F)F)nc(N2[C@H](C)COC[C@@H]2C)n1] | 5-[4,6-bis[(3R,5S)-3,5-dimethylmorpholin-4-yl]-1,3,5-triazin-2-yl]-4-(difluoromethyl)pyridin-2-amine |
| 41 | 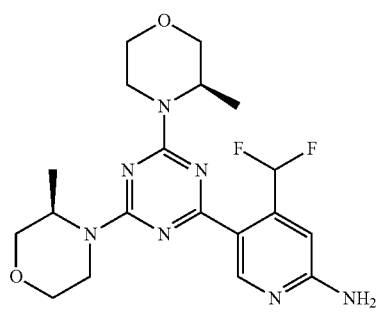 [SMILES: C[C@@H]1COCCN1c1nc(-c2cnc(N)cc2C(F)F)nc(N2CCOC[C@H]2C)n1] | 5-[4,6-bis[(3R)-3-methylmorpholin-4-yl]-1,3,5-triazin-2-yl]-4-(difluoromethyl)pyridin-2-amine |
| 42 | 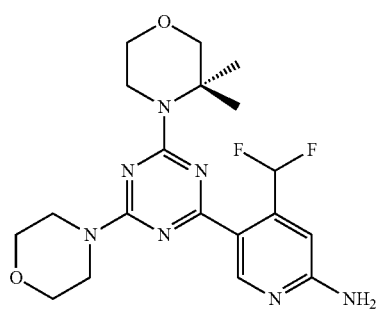 | 4-(difluoromethyl)-5-[4-(3,3-dimethylmorpholin-4-yl)-6-morpholino-1,3,5-triazin-2-yl]pyridin-2-amine |
| 44 | 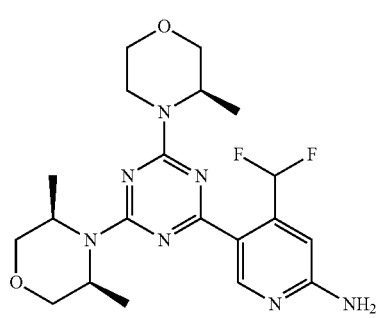 [SMILES: C[C@@H]1COCCN1c1nc(-c2cnc(N)cc2C(F)F)nc(N2[C@H](C)COC[C@@H]2C)n1] | 4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine |
| 45 | 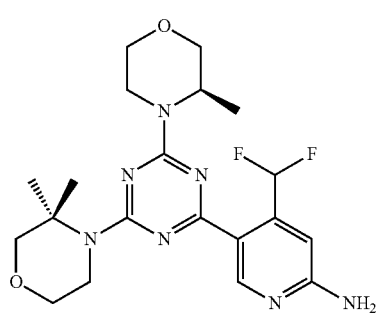 | 4-(difluoromethyl)-5-[4-(3,3-dimethylmorpholin-4-yl)-6-[(3R)-3-methylmorpholin-4-yl]-1,3,5-triazin-2-yl]pyridin-2-amine |

-continued

| Compound | | |
|---|---|---|
| 46 | 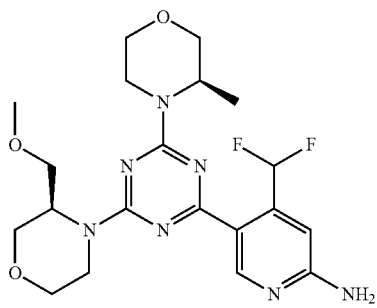 [SMILES: COC[C@@H]1COCCN1c1nc(-c2cnc(N)cc2C(F)F)nc(N2CCOC[C@H]2C)n1] | 4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine |
| 47 | 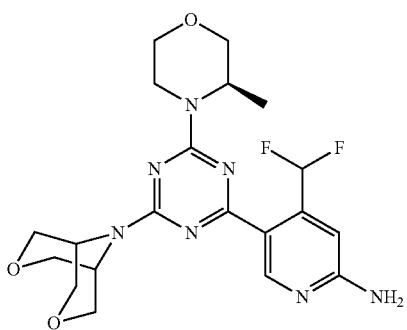 [SMILES: C[C@@H]1COCCN1c1nc(-c2cnc(N)cc2C(F)F)nc(N2C3COCC2COC3)n1] | 4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine |
| 50 | 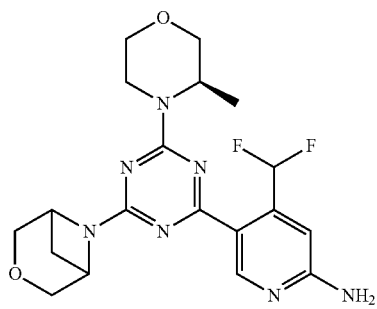 [SMILES: C[C@@H]1COCCN1c1nc(-c2cnc(N)cc2C(F)F)nc(N2C3COCC2C3)n1] | 4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine |
| 51 | 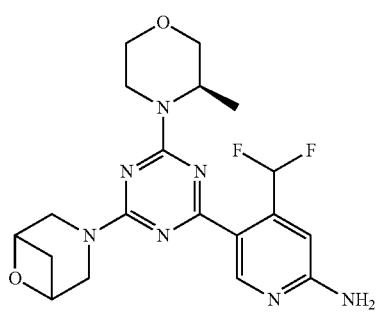 [SMILES: C[C@@H]1COCCN1c1nc(-c2cnc(N)cc2C(F)F)nc(N2CC3CC(C2)O3)n1] | 4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine |
| 52 | 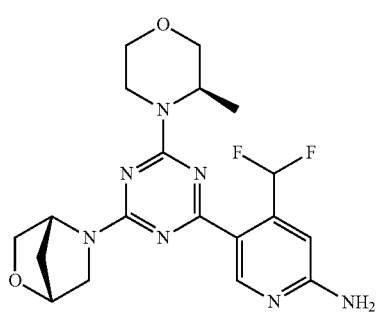 [SMILES: C[C@@H]1COCCN1c1nc(-c2cnc(N)cc2C(F)F)nc(N2C[C@H]3C[C@@H]2CO3)n1] | 4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine |

| Compound | | |
|---|---|---|
| 53 | 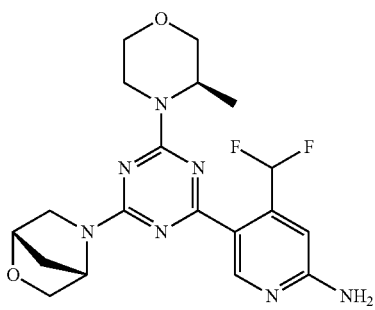 [SMILES: C[C@@H]1COCCN1c1nc(-c2cnc(N)cc2C(F)F)nc(N2C[C@@H]3C[C@H]2CO3)n1] | 4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine |
| 54 | 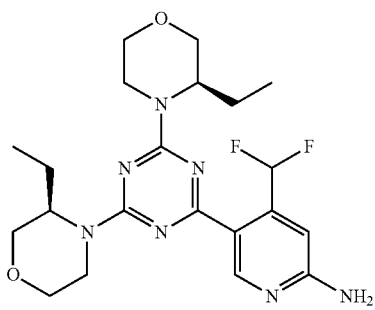 [SMILES: CC[C@@H]1COCCN1c1nc(-c2cnc(N)cc2C(F)F)nc(N2CCOC[C@H]2CC)n1] | 5-[4,6-bis[(3R)-3-ethylmorpholin-4-yl]-1,3,5-triazin-2-yl]-4-(difluoromethyl)pyridin-2-amine |
| 55 | 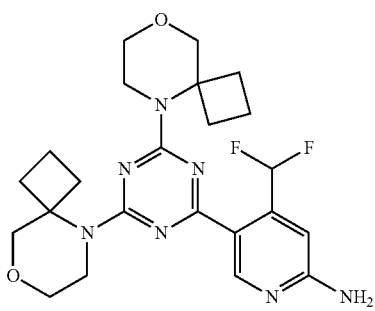 [SMILES: Nc1cc(C(F)F)c(-c2nc(N3CCOCC34CCC4)nc(N3CCOCC34CCC4)n2)cn1] | 5-[4,6-bis(8-oxa-5-azaspiro[3.5]nonan-5-yl)-1,3,5-triazin-2-yl]-4-(difluoromethyl)pyridin-2-amine |
| 56 | 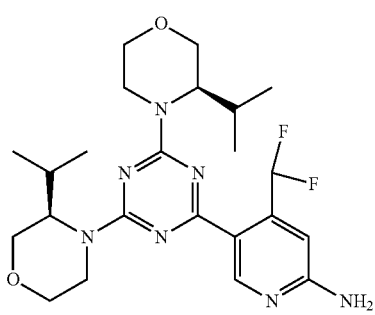 [SMILES: CC(C)[C@@H]1COCCN1c1nc(-c2cnc(N)cc2C(F)F)nc(N2CCOC[C@H]2C(C)C)n1] | 5-[4,6-bis[(3R)-3-isopropylmorpholin-4-yl]-1,3,56-triazin-2-yl]-4-(difluoromethyl)pyridin-2-amine |
| 66 | 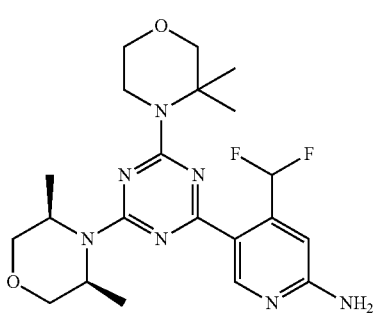 [SMILES: C[C@@H]1COC[C@H](C)N1c1nc(-c2cnc(N)cc2C(F)F)nc(N2CCOCC2(C)C)n1] | 4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine |

-continued

| Compound | | |
|---|---|---|
| 67 | 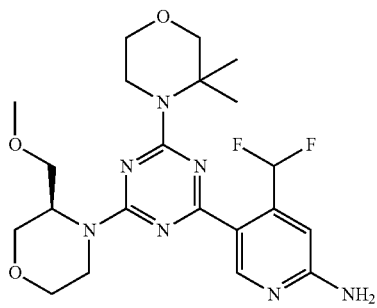 [SMILES: COC[C@@H]1COCCN1c1nc(-c2cnc(N)cc2C(F)F)nc(N2CCOCC2(C)C)n1] | 4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine |
| 68 | 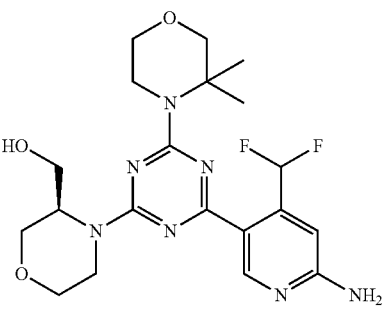 [SMILES: CC1(C)COCCN1c1nc(-c2cnc(N)cc2C(F)F)nc(N2CCOC[C@H]2CO)n1] | [(3R)-4-[4-[6-amino-4-(difluoromethyl)-3-pyridyl]-6-(3,3-dimethylmorpholin-4-yl)-1,3,5-triazin-2-yl]morpholin-3-yl]methanol |
| 69 | 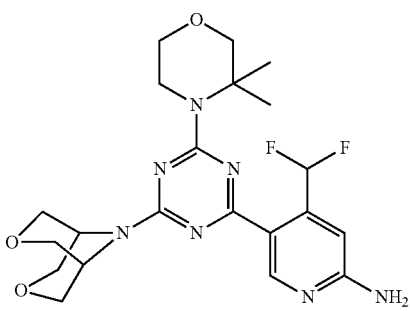 [SMILES: CC1(C)COCCN1c1nc(-c2cnc(N)cc2C(F)F)nc(N2C3COCC2COC3)n1] | 4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine |
| 70 | 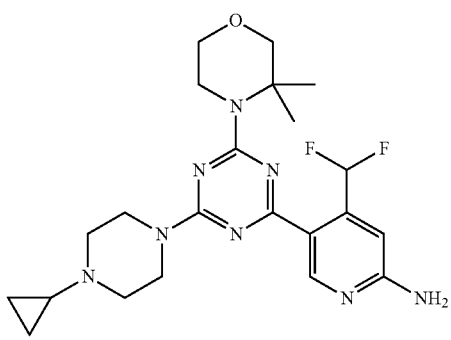 [SMILES: CC1(C)COCCN1c1nc(-c2cnc(N)cc2C(F)F)nc(N2CCN(C3CC3)CC2)n1] | 5-[4-(4-cyclopropylpiperazin-1-yl)-6-(3,3-dimethylmorpholin-4-yl)-1,3,5-triazin-2-yl]-4-(difluoromethyl)pyridin-2-amine |
| 71 | 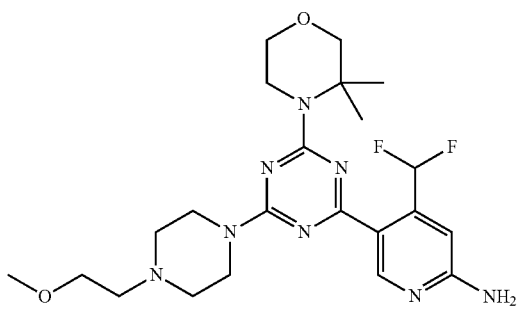 [SMILES: COCCN1CCN(c2nc(-c3cnc(N)cc3C(F)F)nc(N3CCOCC3(C)C)n2)CC1] | 4-(difluoromethyl)-5-[4-(3,3-dimethylmorpholin-4-yl)-6-[4-(2-methoxyethyl)piperazin-1-yl]-1,3,5-triazin-2-yl]pyridin-2-amine |

| Compound | | |
|---|---|---|
| 77 | 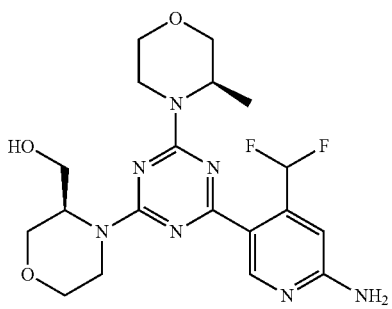 [SMILES: C[C@@H]1COCCN1c1nc(-c2cnc(N)cc2C(F)F)nc(N2CCOC[C@H]2CO)n1] | [(3R)-4-[4-[6-amino-4-(difluoromethyl)-3-pyridyl]-6-[(3R)-3-methylmorpholin-4-yl]-1,3,5-triazin-2-yl]morpholin-3-yl]methanol |
| 78 | 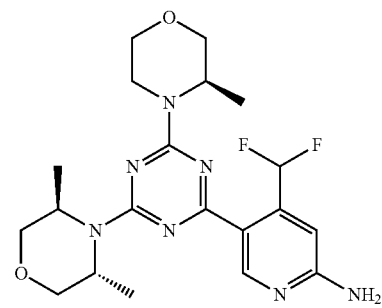 [SMILES: C[C@@H]1COCCN1c1nc(-c2cnc(N)cc2C(F)F)nc(N2[C@H](C)COC[C@H]2C)n1] | 4-(difluoromethyl)-5-[4-[(3R,5)-3,5-dimethylmorpholin-4-yl]-6-[(3R)-3-methylmorpholin-4-yl]-1,3,5-triazin-2-yl]pyridin-2-amine |
| 79 | 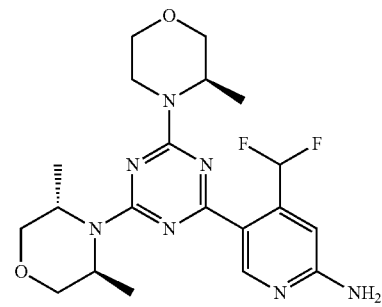 [SMILES: C[C@@H]1COCCN1c1nc(-c2cnc(N)cc2C(F)F)nc(N2[C@@H](C)COC[C@@H]2C)n1] | 4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine |
| 80 | 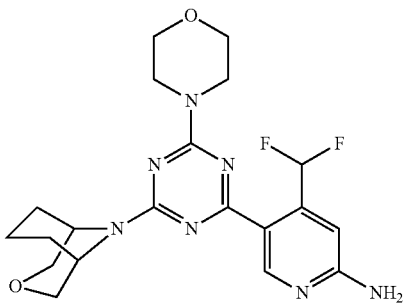 [SMILES: Nc1cc(C(F)F)c(-c2nc(N3CCOCC3)nc(N3C4CCCC3COC4)n2)cn1] | 4-(difluoromethyl)-5-[4-morpholino-6-(3-oxa-9-azabicyclo[3.3.1]nonan-9-yl)-1,3,5-triazin-2-yl]pyridin-2-amine |
| 82 | 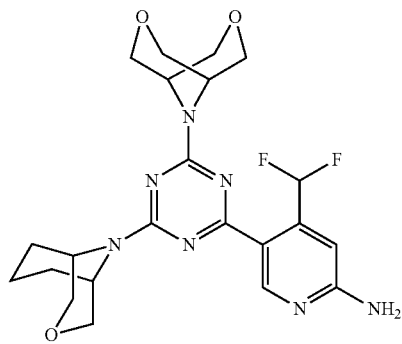 [SMILES: Nc1cc(C(F)F)c(-c2nc(N3C4CCCC3COC4)nc(N3C4COCC3COC4)n2)cn1] | 4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine |

| Compound | | |
|---|---|---|
| 83 | 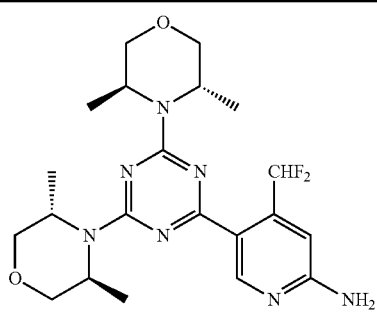 | 5-[4,6-bis[(3S,5S)-3,5-dimethylmorpholin-4-yl]-1,3,5-triazin-2-yl]-4-(difluoromethyl)pyridin-2-amine |
| 84 | 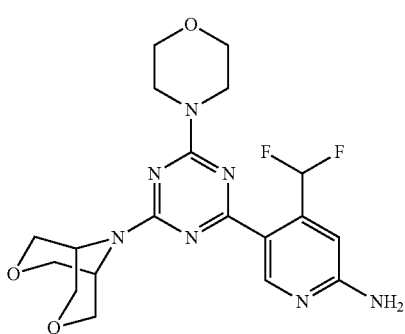 [SMILES: Nc1cc(C(F)F)c(-c2nc(N3CCOCC3)nc(N3C4COCC3COC4)n2)cn1] | 4-(difluoromethyl)-5-[4-(3,7-dioxa-9-azabicyclo[3.3.1]nonan-9-yl)-6-morpholino-1,3,5-triazin-2-yl]pyridin-2-amine |
| 85 | 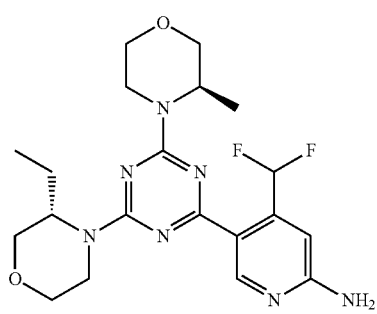 [SMILES: CC[C@H]1COCCN1c1nc(-c2cnc(N)cc2C(F)F)nc(N2CCOC[C@H]2C)n1] | 4-(difluoromethyl)-5-[4-[(3S)-3-ethylmorpholin-4-yl]-6-[(3R)-3-methylmorpholin-4-yl]-1,3,5-triazin-2-yl]pyridin-2-amine |
| 86 | 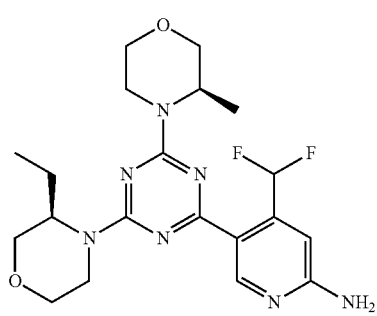 [SMILES: CC[C@@H]1COCCN1c1nc(-c2cnc(N)cc2C(F)F)nc(N2CCOC[C@H]2C)n1] | 4-(difluoromethyl)-5-[4-[(3R)-3-ethylmorpholin-4-yl]-6-[(3R)-3-methylmorpholin-4-yl]-1,3,5-triazin-2-yl]pyridin-2-amine |
| 88 | 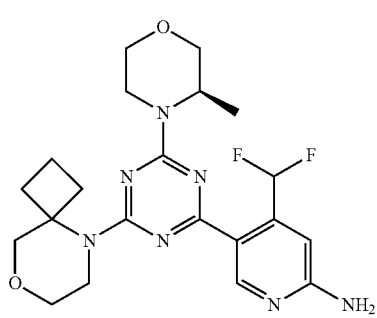 [SMILES: C[C@@H]1COCCN1c1nc(-c2cnc(N)cc2C(F)F)nc(N2CCOCC23CCC3)n1] | 4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine |

Preparation of Compounds of the Invention

The compounds of the invention may be synthesized by synthetic routes that include processes analogous to those well known in the chemical arts, particularly in light of the description contained herein. Moreover, the synthesis of compounds of the present invention and the intermediates used for said synthesis of compounds of the present invention have already been described in WO 2016/075130 as well as in the application PCT/EP2017/025137 filed on May 17, 2017. The starting materials are generally available from commercial sources or are readily prepared using methods well known to those skilled in the art.

In preparing compounds of the invention, protection of remote functionality (e.g., primary or secondary amine) of intermediates may be necessary. The need for such protection will vary depending on the nature of the remote functionality and the conditions of the preparation methods. Suitable amino-protecting groups include tert-butyloxycarbonyl (BOC), bis-tert-butyloxycarbonyl or dimethylaminomethylenyl. The need for such protection is readily determined by one skilled in the art. For a general description of protecting groups and their use, see T. W. Greene, *Protective Groups in Organic Synthesis*, John Wiley & Sons, New York, 1991.

Methods of Separation

In the methods of preparing the compounds of this invention, it may be advantageous to separate reaction products from one another and/or from starting materials. The desired products of each step or series of steps are separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; high, medium and low pressure liquid chromatography methods and apparatus; small scale analytical; and preparative thin or thick layer chromatography, as well as techniques of small scale thin layer and flash chromatography.

Selection of appropriate methods of separation depends on the nature of the materials involved, for example, presence or absence of polar functional groups in chromatography, stability of materials in acidic and basic media in multiphase extraction, and the like. One skilled in the art will apply techniques most likely to achieve the desired separation.

EXAMPLES

The Examples are intended to illustrate the present invention without restricting it.

The chemical reactions described in the Examples may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

As a rule, $^1$H NMR and mass spectra have been obtained for the compounds prepared. In the Examples described below, unless otherwise indicated, all temperatures are set forth in degrees Celsius (° C.). Reagents were purchased from commercial suppliers such as Sigma Aldrich, Fluorochem, Acros, Lancaster, TCI or Maybridge, and were used without further purification unless otherwise indicated. The reactions set forth below were done generally under a positive pressure of nitrogen or with a drying tube (unless otherwise stated) in anhydrous solvents, and the reaction flasks were typically fitted with rubber septa for the introduction of substrates and reagents via syringe. Glassware was oven dried. Column chromatography was performed using Merck silica gel. $^1$H NMR spectra were recorded on a Bruker instrument operating at 400 MHz. $^1$H NMR spectra were obtained for solutions in various deuterated solvents such as $CDCl_3$, $(CD_3)_2SO$, $CD_3OD$ or $(CD_3)_2CO$. The chemical shift δ values were reported in ppm and corrected to the signal of the deuterated solvents (7.26 ppm for $CDCl_3$) or TMS (0 ppm). $^{19}$F NMR spectra were calibrated relative to $CFCl_3$ (δ=0 ppm) as external standard. $^{19}$F NMR spectra were recorded $^1$H-decoupled. When peak multiplicities are reported, the following abbreviations are used: s (singlet), d (doublet), t (triplet), m (multiplet), quint (quintet), br (broadened). Coupling constants, when given, are reported in Hertz (Hz). MALDI-ToF Mass spectra (MS) have been obtained on a Voyager-De™ Pro measured in m/z.

The following abbreviations are used hereinafter: BSA (bovine serum albumin), DMSO (dimethyl sulfoxide), ESI (electrospray ionization), HCl (hydrochloric acid), M (molar), MALDI (Matrix-assisted Laser Desorption/Ionization), MS (mass spectrometry), PBS (phosphate buffered saline), TLC (thin layer chromatography), nd (not determined).

Example 1

Preparation of Intermediate Compounds and of Compounds of the Invention

Preparation of Intermediate Compounds

The following methods were used to prepare the intermediates compounds used to produce compounds of formula (I). Said methods used to prepare said intermediates and the synthesis of the exemplified intermediates used for preparing the compounds of the present invention have already been described in WO 2016/075130 as well as in the application PCT/EP2017/025137 filed on May 17, 2017. Therein, these methods are numbered and referred to as "Method 1", "Method 2" or the like, wherein the intermediates exemplified and synthesized by said methods are referred to as "i1", "i2" or the like. Such numbering is used to distinguish the intermediates from the compounds of formula (I). When reference is made to the compounds of formula (I) a compound number such as "1", "2", "1*", 2*" or the like without the prefix "i" is used. The same numbering concept as well as the same specific reference and reference number for the specific methods, the specific intermediates and the specific compounds is used herein. As a consequence, with respect to the methods, the specific intermediates and the specific compounds of the present invention it is explicitly referred to the corresponding disclosure of WO 2016/075130 as well as of the application PCT/EP2017/025137 filed on May 17, 2017.

Method 1: 8-(4-(3-oxa-8-azabicyclo[3.2.1]octan-8-yl)-6-chloro-1,3,5-triazin-2-yl)-3-oxa-8-azabicyclo[13.2.1]octane (ii)

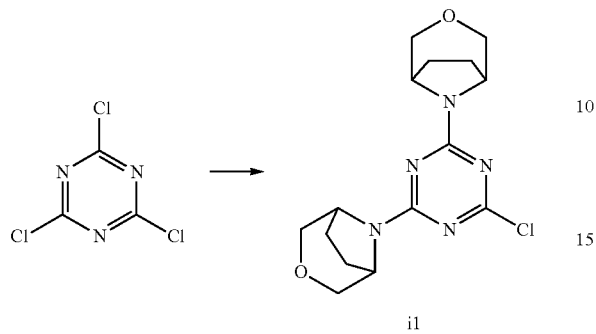

i1

Method 1 and the synthesis of it was conducted as described in WO2016/075130 and in the application PCT/EP2017/025137 filed on May 17, 2017.

Method 1 was also used for the preparation of the intermediate compounds i2 to i10, and intermediates i79 to i81 and i90.

| | Reagent | Structure |
|---|---|---|
| i2 | morpholine | triazine with two morpholines and Cl |
| i3 | (3S)-3-methylmorpholine | triazine with two (3-methylmorpholine) groups and Cl |
| i4 | (3R,3R)-3,3-dimethylmorpholine | triazine with two 3,3-dimethylmorpholine groups and Cl |

| | | |
|---|---|---|
| i5 | 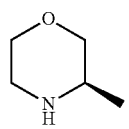 | 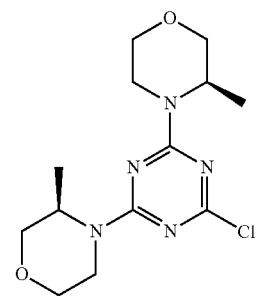 [SMILES: C[C@@H]1COCCN1c1nc(Cl)nc(N2CCOC[C@H]2C)n1] |
| i6 | 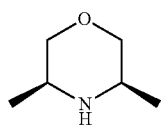 | 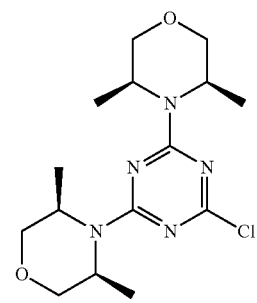 [SMILES: C[C@@H]1COC[C@H](C)N1c1nc(Cl)nc(N2[C@H](C)COC[C@@H]2C)n1] |
| i7 | 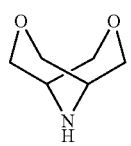 | 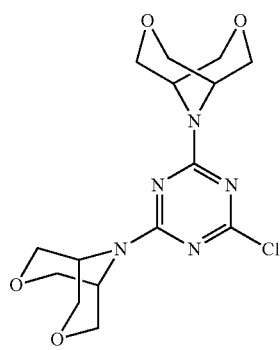 [SMILES: Clc1nc(N2C3COCC2COC3)nc(N2C3COCC2COC3)n1] |
| i8 | 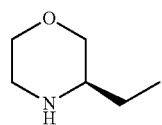 | 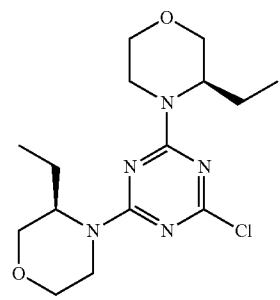 [SMILES: CC[C@@H]1COCCN1c1nc(Cl)nc(N2CCOC[C@H]2CC)n1] |
| i9 | 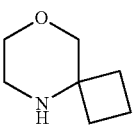 | 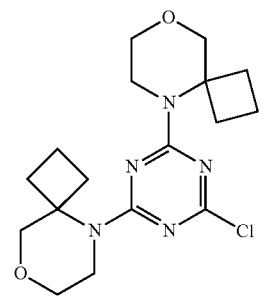 [SMILES: Clc1nc(N2CCOCC23CCC3)nc(N2CCOCC23CCC3)n1] |

| | | | |
|---|---|---|---|
| i10 | 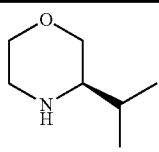 | 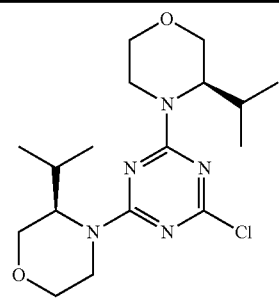 | |
| i79 | 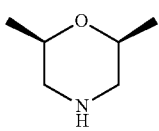 | 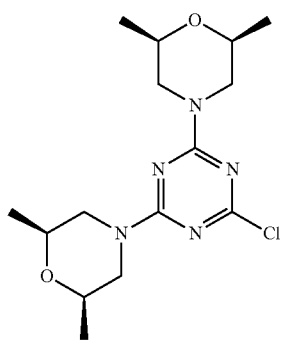 | |
| i80 | 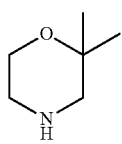 | 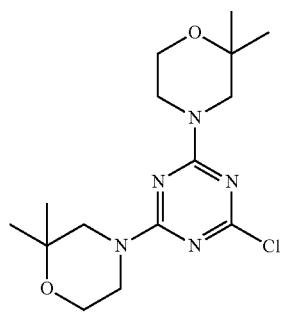 | |
| i81 | 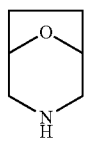 | 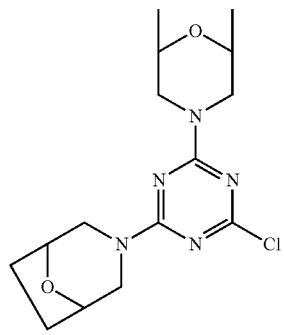 [SMILES: CC1CN(c2nc(Cl)nc(N3CC4CCC(C3)O4)n2)CC(C)O1] | |
| | Reagent | Structure | NMR | MS |
|---|---|---|---|---|
| i90 | 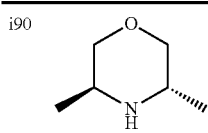 | 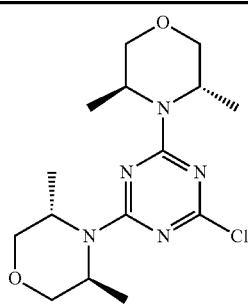 | $^1$H NMR (400 MHz, CDCl$_3$): δ 4.20 (m, 4 H), 4.10 (m, 4 H), 3.66 (m, 4 H), 1.35 (d, $^3J_{H,H}$ = 6.9 Hz, 12 H) | MS (MALDI): m/z = 342.8 ([M + H]$^+$) |

Method 2: 2,4-dichloro-6-morpholino-1,3,5-triazine (i11)

Method 3: 8-(4-chloro-6-morpholino-1,3,5-triazin-2-yl)-3-oxa-8-azabicyclo-[3.2.1]octane (i12)

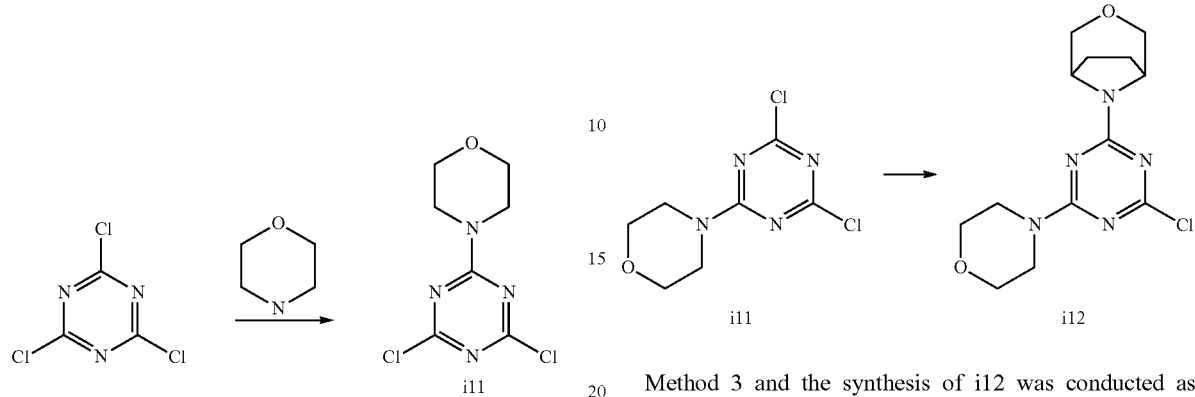

Method 2 and the synthesis of i11 was conducted as described in WO 2016/075130 and in the application PCT/EP2017/025137 filed on May 17, 2017.

Method 3 and the synthesis of i12 was conducted as described in WO2016/075130 and in the application PCT/EP2017/025137 filed on May 17, 2017.

Method 3 was also used for the preparation of the intermediate compounds i13 to i16, and intermediates i87 and i91.

| | Reagent | Structure |
|---|---|---|
| i13 | | 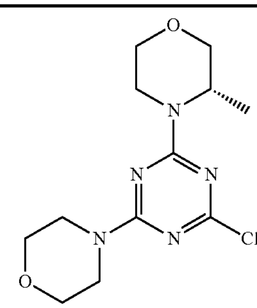 |
| i14 | | 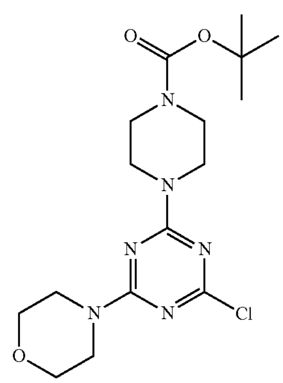 [SMILES: CC(C)(C)OC(=O)N1CCN(c2nc(Cl)nc(N3CCOCC3)n2)CC1] |
| i15 | | 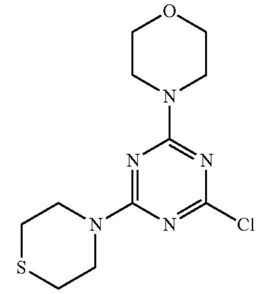 [SMILES: Clc1nc(N2CCOCC2)nc(N2CCSCC2)n1] |

| Reagent | Structure | NMR |
|---|---|---|
| i16 | | |
| i87 | 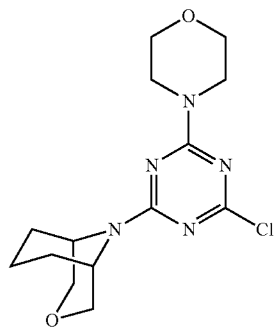 [SMILES: Clc1nc(N2CCOCC2)nc(N2C3CCCC2COC3)n1] | ¹H NMR (400 MHz, CDCl₃): δ 4.52 (m, 1 H), 4.43 (m, 1 H), 3.93 (m, 2 H), 3.65 (m, 10 H), 2.48 (m, 1 H), 1.88-1.72 (m, 4 H), 1.57 (m, 1 H) |
| i91 | 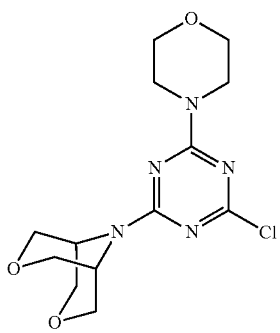 [SMILES: Clc1nc(N2CCOCC2)nc(N2C3COCC2COC3)n1] | ¹H NMR (400 MHz, CDCl₃): δ 4.44 (m, 1 H), 4.32 (m, 1 H), 4.00 (m, 4 H), 3.74-3.65 (m, 12 H); |
Method 4: (S)-4-(4,6-dichloro-1,3,5-triazin-2-yl)-3-methylmorpholine (i17)
Method 4 and the synthesis of i17 was conducted as described in WO 2016/075130 and in the application PCT/EP2017/025137 filed on May 17, 2017.
Method 5: 8-(4-chloro-6-((S)-3-methylmorpholino)-1,3,5-triazin-2-yl)-3-oxa-8-azabicyclo[3.2.1]octane (i18)
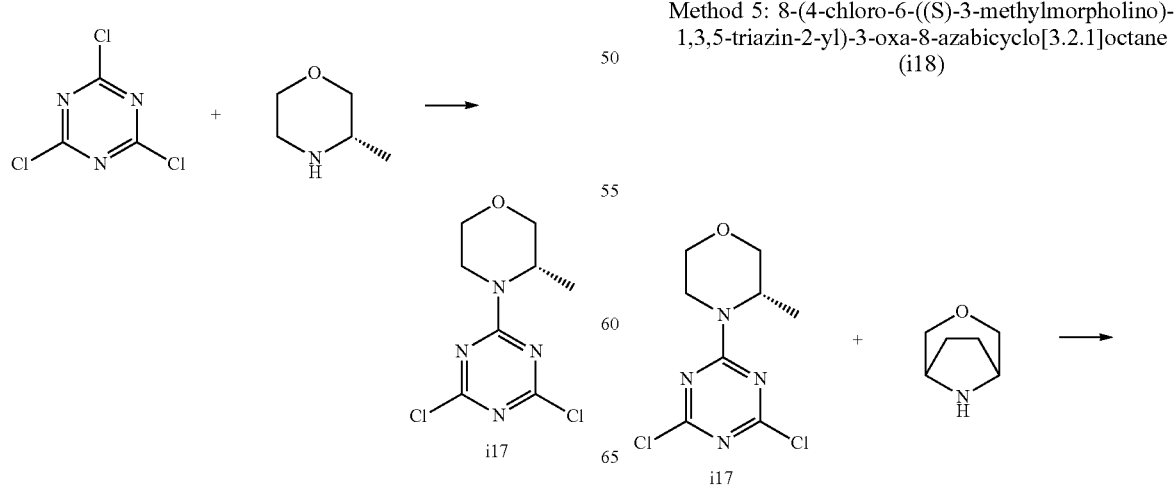

-continued

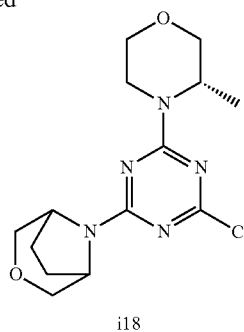

i18

Method 5 and the synthesis of i18 was conducted as described in WO 2016/075130 and in the application PCT/EP2017/025137 filed on May 17, 2017.

Method 6: tert-butyl 4-(4,6-dichloro-1,3,5-triazin-2-yl)piperazine-1-carboxylate (i19)

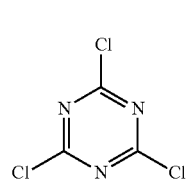  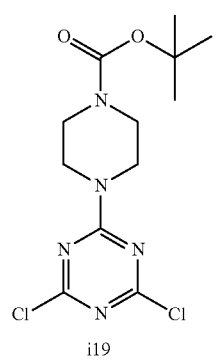

i19

Method 6 and the synthesis of i19 was conducted as described in WO 2016/075130 and in the application PCT/EP2017/025137 filed on May 17, 2017.

Method 7: tert-butyl 4-(4-(3-oxa-8-azabicyclo[3.2.1]octan-8-yl)-6-chloro-1,3,5-triazin-2-yl)piperazine-1-carboxylate (i20)

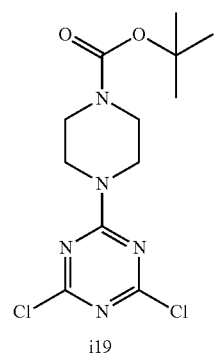  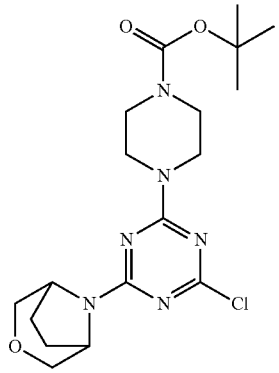

i19    i20

Method 7 and the synthesis of i20 was conducted as described in WO 2016/075130 and in the application PCT/EP2017/025137 filed on May 17, 2017.

Method 7 was also used for the preparation of the intermediate compound i21.

| Reagent | Structure |
|---|---|
| i21 | 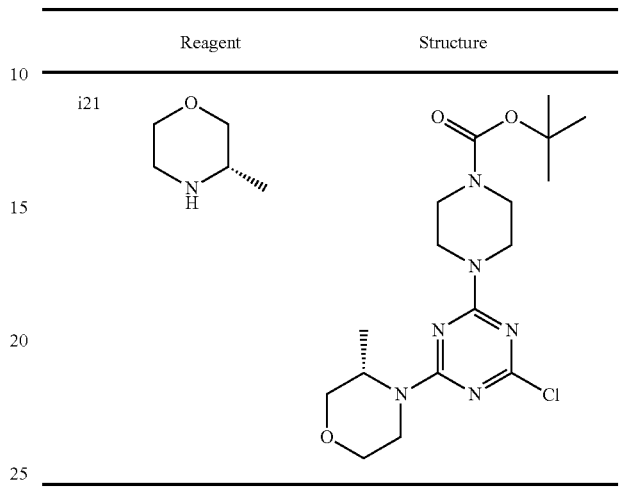 |

Method 8: 4,4'-(6-chloropyrimidine-2,4-diyl)dimorpholine (i22) and 4,4'-(2-chloropyrimidine-4,6-diyl)dimorpholine (i23)

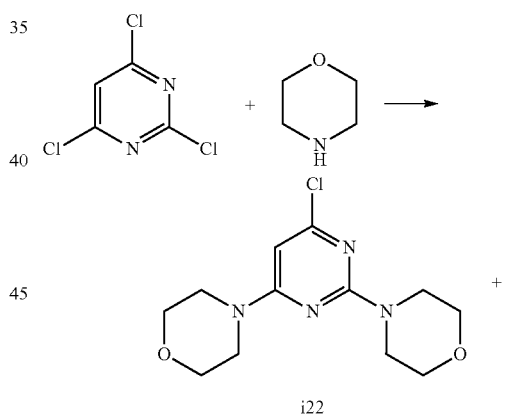

i22

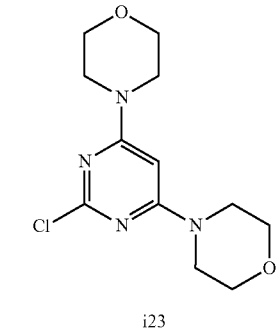

i23

Method 8 and the synthesis of i22 and i23 was conducted as described in WO2016/075130 and in the application PCT/EP2017/025137 filed on May 17, 2017.

Method 9: 8-(4-(3-oxa-8-azabicyclo[3.2.1]octan-8-yl)-6-chloropyrimidin-2-yl)-3-oxa-8-azabicyclo[3.2.1]octane (i24)

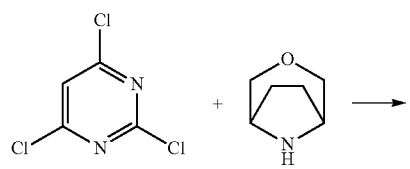

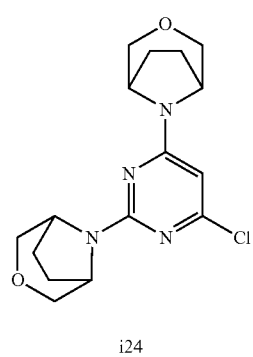

i24

Method 9 and the synthesis of i24 was conducted as described in WO2016/075130 and in the application PCT/EP2017/025137 filed on May 17, 2017.

Method 9 was also used for the preparation of the intermediate compound i25.

| Reagent | Structure |
|---|---|
| i25 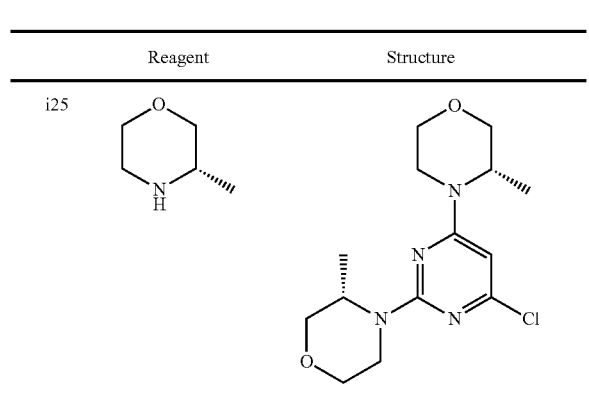 | 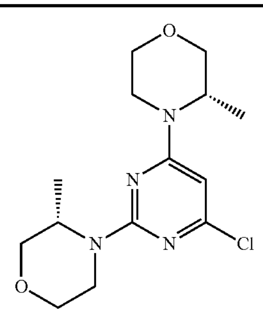 |

Method 10: 4-(4,6-dichloropyrimidin-2-yl)morpholine (i26) and 4-(2,6-dichloropyrimidin-4-yl)morpholine (i27)

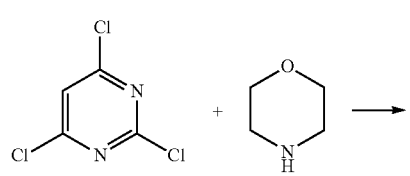

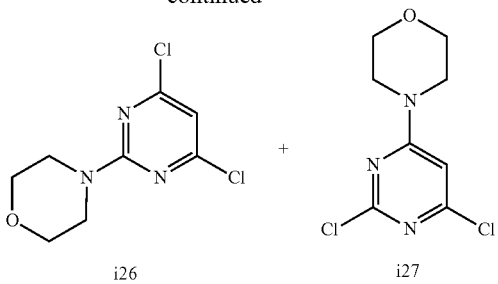

i26     i27

Method 10 and the synthesis of i26 and i27 was conducted as described in WO2016/075130 and in the application PCT/EP2017/025137 filed on May 17, 2017.

Method 11: (S)-4-(2-chloro-6-morpholinopyrimidin-4-yl)-3-methylmorpholine (i28)

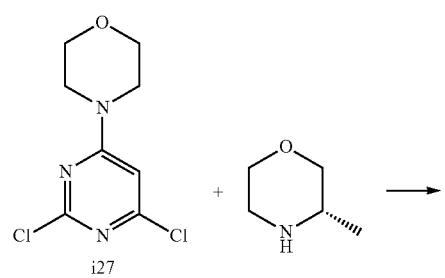

i27

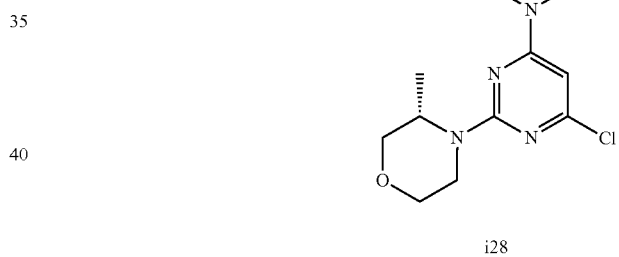

i28

Method 11 and the synthesis of i28 was conducted as described in WO2016/075130 and in the application PCT/EP2017/025137 filed on May 17, 2017.

Method 11 was also used for the preparation of the intermediate compound i29.

| Reagent | Structure |
|---|---|
| i29 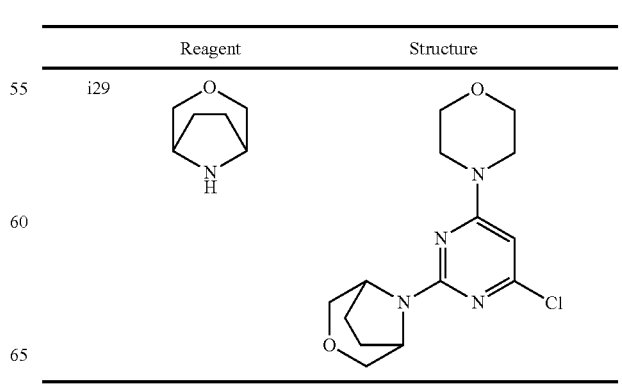 | 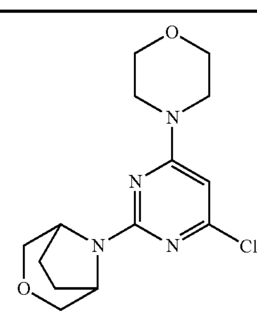 |

Method 12: (S)-4-(6-chloro-2-morpholinopyrimidin-4-yl)-3-methylmorpholine (i30)

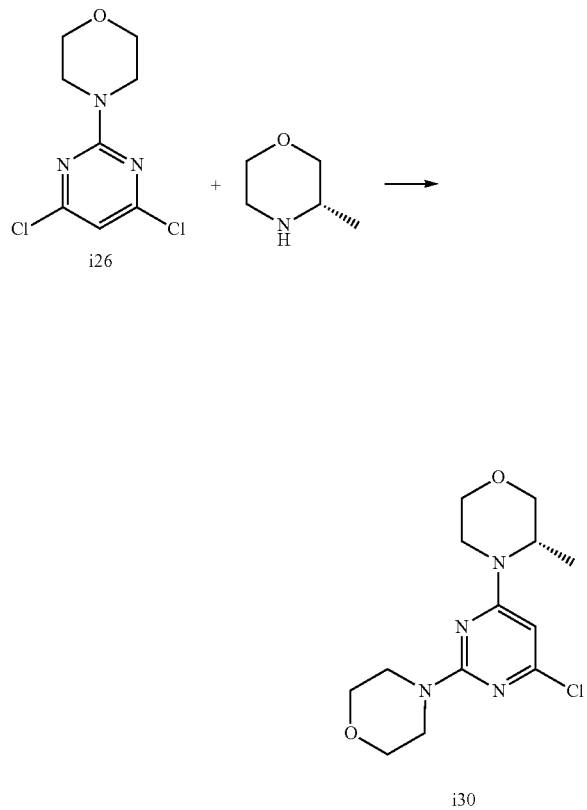

Method 12 and the synthesis of i30 was conducted as described in WO2016/075130 and in the application PCT/EP2017/025137 filed on May 17, 2017.

Method 14: 8-(4,6-dichloro-1,3,5-triazin-2-yl)-3-oxa-8-azabicyclo[3.2.1]octane (i32)

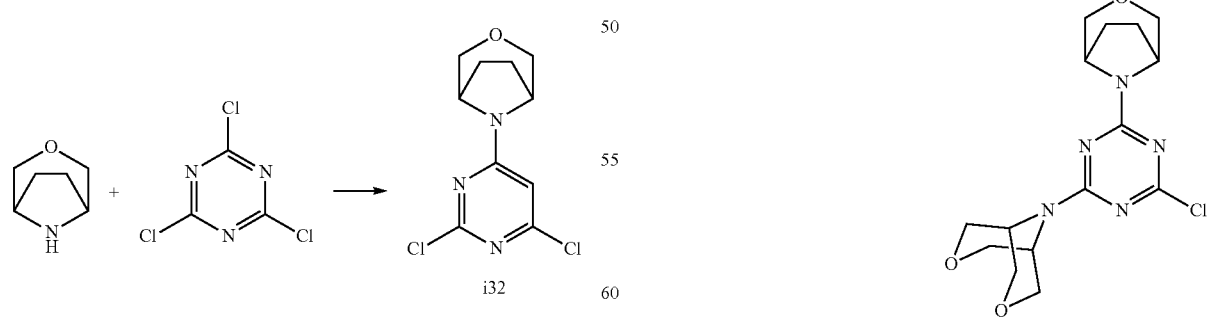

Method 14 and the synthesis of i32 was conducted as described in WO2016/075130 and in the application PCT/EP2017/025137 filed on May 17, 2017.

Method 14 was also used for the preparation of the intermediate compounds i33 and i34.

| Reagent | Structure |
|---|---|
| i33 | 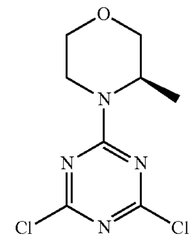 |
| i34 | 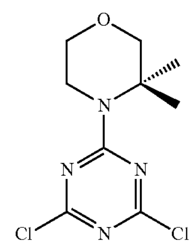 |

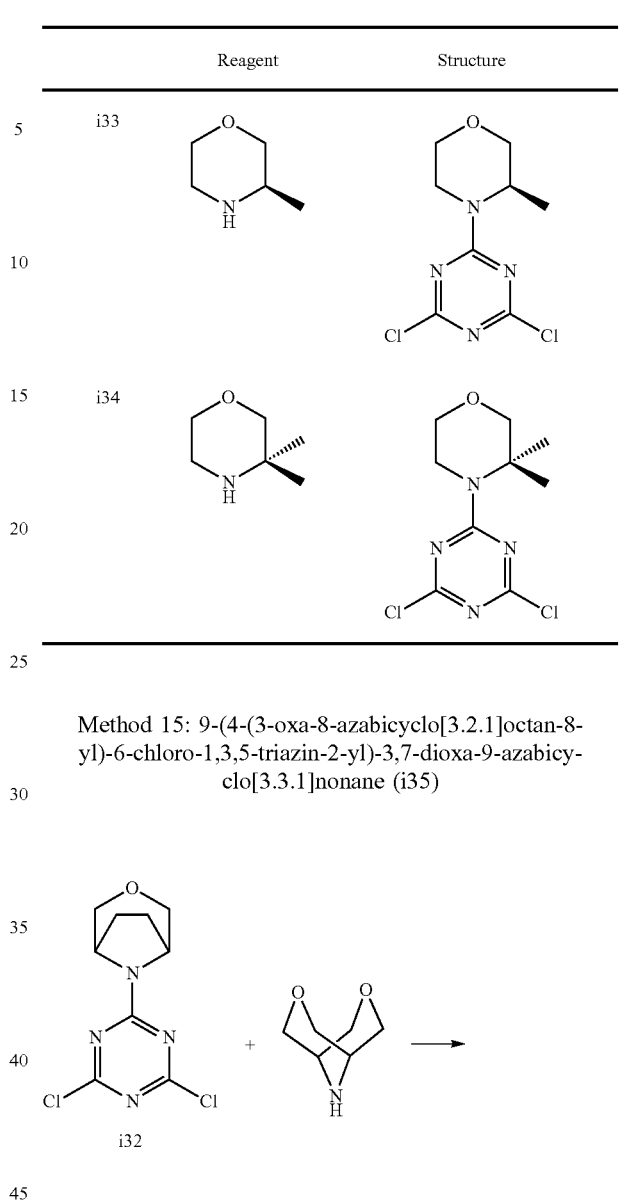

Method 15: 9-(4-(3-oxa-8-azabicyclo[3.2.1]octan-8-yl)-6-chloro-1,3,5-triazin-2-yl)-3,7-dioxa-9-azabicyclo[3.3.1]nonane (i35)

Method 15 and the synthesis of i35 was conducted as described in WO2016/075130 and in the application PCT/EP2017/025137 filed on May 17, 2017.

Method 16: 9-(4-chloro-6-((R)-3-methylmor-
pholino)-1,3,5-triazin-2-yl)-3,7-dioxa-9-azabicyclo
[3.3.1]nonane (i36)
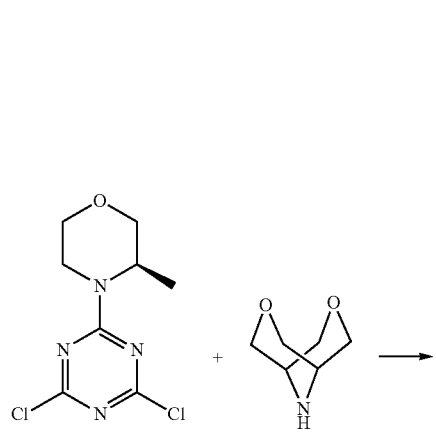
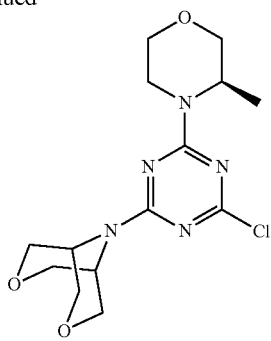
i33 i36
Method 16 and the synthesis of i36 was conducted as described in WO2016/075130 and in the application PCT/EP2017/025137 filed on May 17, 2017.
Method 16 was also used for the preparation of the intermediate compounds i37 to i53, intermediate i82 and intermediates i85, i86, i92, i93, i94.
| | Reagent | Structure | | Reagent | Structure |
|---|---|---|---|---|---|
| i37 | | 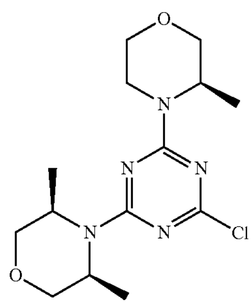 [SMILES: C[C@@H]1COCCN1c1nc(Cl)nc(N2[C@H](C)COC[C@@H]2C)n1] | i38 | | 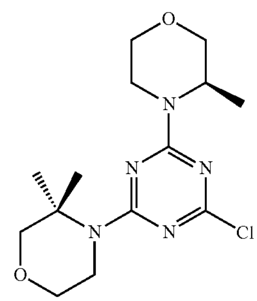 |
| i39 | | 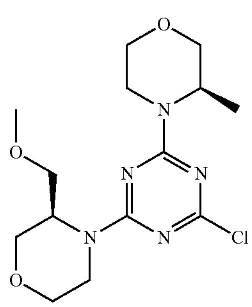 [SMILES: COC[C@@H]1COCCN1c1nc(Cl)nc(N2CCOC[C@H]2C)n1] | i40 | | 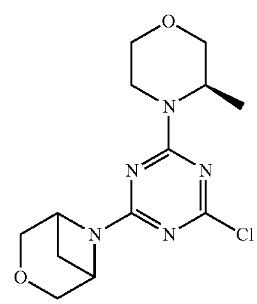 [SMILES: C[C@@H]1COCCN1c1nc(Cl)nc(N2C3COCC2C3)n1] |
| i41 | | 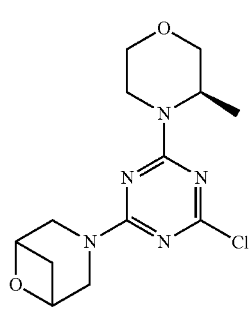 [SMILES: C[C@@H]1COCCN1c1nc(Cl)nc(N2CC3CC(C2)O3)n1] | i42 | | 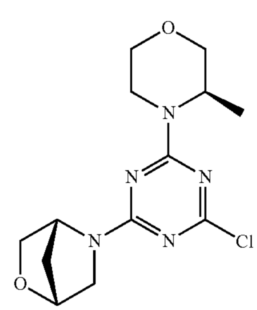 [SMILES: C[C@@H]1COCCN1c1nc(Cl)nc(N2C[C@H]3C[C@@H]2CO3)n1] |

-continued
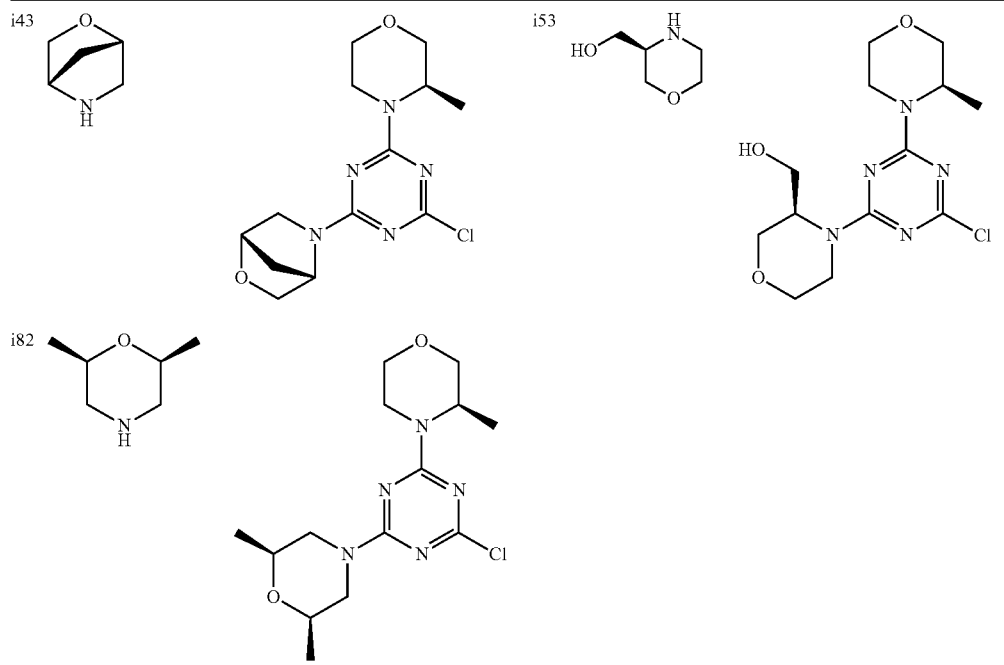
| | Reagent | Structure | NMR | MS |
|---|---|---|---|---|
| i85 | | 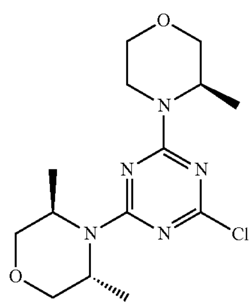 [SMILES: C[C@@H]1COCCN1c1nc(Cl)nc(N2[C@H](C)COC[C@H]2C)n1] | $^1$H NMR (400 MHz, (CD$_3$)$_2$SO): δ 4.53 (m, 1 H), 4.22 (m, 3 H), 4.11-4.08 (m, 2 H), 3.88 (m, 1 H), 3.66 (m, 3 H), 3.54 (m, 1 H), 3.36 (m, 1 H), 3.18 (m, 1 H), 1.33 (m, 6 H), 1.22 (d, $^3J_{H,H}$ = 6.9 Hz, 3 H) | MS (MALDI): m/z = 328.2 ([M + H]$^+$) |
| i86 | | 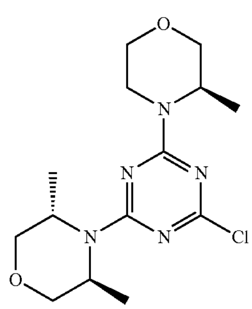 [SMILES: C[C@@H]1COCCN1c1nc(Cl)nc(N2[C@@H](C)COC[C@@H]2C)n1] | $^1$H NMR (400 MHz, (CD$_3$)$_2$SO): δ 4.55 (m, 1 H), 4.22-4.07 (m, 5 H), 3.88 (m, 1 H), 3.70-3.63 (m, 3 H), 3.54 (m, 1 H), 3.38 (m, 1 H), 3.19 (m, 1 H), 1.33 (m, 6 H), 1.21 (d, $^3J_{H,H}$ = 6.9 Hz, 3 H) | MS (MALDI): m/z = 328.5 ([M + H]$^+$). |
| i92 | | 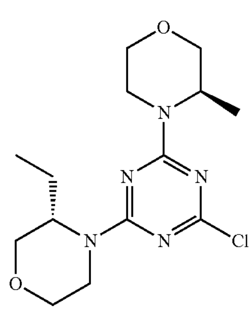 [SMILES: CC[C@H]1COCCN1c1nc(Cl)nc(N2CCOC[C@H]2C)n1] | $^1$H NMR (400 MHz, (CD$_3$)$_2$SO): δ 4.54-4.15 (m, 4 H), 3.86 (m, 2 H), 3.77 (m, 1 H), 3.66 (m, 2 H), 3.55-3.46 (m, 2 H), 3.38 (m, 1 H), 3.14 (m, 2 H), 1.70 (m, 2 H), 1.22 (d, $^3J_{H,H}$ = 6.9 Hz, 3 H), 0.86 (m, 3 H) | MS (MALDI): m/z = 328.6 ([M + H]$^+$). |

Method 17: 9-(4-chloro-6-(3,3-dimethylmorpholino)-1,3,5-triazin-2-yl)-3,7-dioxa-9-azabicyclo[3.3.1]nonane (i54)
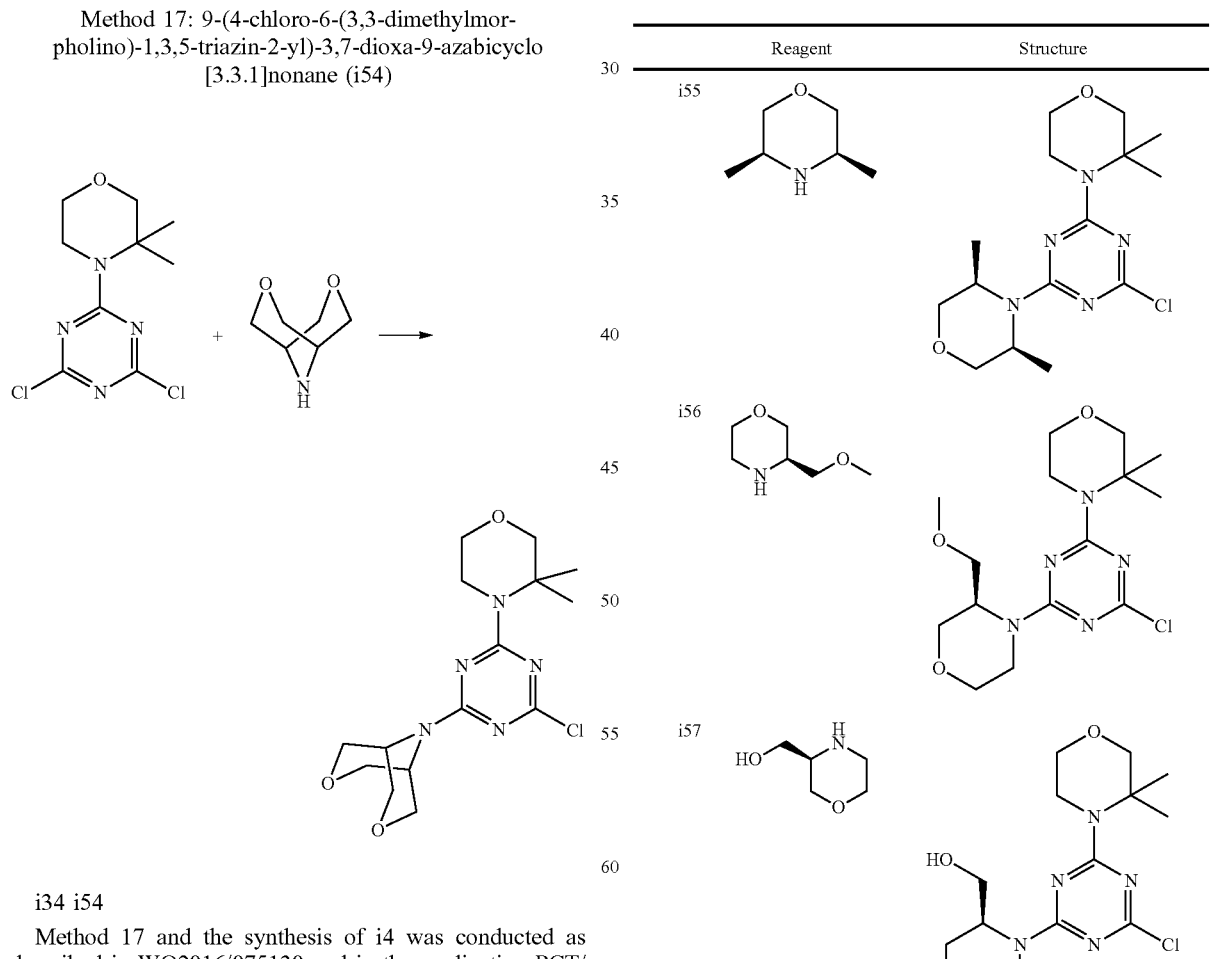
i34 i54
Method 17 and the synthesis of i4 was conducted as described in WO2016/075130 and in the application PCT/EP2017/025137 filed on May 17, 2017.
Method 17 was also used for the preparation of the following intermediate compounds i55 to i64.

| Reagent | Structure |
|---|---|
| i58 | 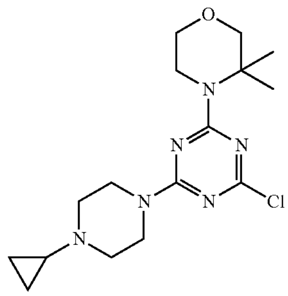 [SMILES: CC1(C)COCCN1c1nc(Cl)nc(N2CCN(C3CC3)CC2)n1] |
| i59 | 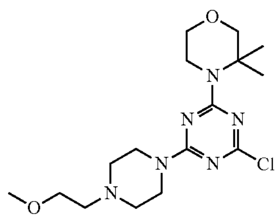 |

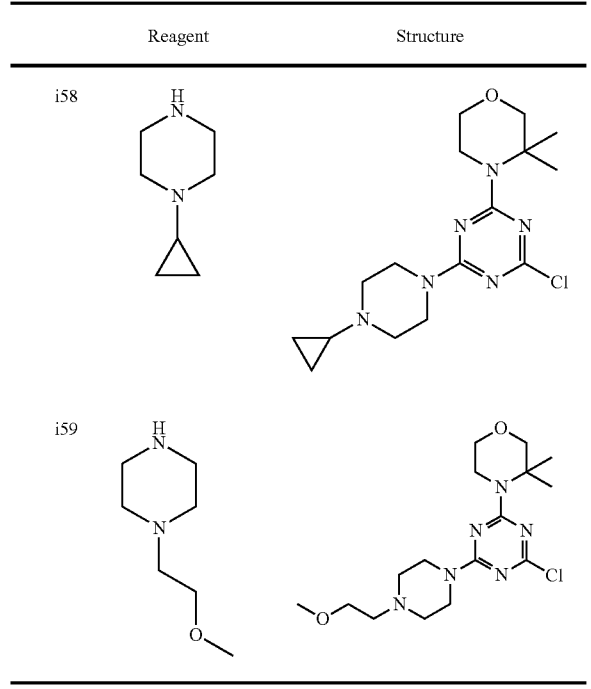

Method 18: 4-(difluoromethyl)pyridin-2-amine (i65)

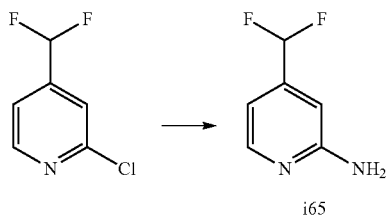 [SMILES: FC(F)c1ccnc(Cl)c1 ; Nc1cc(C(F)F)ccn1]

Method 18 and the synthesis of i4 was conducted as described in WO2016/075130 and in the application PCT/EP2017/025137 filed on May 17, 2017.

Method 19:
5-bromo-4-(difluoromethyl)pyridin-2-amine (i66)

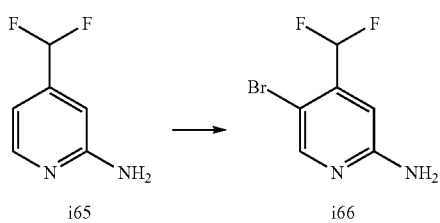 [SMILES: Nc1cc(C(F)F)ccn1 ; Nc1cc(C(F)F)c(Br)cn1]

Method 19 and the synthesis of i66 was conducted as described in WO2016/075130 and in the application PCT/EP2017/025137 filed on May 17, 2017.

Method 20: N'-(5-bromo-4-(difluoromethyl)pyridin-2-yl)-N,N-dimethylformimidamide (i67)

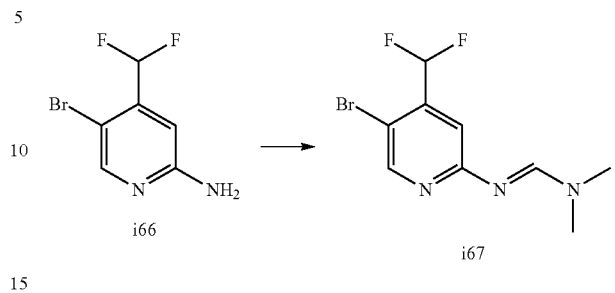

Method 20 and the synthesis of i67 was conducted as described in WO2016/075130 and in the application PCT/EP2017/025137 filed on May 17, 2017.

Method 21: N'-(4-(difluoromethyl)-5-(4,4,5,5-tetramethyl-1,3,2-dioxaborolan-2-yl)pyridin-2-yl)-N,N-dimethylformimidamide (i68)

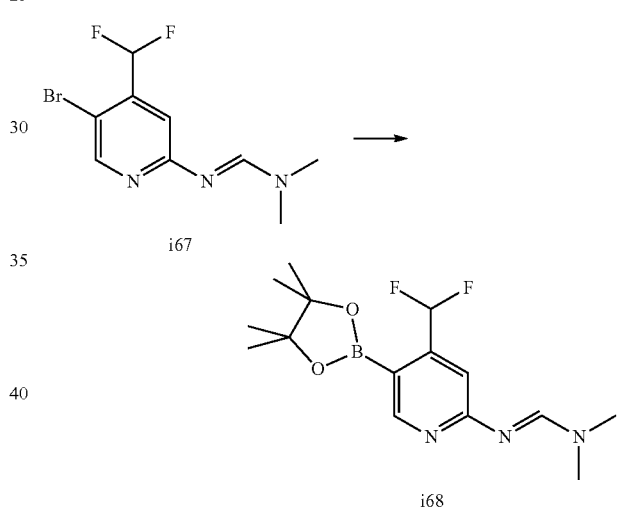

Method 21 and the synthesis of i68 was conducted as described in WO2016/075130 and in the application PCT/EP2017/025137 filed on May 17, 2017.

Method 22: 4-(difluoromethyl)pyrimidin-2-amine (i69)

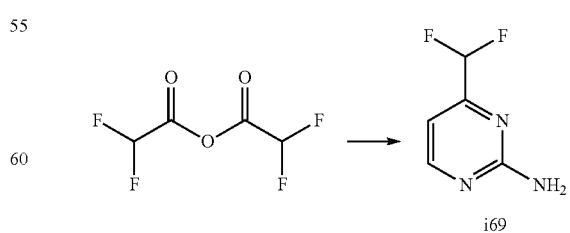

Method 22 and the synthesis of i69 was conducted as described in WO2016/075130 and in the application PCT/EP2017/025137 filed on May 17, 2017.

Method 23:
5-bromo-4-(difluoromethyl)pyrimidin-2-amine (i70)

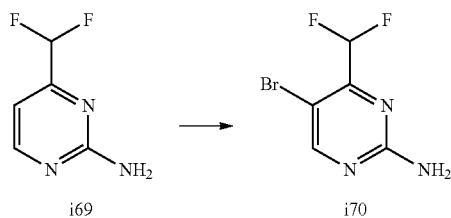 [SMILES: Nc1nccc(C(F)F)n1 ; Nc1ncc(Br)c(C(F)F)n1]

Method 23 and the synthesis of i70 was conducted as described in WO2016/075130 and in the application PCT/EP2017/025137 filed on May 17, 2017.

Method 24: N-tert-butyl carboxylate-N-(5-bromo-4-(difluoromethyl)pyrimidin-2-yl)-carbamate (i71)

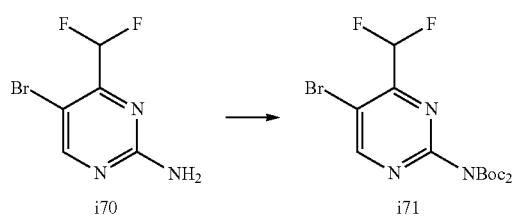

Method 24 and the synthesis of i71 was conducted as described in WO2016/075130 and in the application PCT/EP2017/025137 filed on May 17, 2017.

Method 27: tert-butyl N-tert-butoxycarbonyl-N-(5-(4-chloro-6-morpholino-1,3,5-triazin-2-yl)-4-(difluoromethyl)pyrimidin-2-yl)carbamate (i74)

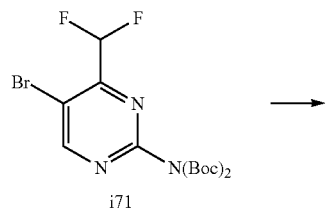

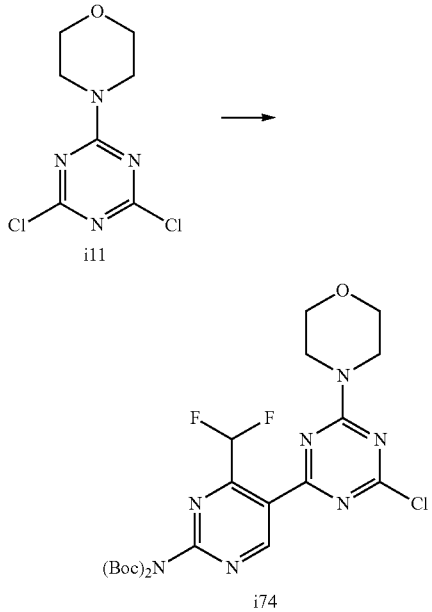

Method 27 and the synthesis of i11 and i74 was conducted as described in WO2016/075130 and in the application PCT/EP2017/025137 filed on May 17, 2017.

Method 32: (E)-4-ethoxy-1,1-difluoro-but-3-en-2-one (i83)

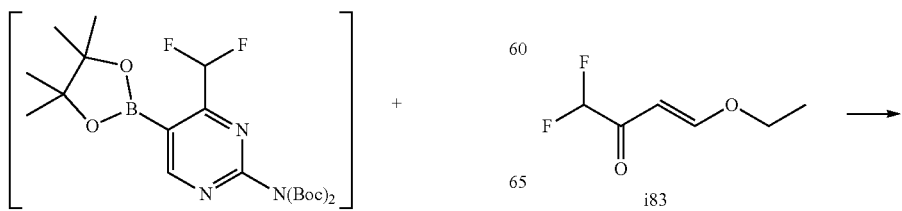

Method 32 and the synthesis of i83 was conducted as described in WO2016/075130 and in the application PCT/EP2017/025137 filed on May 17, 2017.

Method 33: (E)-3-(difluoromethyl)-5-ethoxy-3-hydroxy-pent-4-enenitrile (i84)

-continued

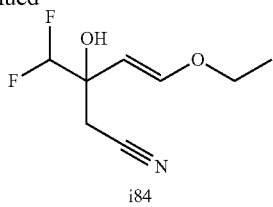

i84

Method 33 and the synthesis of i84 was conducted as described in WO2016/075130 and in the application PCT/EP2017/025137 filed on May 17, 2017.

Method 34: 4-(difluoromethyl)pyridin-2-amine (i65)

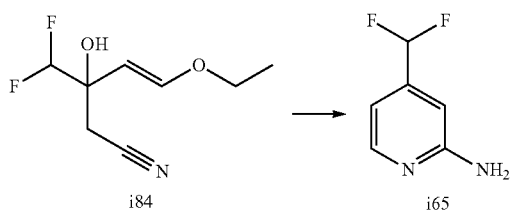

Method 34 and the synthesis of i65 was conducted as described in WO 2016/075130 and in the application PCT/EP2017/025137 filed on May 17, 2017.

Method 35: 9-[4-chloro-6-(3-oxa-9-azabicyclo[3.3.1]nonan-9-yl)-1,3,5-triazin-2-yl]-3,7-dioxa-9-azabicyclo[3.3.1]nonane (i89)

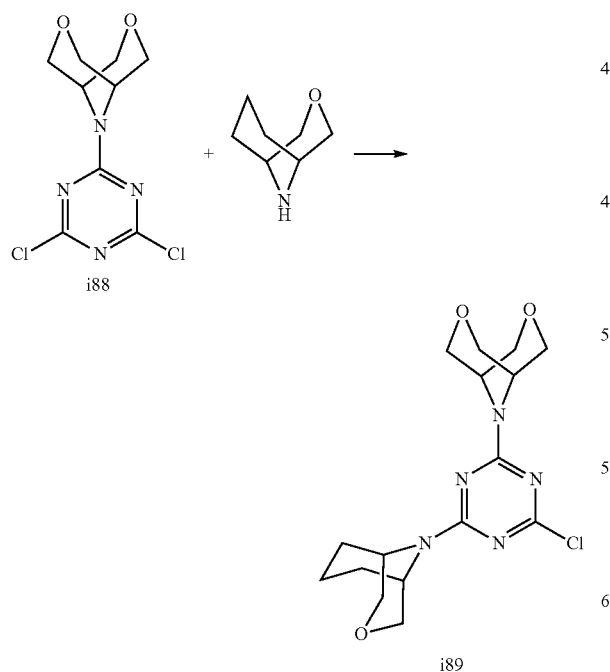

To a solution of 3-oxa-9-azabicyclo[3.3.1]nonane hydrochloride (176 mg, 1.20 mmol, 1.05 eq.) and N,N-diisopropylethylamine (0.42 mL, 2.40 mmol, 2.1 eq.) in 1,4-dioxane (5 mL) a solution of i88 (300 mg, 1.14 mmol, 1 eq.) in 1,4-dioxane (1 mL) is added. The resulting mixture is heated for 3 hours (75° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1 to 0:1) to afford the title compound i89 as a colorless solid (297 mg, 75%). $^1$H NMR (400 MHz, (CD$_3$)$_2$SO): δ4.58 (m, 1H), 4.44 (m, 1H), 4.40 (m, 1H), 4.32 (m, 1H), 4.00-3.97 (m, 4H), 3.94-3.90 (m, 2H), 3.72-3.64 (m, 6H), 2.46 (m, 1H), 1.90-1.70 (m, 4H), 1.53 (m, 1H). MS (MALDI): m/z=368.0 ([M+H]$^+$).

Preparation of Compounds of the Invention

The following general procedures were used to prepare the compounds of formula (I). Said procedures have already been described in WO2016/075130 as well as in the application PCT/EP2017/025137 filed on May 17, 2017. Therein, these procedures are numbered and referred to as well as "General Procedure 1" and "General Procedure 2" and the preparation of the exemplified and preferred compounds of formula (I) referred to compound number such as "1", "2", or the like are described in the respective same-numbered example (WO 2016/075130) or under compound number heading (PCT/EP2017/025137 filed on May 17, 2017). The preparation of the exemplified and preferred compounds of formula (I) referred to compound number such as "1*", "2*", or the like are also known to the skilled person in the art and have already been described in, inter alia, WO2010/052569 and WO2015/162084 either specifically or in analogous manner as described in the "General Procedures A-F".

General Procedure 1:

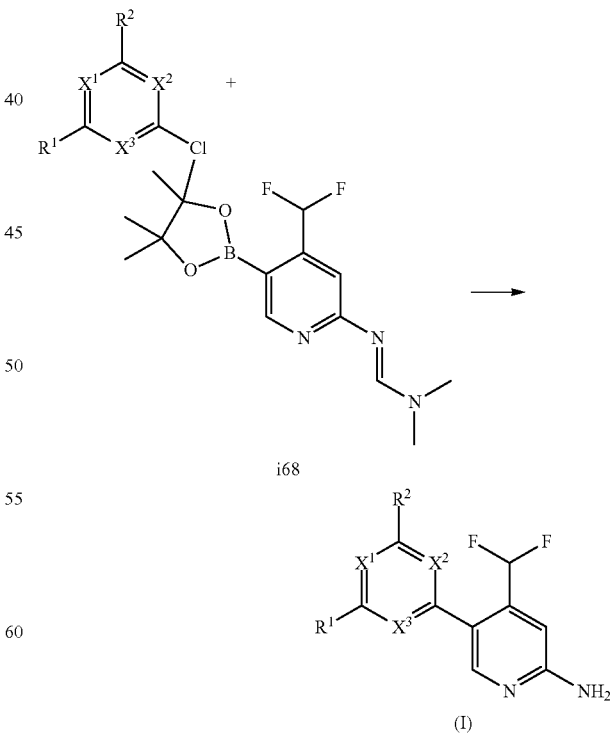

Substituted monochloro-triazine or substituted monochloro-pyrimidine (1.0 eq.), compound i68 (1.1 eq.), potassium phosphate tribasic (2.0 eq.) and chloro(2-dicyclohexylphosphino-2',4',6'-triisopropyl-1,1'-biphenyl) [2-(2'-amino-1,1'-biphenyl)]-palladium(II) (Sigma-Aldrich, product number 741825, 0.05 eq.) are charged in a flask. Under nitrogen atmosphere, 1,4-dioxane (30 volumes) and deionized water (1.5 volume) are added and the resulting mixture is then directly placed into an oil bath pre-heated at 95° C. The reaction mixture is stirred at this temperature for 2 hours. A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products of structure (I).

General Procedure 2:

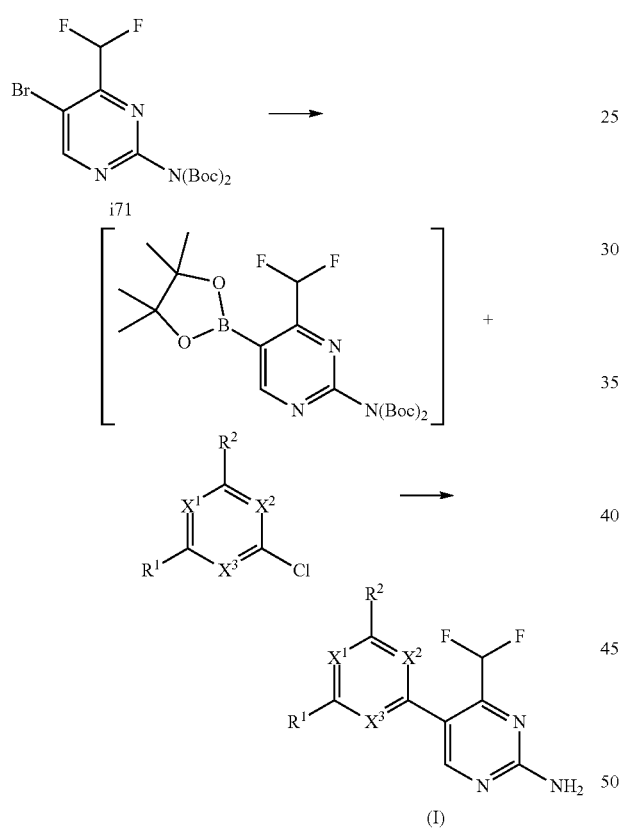

Compound i71 (1.0 eq.), 4,4,4',4',5,5,5',5'-octamethyl-2,2'-bi(1,3,2-dioxaborolane) (Manchester Organics, product number M23170, 1.5 eq.), potassium acetate (3.0 eq.) and [1,1'-bis(diphenylphosphino)-ferrocene]-dichloropalladium (II) (Sigma-Aldrich, product number 697230, 0.099 eq.) are dissolved in 1,4-dioxane (12.5 volumes) under nitrogen atmosphere. The resulting mixture is heated at 100° C. for 15 minutes (solution turned black). TLC monitoring (cyclohexane/ethyl acetate 3:1) is used to show complete consumption of starting material.

To the resulting mixture, substituted chloro-triazine or substituted chloropyrimidine (1.1 eq.), an aqueous solution of potassium carbonate (2 M, 3.0 eq.) and a previously mixed solution of triphenylphosphine (0.12 eq.) and palladium acetate (0.04 eq.) in tetrahydrofuran (100 volumes) are added. The resulting mixture is heated at 60° C. for 2 hours and subsequently allowed to cool to room temperature.

A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products.

Compound 1: 4-(difluoromethyl)-5-(4,6-dimorpholino-1,3,5-triazin-2-yl)pyridin-2-amine (1)

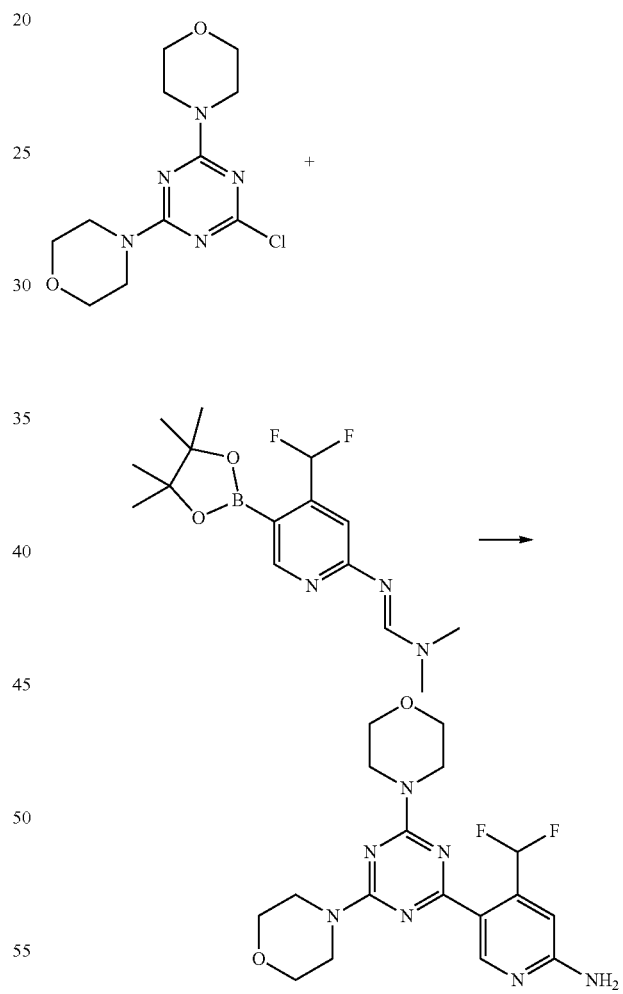

According to general procedure 1, compound 1 is obtained from starting materials i2 and i68 in 73% yield as a colorless solid.

Compound 1*: 5-(4,6-dimorpholino-1,3,5-triazin-2-yl)-4-(trifluoromethyl)pyridin-2-amine (1*) was analogously prepared as described in example 54 of WO2010/052569 and as described in WO2015/162084, respectively.

Compound 2: 4-(difluoromethyl)-5-(4,6-dimorpholino-1,3,5-triazin-2-yl)pyrimidin-2-amine (2)

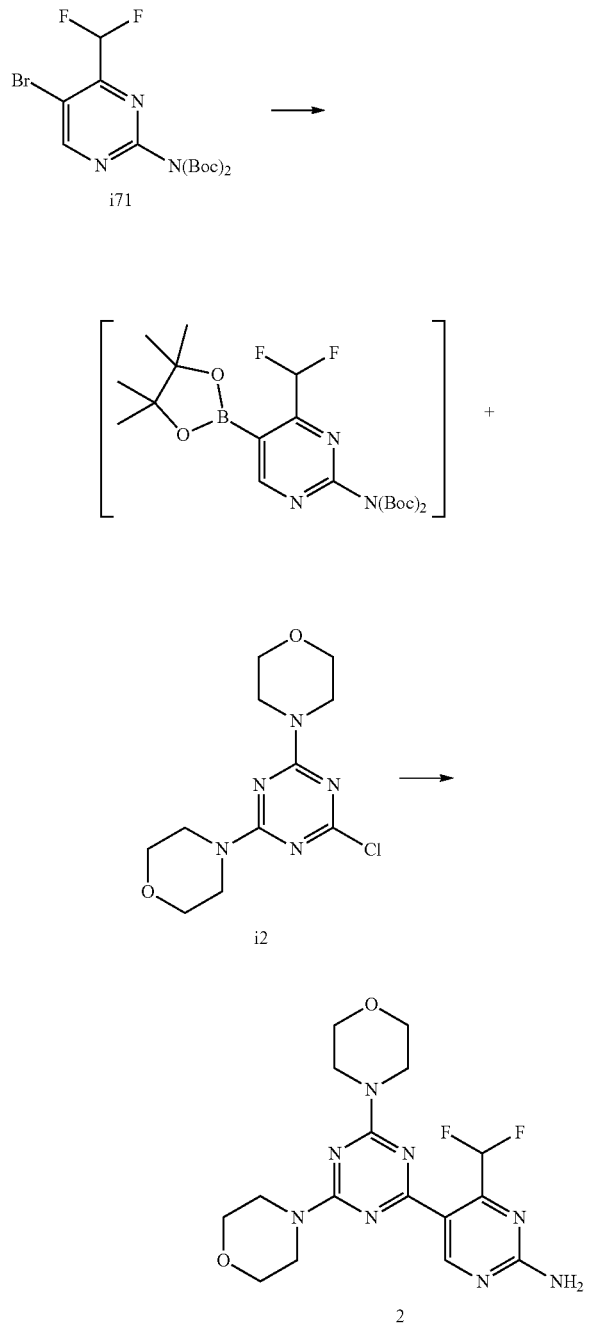

According to general procedure 2, compound 2 is obtained from starting materials i2 and i71 in 74% yield as a colorless solid.

Compound 2*: 5-(4,6-dimorpholino-1,3,5-triazin-2-yl)-4-(trifluoromethyl)pyrimidin-2-amine (2*) was analogously prepared as described in example 47 of WO2010/052569 and as described in WO2015/162084, respectively.

Compound 3, 4 and 5 were prepared as described in WO2016/075130 and in the application PCT/EP2017/025137 filed on May 17, 2017, respectively.

Compound 6: 5-(4,6-bis((S)-3-methylmorpholino)-1,3,5-triazin-2-yl)-4-(difluoromethyl)-pyridin-2-amine (6)

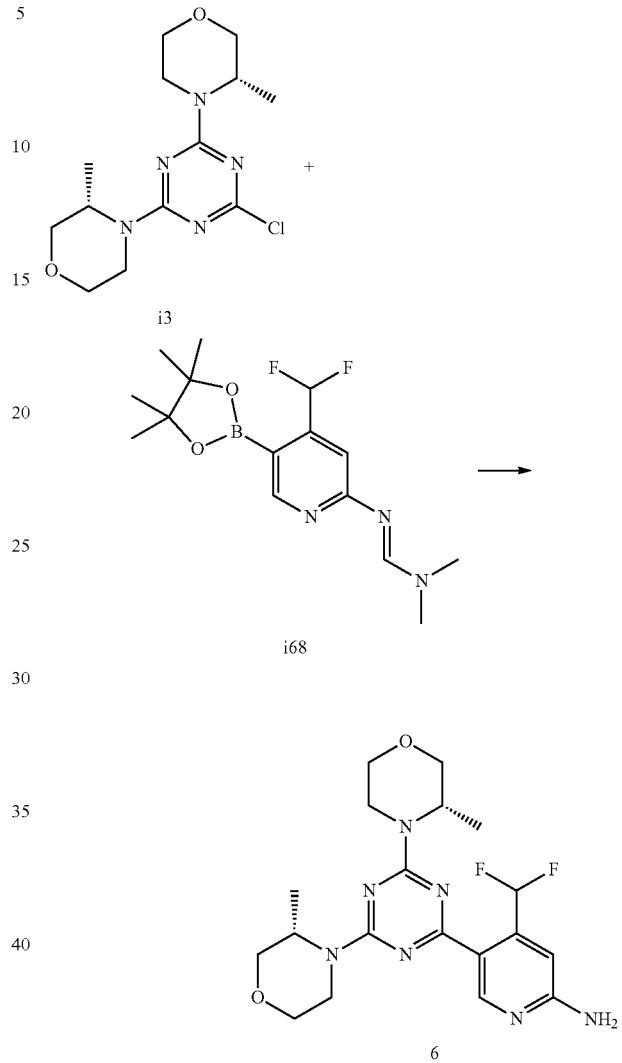

According to general procedure 1, compound 6 is obtained from starting materials i3 and i68 in 79% yield as a colorless solid.

Compound 6*: 5-[4,6-bis[(3S)-3-methylmorpholin-4-yl]-1,3,5-triazin-2-yl]-4-(trifluoro-methyl)pyridin-2-amine (6*) was analogously prepared as described in WO2010/052569 and WO2015/162084, respectively.

Compound 7: 5-(4,6-bis((S)-3-methylmorpholino)-1,3,5-triazin-2-yl)-4-(difluoromethyl)-pyrimidin-2-amine (7)

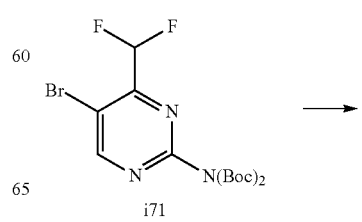

-continued

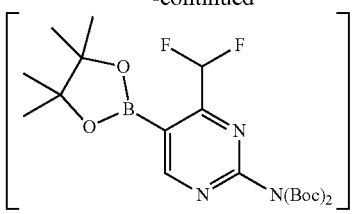

+

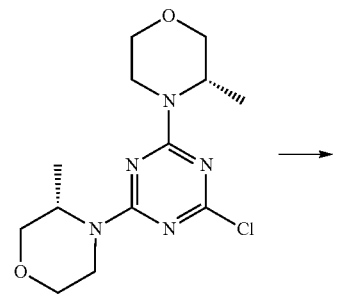
i3

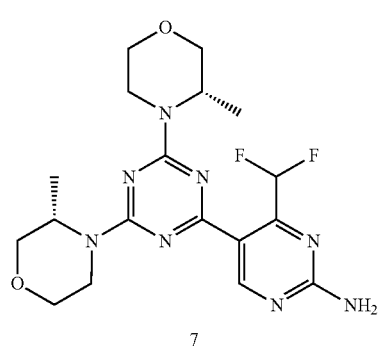
7

According to general procedure 2, compound 7 is obtained from starting materials i71 and i3 in 52% yield as a colorless solid.

Compound 7*: 5-[4,6-bis[(3S)-3-methylmorpholin-4-yl]-1,3,5-triazin-2-yl]-4-(trifluoro-methyl)pyrimidin-2-amine (7*) was analogously prepared as described in WO2010/052569 and WO2015/162084, respectively.

Compound 8: (S)-4-(difluoromethyl)-5-(4-(3-methylmorpholino)-6-morpholino-1,3,5-triazin-2-yl)pyridin-2-amine (8)

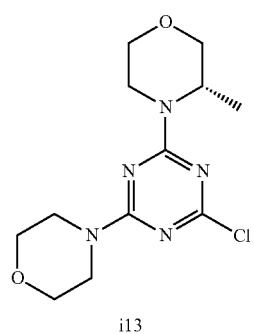
i13

+

-continued

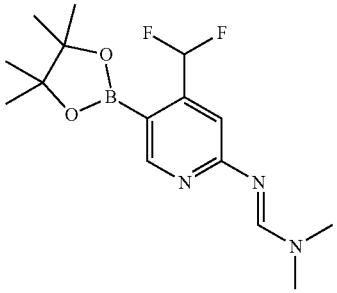
i68

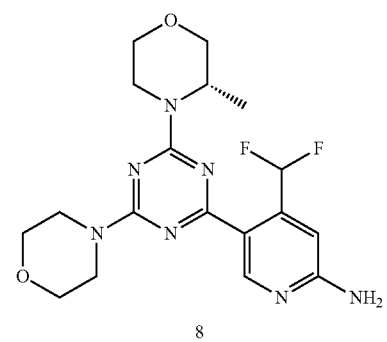
8

According to general procedure 1, compound 8 is obtained from starting materials i3 and i68 in 47% yield as a colorless solid.

Compound 8*: 5-[4-[(3S)-3-methylmorpholin-4-yl]-6-morpholino-1,3,5-triazin-2-yl]-4-(trifluoromethyl)pyridin-2-amine (8*) was analogously prepared as described in WO2010/052569 example 64 and as described in WO2015/162084, respectively.

Compound 9: (S)-4-(difluoromethyl)-5-(4-(3-methylmorpholino)-6-morpholino-1,3,5-triazin-2-yl)pyrimidin-2-amine (9)

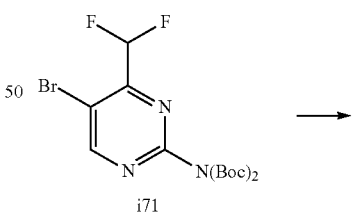
i71

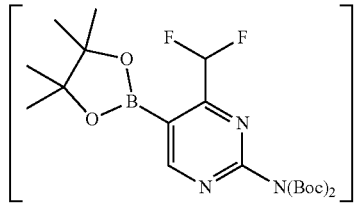

+

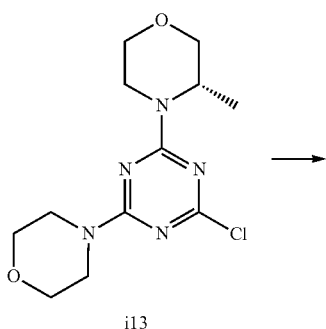

i13

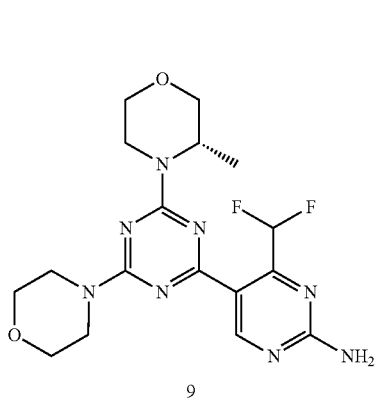

9

According to general procedure 2, compound 9 is obtained from starting materials 71 and i13 in 60% yield as a colorless solid.

Compound 9*: 5-[4-[(3S)-3-methylmorpholin-4-yl]-6-morpholino-1,3,5-triazin-2-yl]-4-(trifluoromethyl)pyrimidin-2-amine (9*) was analogously prepared as described in WO2010/052569 and WO2015/162084, respectively.

Compound 10 and 11 were prepared as described in WO2016/075130 and in the application PCT/EP2017/025137 filed on May 17, 2017, respectively.

Compound 12: 4-(difluoromethyl)-5-(4-morpholino-6-(piperazin-1-yl)-1,3,5-triazin-2-yl)pyridin-2-amine (12)

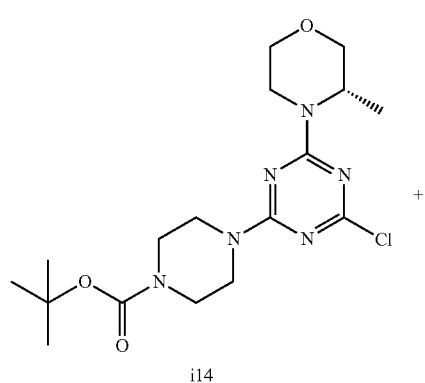

i14

+

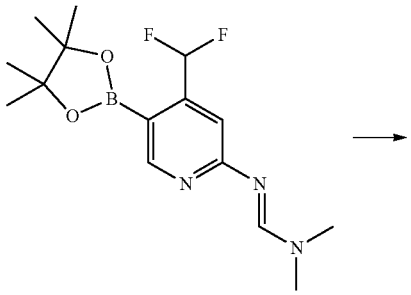

i68

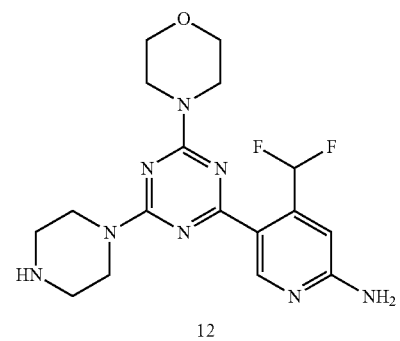

12

According to general procedure 1, compound 12 is obtained from starting materials i68 and i14 in 86% yield as a colorless solid.

Compound 12*: 5-(4-morpholino-6-piperazin-1-yl-1,3,5-triazin-2-yl)-4-(trifluoromethyl)-pyridin-2-amine (12*) was analogously prepared as described in example 57 WO2010/052569 and as described in WO2015/162084, respectively.

Compound 13: 4-(difluoromethyl)-5-(4-morpholino-6-(piperazin-1-yl)-1,3,5-triazin-2-yl)pyrimidin-2-amine (13)

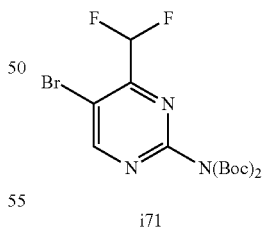

i71

+

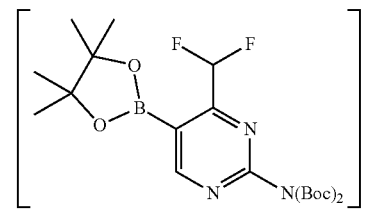

+

-continued

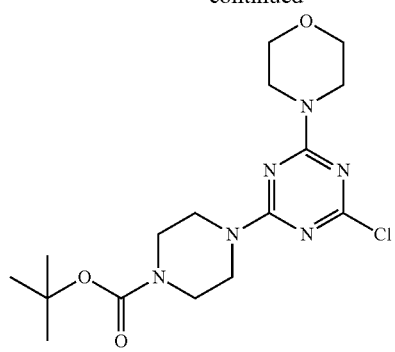

i14

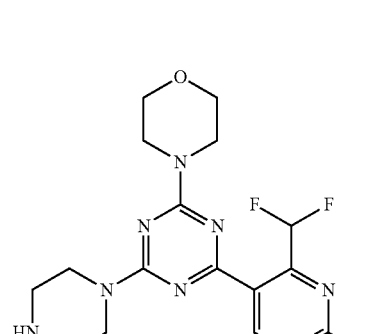

13

According to general procedure 2, compound 13 is obtained from starting materials i71 and i14 in 55% yield as a colorless solid.

Compound 13*: 5-(4-morpholino-6-piperazin-1-yl-1,3,5-triazin-2-yl)-4-(trifluoromethyl)-pyrimidin-2-amine (13*) was analogously prepared as described in example 50 WO2010/052569 and as described in WO2015/162084, respectively.

Compound 14, 15, 16, 17, 18 and 19 were prepared as described in WO2016/075130 and in the application PCT/EP2017/025137 filed on May 17, 2017, respectively.

Compound 20: 4-(difluoromethyl)-5-(4-morpholino-6-thiomorpholino-1,3,5-triazin-2-yl)-pyridin-2-amine (20)

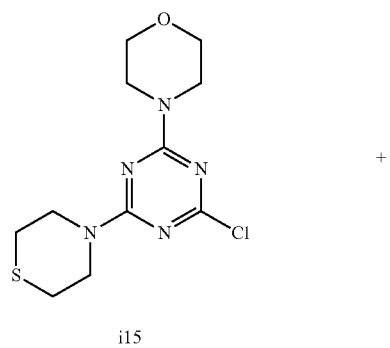

i15

+

-continued

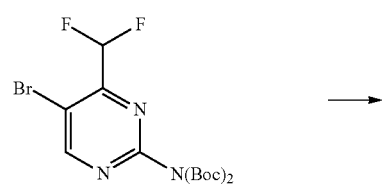

i68

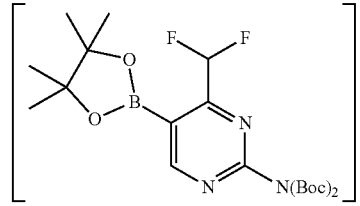

20

According to general procedure 1, compound 20 is obtained from starting materials i15 and i68 in 77% yield as a colorless solid.

Compound 20*: 5-(4-morpholino-6-thiomorpholino-1,3,5-triazin-2-yl)-4-(trifluoromethyl)-pyridin-2-amine (20*) was analogously prepared as described in WO2010/052569 and WO2015/162084, respectively.

Compound 21: 4-(difluoromethyl)-5-(4-morpholino-6-thiomorpholino-1,3,5-triazin-2-yl)-pyrimidin-2-amine (21)

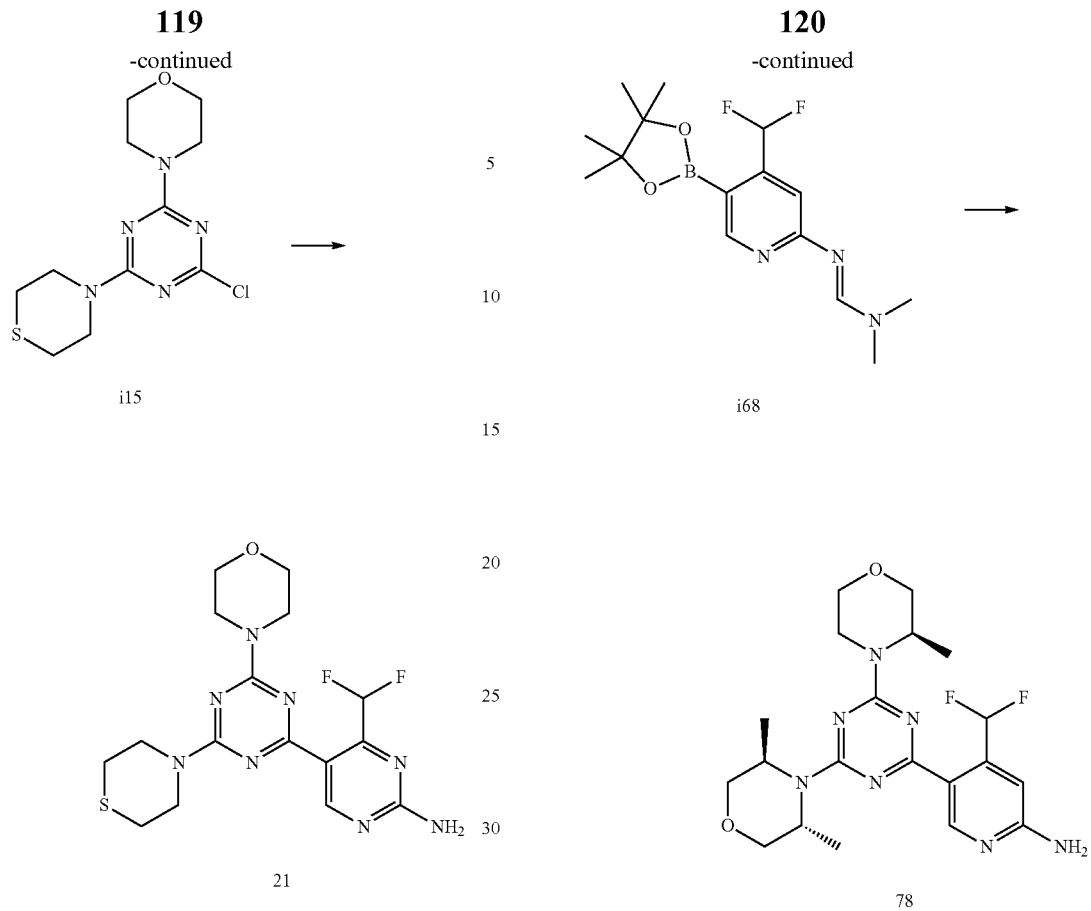

According to general procedure 2, compound 21 is obtained from starting materials i71 and i15 in 70% yield as a colorless solid.

Compound 21*: 5-(4-morpholino-6-thiomorpholino-1,3,5-triazin-2-yl)-4-(trifluoromethyl)pyrimidin-2-amine (21*) was analogously prepared as described in WO2010/052569 and WO2015/162084, respectively.

Compounds 22-77 were prepared as described in WO2016/075130 and in the application PCT/EP2017/025137 filed on May 17, 2017, respectively.

Compound 78: 4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine (78)

According to general procedure 1, compound 78 is obtained from starting materials i85 and i68 in 71% yield as a colorless solid. 1H NMR (400 MHz, (CD$_3$)$_2$SO): δ 8.90 (s, 1H), 7.82 (t, $^2J_{H,F}$=55 Hz, 1H), 6.84 (br s, 2H), 6.76 (s, 1H), 4.66 (m, 1H), 4.32 (m, 3H), 4.15-4.11 (m, 2H), 3.92 (m, 1H), 3.70 (m, 3H), 3.57 (m, 1H), 3.40 (m, 1H), 3.18 (m, 1H), 1.37 (m, 6H), 1.24 (d, $^3J_{H,H}$=6.9 Hz, 3H); $^{19}$F NMR (376 MHz, (CD$_3$)$_2$SO): δ −114.9 (br s, 2F); MS (MALDI): m/z=435.4 ([M]$^+$).

Compound 79: 4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine (79)

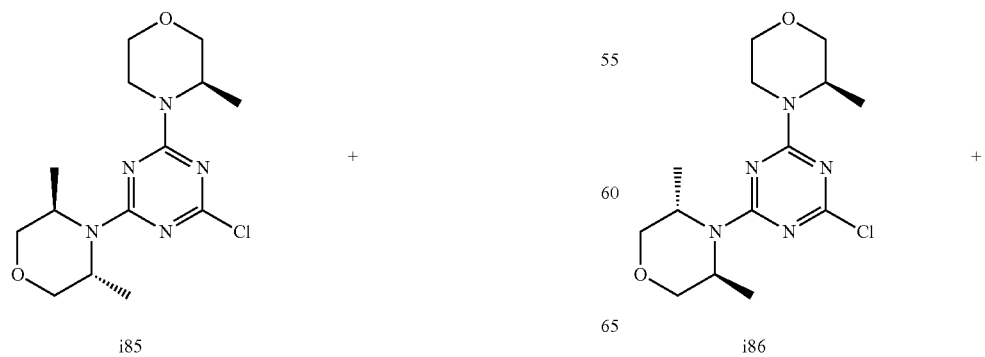

121

-continued

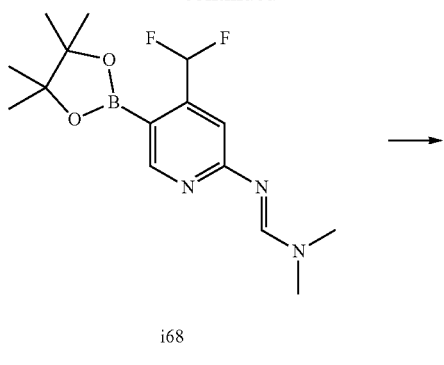

i68

→

122

-continued

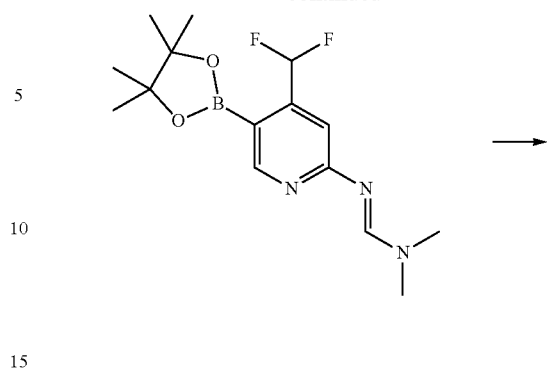

i68

→

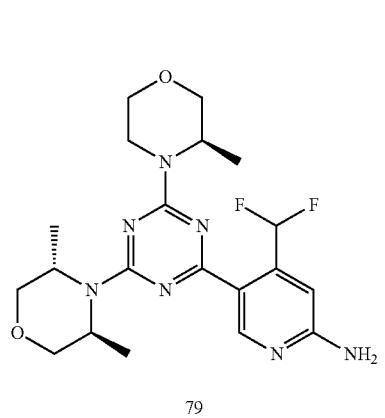

79

According to general procedure 1, compound 79 is obtained from starting materials i86 and i68 in 65% yield as a colorless solid. $^1$H NMR (400 MHz, (CD$_3$)$_2$SO): δ 8.91 (s, 1H), 7.82 (t, $^2J_{H,F}$=55 Hz, 1H), 6.85 (br s, 2H), 6.76 (s, 1H), 4.66 (m, 1H), 4.32 (m, 3H), 4.15-4.11 (m, 2H), 3.92 (m, 1H), 3.70 (m, 3H), 3.57 (m, 1H), 3.40 (m, 1H), 3.19 (m, 1H), 1.37 (m, 6H), 1.24 (d, $^3J_{H,H}$=6.9 Hz, 3H); $^{19}$F NMR (376 MHz, (CD$_3$)$_2$SO): δ −114.9 (br s, 2 F); MS (MALDI): m/z=434.3 ([M]$^+$).

Compound 80: 4-(difluoromethyl)-5-[4-morpholino-6-(3-oxa-9-azabicyclo[3.3.1]nonan-9-yl)-1,3,5-triazin-2-yl]pyridin-2-amine (80)

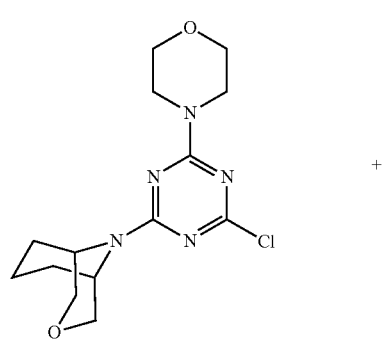

+

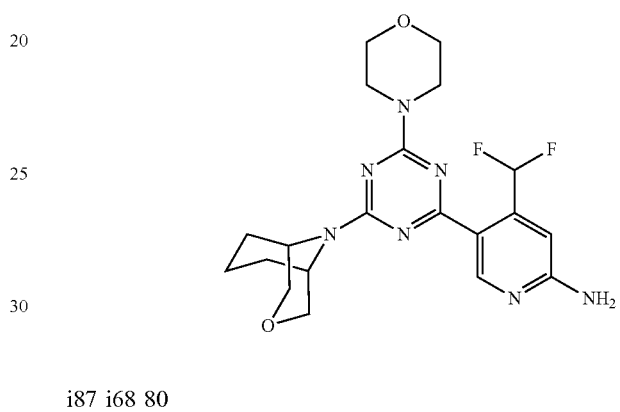

i87 i68 80

According to general procedure 1, compound 80 is obtained from starting materials i87 and i68 in 57% yield as a colorless solid. $^1$H NMR (400 MHz, (CD$_3$)$_2$SO): δ 8.85 (s, 1H), 7.73 (t, $^2J_{H,F}$=55 Hz, 1H), 6.84 (br s, 2H), 6.75 (s, 1H), 4.61-4.57 (m, 2H), 3.95 (m, 2H), 3.75-3.65 (m, 10H), 2.48 (m, 1H), 1.88-1.72 (m, 4H), 1.57 (m, 1H); $^{19}$F NMR (376 MHz, (CD$_3$)$_2$SO): δ −115.4 (m, 2F); MS (MALDI): m/z=434.3 ([M+H]$^+$).

Compound 82: 4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine (82)

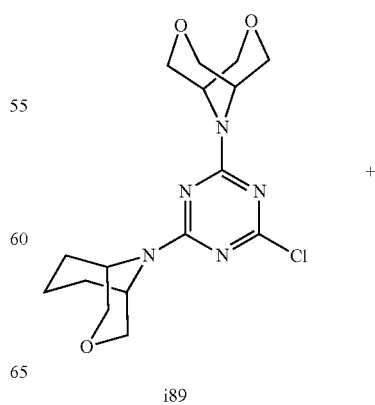

+ i89

123

-continued

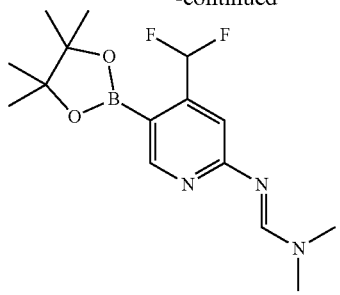

i68

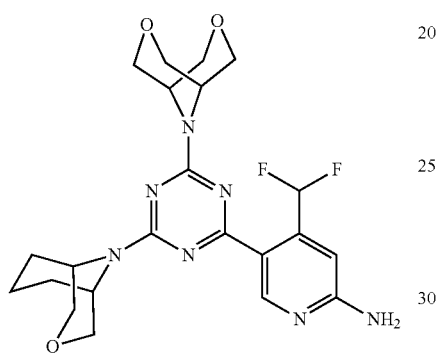

82

According to general procedure 1, compound 82 is obtained from starting materials i89 and i68 in 51% yield as a colorless solid. $^1$H NMR (400 MHz, (CD$_3$)$_2$SO): δ 8.84 (s, 1H), 7.70 (t, $^2J_{H,F}$=55 Hz, 1H), 6.85 (br s, 2H), 6.75 (s, 1H), 4.62 (m, 1H), 4.54 (m, 1H), 4.52 (m, 1H), 4.44 (m, 1H), 4.04-3.92 (m, 6H), 3.75-3.62 (m, 6H), 2.45 (m, 1H), 1.89-1.75 (m, 4H), 1.57 (m, 1H); $^{19}$F NMR (376 MHz, (CD$_3$)$_2$SO): δ −115.7 (m, 2F); MS (MALDI): m/z=476.2 ([M+H]$^+$).

Compound 83: 5-[4,6-bis[(3S,5S)-3,5-dimethylmorpholin-4-yl]-1,3,5-triazin-2-yl]-4-(difluoromethyl)pyridin-2-amine (83)

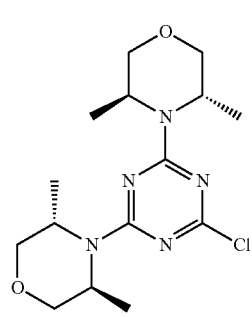

i90

124

-continued

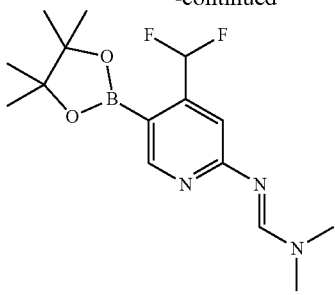

i68

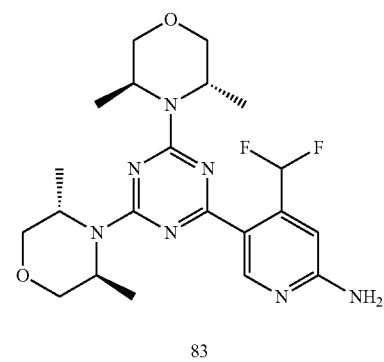

83

According to general procedure 1, compound 83 is obtained from starting materials i90 and i68 in 56% yield as a colorless solid. $^1$H NMR (400 MHz, (CD$_3$)$_2$SO): δ 8.92 (s, 1H), 7.87 (t, $^2J_{H,F}$=55 Hz, 1H), 6.84 (br s, 2H), 6.77 (s, 1H), 4.32 (m, 4H), 4.14 (m, 4H), 3.70 (m, 4H), 1.39 (d, $^3J_{H,H}$=6.9 Hz, 12H); $^{19}$F NMR (376 MHz, (CD$_3$)$_2$SO): δ −115.5 (br s, 2 F); MS (MALDI): m/z=448.3 ([M]$^+$).

Compound 84: 4-(difluoromethyl)-5-[4-(3,7-dioxa-9-azabicyclo[3.3.1]nonan-9-yl)-6-morpholino-1,3,5-triazin-2-yl]pyridin-2-amine (84)

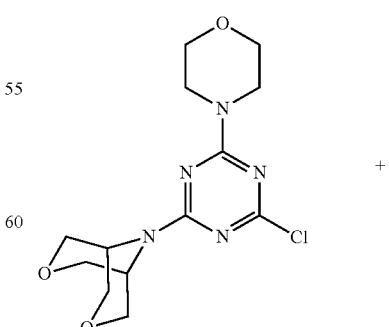

i91

125
-continued

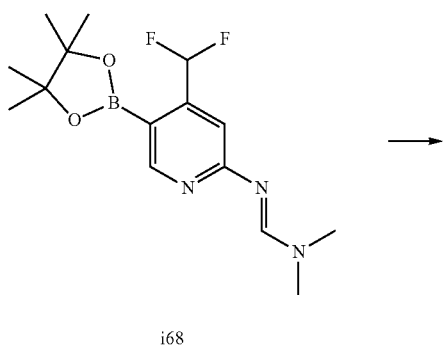

i68

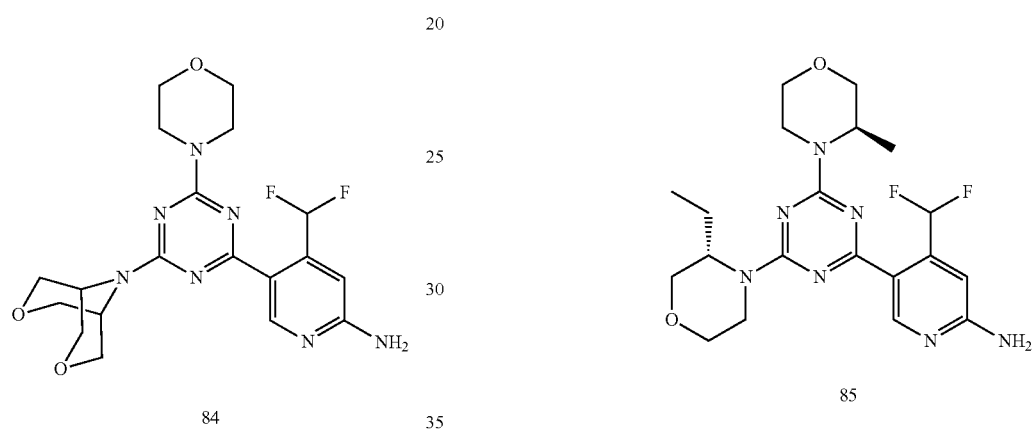

84

According to general procedure 1, compound 84 is obtained from starting materials i91 and i68 in 63% yield as a colorless solid. $^1$H NMR (400 MHz, (CD$_3$)$_2$SO): δ 8.86 (s, 1H), 7.71 (t, $^2J_{H,F}$=55 Hz, 1H), 6.87 (br s, 2H), 6.75 (s, 1H), 4.49 (m, 2H), 4.02 (m, 4H), 3.74-3.65 (m, 12H); $^{19}$F NMR (376 MHz, (CD$_3$)$_2$SO): δ −115.6 (br s, 2 F); MS (MALDI): m/z=436.4 ([M+H]$^+$).

Compound 85: 4-(difluoromethyl)-5-[4-[(3S)-3-ethylmorpholin-4-yl]-6-[(3R)-3-methylmorpholin-4-yl]-1,3,5-triazin-2-yl]pyridin-2-amine (85)

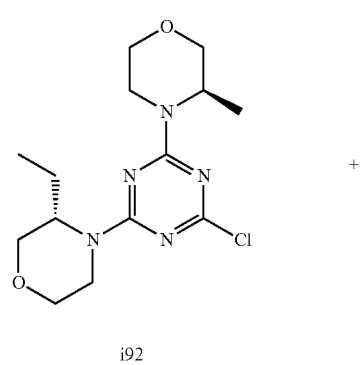

i92

126
-continued

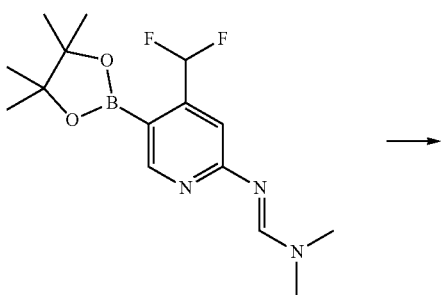

i68

85

According to general procedure 1, compound 85 is obtained from starting materials i92 and i68 in 52% yield as a colorless solid. $^1$H NMR (400 MHz, (CD$_3$)$_2$SO): δ 8.88 (s, 1H), 7.77 (t, $^2J_{H,F}$=55 Hz, 1H), 6.85 (br s, 2H), 6.76 (s, 1H), 4.70-4.25 (m, 4H), 3.90 (m, 3H), 3.72 (m, 1H), 3.60-3.45 (m, 4H), 3.16 (m, 2H), 1.73 (m, 2H), 1.22 (d, $^3J_{H,H}$=6.9 Hz, 3H), 0.86 (m, 3H); $^{19}$F NMR (376 MHz, (CD$_3$)$_2$SO): δ −114.9 (br s, 2 F); MS (MALDI): m/z=436.9 ([M+H]$^+$).

Compound 86: 4-(difluoromethyl)-5-[4-[(3R)-3-ethylmorpholin-4-yl]-6-[(3R)-3-methylmorpholin-4-yl]-1,3,5-triazin-2-yl]pyridin-2-amine (86)

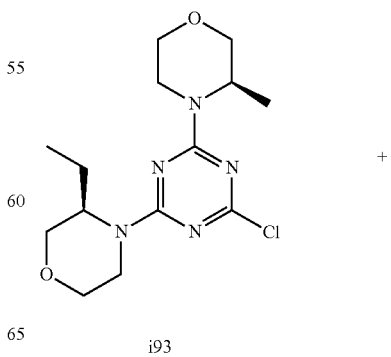

i93

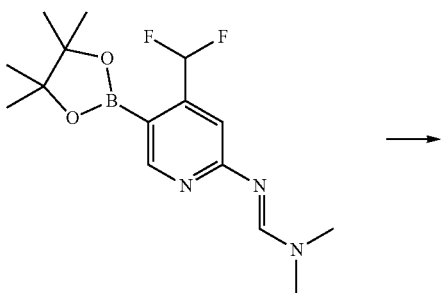

i68

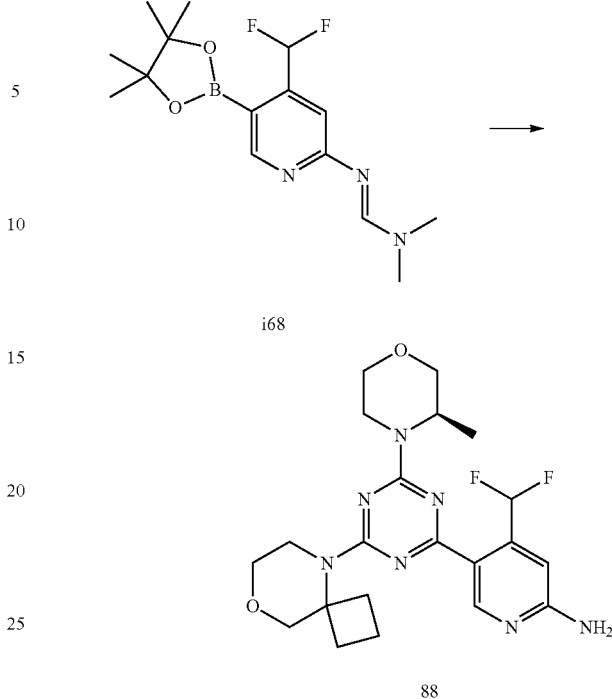

i68

86

According to general procedure 1, compound 86 is obtained from starting materials i93 and i68 in 47% yield as a colorless solid. $^1$H NMR (400 MHz, (CD$_3$)$_2$SO): δ 8.88 (s, 1H), 7.77 (t, $^2J_{H,F}$=55 Hz, 1H), 6.85 (br s, 2H), 6.76 (s, 1H), 4.65 (m, 1H), 4.49-4.30 (m, 3H), 3.93-3.82 (m, 3H), 3.72 (m, 1H), 3.57 (m, 1H), 3.50 (m, 1H), 3.43-3.37 (m, 2H), 3.19-3.14 (m, 2H), 1.73 (m, 2H), 1.22 (d, $^3J_{H,H}$=6.9 Hz, 3H), 0.86 (m, 3H); $^{19}$F NMR (376 MHz, (CD$_3$)$_2$SO): δ −115.3 (br s, 2 F); MS (MALDI): m/z=436.9 ([M+H]$^+$).

Compound 88: 4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine (88)

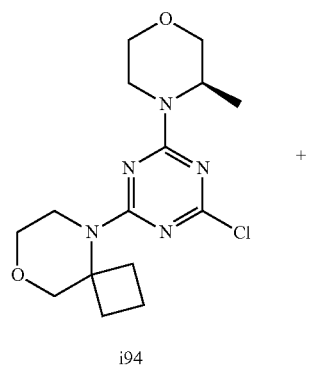

i94

88

According to general procedure 1, compound 88 is obtained from starting materials i94 and i68 in 50% yield as a colorless solid. $^1$H NMR (400 MHz, (CD$_3$)$_2$SO): δ 8.82 (s, 1H), 7.71 (t, $^2J_{H,F}$=55 Hz, 1H), 6.84 (br s, 2H), 6.75 (s, 1H), 4.55 (m, 1H), 4.23 (m, 1H), 3.91 (m, 1H), 3.78 (m, 2H), 3.69 (m, 3H), 3.56 (m, 1H), 3.50 (m, 2H), 3.41 (m, 1H), 3.16 (m, 1H), 2.50 (m, 2H), 2.26 (m, 2H), 1.73 (m, 2H), 1.21 (d, $^3J_{H,H}$=6.9 Hz, 3H); $^{19}$F NMR (376 MHz, (CD$_3$)$_2$SO): δ −114.9 (br s, 2 F); MS (MALDI): m/z=446.8 ([M+H]+).

Example 2

In Vitro mTOR Binding Assay and in-Cell Western Blot

In Vitro mTOR Binding Assay

N-terminally GST-tagged mTOR (Cat. No. PR8683B; 0.45 mg/ml; truncated version: amino acids 1360-2549), Alexa Fluor® 647 labeled kinase Tracer 314 (Cat. No. PV6087), LanthaScreen Eu-anti-GST Tag antibody (Cat. No. PV5594) were purchased from Life Technologies. The 1×mTOR Kinase Buffer consists of 50 mM HEPES pH 7.5, 5 mM MgCl$_2$, 1 mM EGTA, and 0.01% Pluronic F-127 (Sigma Cat. No. P2443-250G).

A 10-point 4-fold serial dilution (highest concentration at 10 μmol/L and lowest concentration at 40 pmol/L) of each compound was tested for mTOR binding in duplicate in a 384-well plate. To perform the LanthaScreen kinase binding assay 5 μl of the test compounds concentrated 3× the final concentration, 5 μl of 9 nM GST-mTOR/6 nM Eu-anti-GST antibody mixture and 5 μl of 30 nM Tracer 314 solution were mixed together resulting to a final concentration of 3 nM GST-mTOR, 2 nM Eu-anti-GST antibody and 10 nM Tracer 314 per well. After 30 min incubation at RT, time-resolved FRET was measured with a Synergy 4 multi-mode microplate reader (Biotek Instruments) using the following settings: 100 microsecs delay before data collection, 200 microsecs time for data collection, 10 measurements per data point. Emission filter: 665 nm/8 nm with sensitivity set to 190 and 620 nm/10 nm with sensitivity set to 130; Excitation filter: 340 nm/30 nm; Dichroic mirror 400 nm.

For data analysis, the mean background (wells with only mTOR kinase buffer) was subtracted and the emission ratio calculated by dividing the signal emitted at 665 nm from the acceptor (Alexa Fluor® 647 labeled Tracer 314) by the signal emitted at 620 nm from the donor (Eu-labeled antibody). $IC_{50}$ values of each compound were determined by plotting the emission ratio versus the compound concentrations (in logarithmic scale) and then by fitting a sigmoidal dose-response curve with variable slope to the data using GraphPad™ Prism.

In-Cell Western Blot

A2058 cells are plated at 20,000 cells/well in a 96-well plate (Perkin Elmer, Cat. No. 6005558) and 24 hours later treated with different compounds for 1 hour. For each compound 7 different concentrations are applied on cells (5 µM, 1.25 µM, 0.625 µM, 0.3125 µM, 0.155 µM, 0.08 µM and 0.04 µM). Cells are fixed with 4% paraformaldehyde for 30 minutes at room temperature, washed 2 times with 1% BSA in PBS, permeabilized with 0.1% Triton X-100 in PBS/1% BSA for 30 minutes at room temperature and blocked with 5% goat serum in PBS/1% BSA/0.1% Triton X-100 for 30 minutes at room temperature. Cells are stained with primary antibody either with rabbit anti-pPKB S473 (1:500; Cell Signaling Technology, Cat. No. 4058) combined with mouse anti-α-tubulin (1:2000; used for normalization; Sigma, Cat. No. T9026) or with rabbit anti-pS6 S235/S236 (1:500; Cell Signaling Technology, Cat. No. 4856) combined with mouse anti-α-tubulin (1:2000; used for normalization) over night at 4° C. After 3 times 5 minutes wash with PBS/1% BSA/0.1% triton cells are treated with the secondary antibodies goat-anti-mouse IRDye680 (LICOR, Cat. No. 926-68070) and goat-anti-rabbit IRDye800 (LICOR, 926-32211) (each diluted 1:500 in PBS/1% BSA/0.1% triton) for 1 hour while shaking in the dark. Cells are washed 3 times 5 minutes with PBS/1% BSA/0.1% triton and plate scanned with the Odyssey Infrared Scanning system using both 700 and 800 nm channels. As control for 0% inhibition vehicle (0.2% DMSO) is added to cells. To correct for background staining in the data analysis wells are treated only with secondary antibodies.

For data analysis the mean background signal from channel 700 nm and 800 nm are subtracted from each signal in channel 700 nm and 800 nm, respectively. The signals in each channel are normalized to the 0% inhibition and then signal ratio 800 nm over 700 nm is performed to obtain the values for either pPKB S473 or pS6 S235/S236 normalized to α-Tubulin.

$IC_{50}$ values of each compound are determined by plotting the normalized pPBK S473 and pS6 S235/S236 signals, respectively, versus the compound concentrations (in logarithmic scale) and then by fitting a sigmoidal dose-response curve with variable slope to the data using GraphPad™ Prism.

TABLE 1

| Comparative biological activities | | | | | |
|---|---|---|---|---|---|
| | Compound 1 | Compound 1* | Reference BKM 120 | Compound 2 | Compound 2* |
| pPKB S473 $IC_{50}$ [nM] | 108 | 149 | 390 | 34 | 64 |
| pS6 S235/236 $IC_{50}$ [nM] | 196 | 340 | 640 | 80 | 650 |
| mTOR $IC_{50}$ [nM] | 8 | 190 | 250 | 59 | 199 |

TABLE 2

Comparative biological activities

| | Compound 6 | Compound 6* | Compound 7 | Compound 7* |
|---|---|---|---|---|
| pPKB S473 IC$_{50}$ [nM] | 155 | 255 | 59 | 118 |
| pS6 S235/236 IC$_{50}$ [nM] | 215 | 433 | 97 | 224 |
| mTOR IC$_{50}$ [nM] | 23 | nd | 71 | nd |

TABLE 3

Comparative biological activities

| | Compound 8 | Compound 8* | Compound 9 | Compound 9* |
|---|---|---|---|---|
| pPKB S473 IC$_{50}$ [nM] | 74 | 196 | 35 | 91 |
| pS6 S235/236 IC$_{50}$ [nM] | 68 | 90 | 72 | 164 |
| mTOR IC$_{50}$ [nM] | 10 | nd | 24 | nd |

TABLE 4

Comparative biological activities

| | Compound 12 | Compound 12* | Compound 13 | Compound 13* |
|---|---|---|---|---|
| pPKB S473 IC$_{50}$ [nM] | 208 | 302 | 43 | 116 |
| pS6 S235/236 IC$_{50}$ [nM] | 515 | 743 | 150 | 416 |
| mTOR IC$_{50}$ [nM] | 543 | 796 | 1015 | 2834 |

TABLE 5

Comparative biological activities

| | Compound 16 | WO2007/084786 | Compound 17 | WO2007/084786 |
|---|---|---|---|---|
| pPKB S473 IC$_{50}$ [nM] | 207 | 263 | 90 | 194 |
| pS6 S235/236 IC$_{50}$ [nM] | 184 | 277 | 149 | 384 |
| mTOR IC$_{50}$ [nM] | 30 | 179 | 155 | 644 |

TABLE 6

Comparative biological activities

| | Compound 18 | WO2008/098058 | Compound 19 | WO2008/098058 |
|---|---|---|---|---|
| pPKB S473 IC$_{50}$ [nM] | 243 | 555 | 78 | 175 |
| pS6 S235/236 IC$_{50}$ [nM] | 256 | 665 | 147 | 370 |
| mTOR IC$_{50}$ [nM] | 31 | 366 | 158 | 1925 |

TABLE 7

Comparative biological activities

| | Compound 20 | Compound 20* | Compound 21 | Compound 21* |
|---|---|---|---|---|
| pPKB S473 IC$_{50}$ [nM] | 146 | 311 | 57 | 343 |
| pS6 S235/236 IC$_{50}$ [nM] | 250 | 559 | 216 | 996 |
| mTOR IC$_{50}$ [nM] | 13 | 118 | 54 | 394 |

TABLE 8

Comparative biological activities

| | Compound 25 | WO2007/084786 | Compound 26 | WO2007/084786 |
|---|---|---|---|---|
| pPKB S473 IC$_{50}$ [nM] | 303 | 452 | 87 | 193 |
| pS6 S235/236 IC$_{50}$ [nM] | 294 | 553 | 191 | 617 |
| mTOR IC$_{50}$ [nM] | 32 | 152 | 47 | 287 |

TABLE 9

Comparative biological activities

| | Compound 27 | WO2007/084786 | Compound 28 | WO2007/084786 |
|---|---|---|---|---|
| pPKB S473 IC$_{50}$ [nM] | 614 | 883 | 77 | 290 |
| pS6 S235/236 IC$_{50}$ [nM] | 766 | 1100 | 146 | 1027 |
| mTOR IC$_{50}$ [nM] | 65 | 376 | 23 | 1253 |

TABLE 10

Comparative biological activities

| | Compound 23 | WO2007/084786 | Compound 24 | WO2007/084786 |
|---|---|---|---|---|
| pPKB S473 IC$_{50}$ [nM] | 285 | 564 | 84 | 340 |
| pS6 S235/236 IC$_{50}$ [nM] | 230 | 562 | 167 | 740 |
| mTOR IC$_{50}$ [nM] | 40 | 88 | 35 | 121 |

TABLE 11

Comparative biological activities

| | Compound 31 | WO2007/084786 | Compound 32 | WO2007/084786 |
|---|---|---|---|---|
| pPKB S473 IC$_{50}$ [nM] | 146 | 248 | 100 | 191 |
| pS6 S235/236 IC$_{50}$ [nM] | 124 | 228 | 387 | 535 |
| mTOR IC$_{50}$ [nM] | 15 | 28 | 293 | 186 |

TABLE 12

Results of in-cell Western Blot and mTOR binding

| | In-cell Western blot | | binding |
|---|---|---|---|
| Compound | pPKB S473 - IC$_{50}$ [nM] | pS6 S235/S236 - IC$_{50}$ [nM] | mTOR - IC$_{50}$ [nM] |
| Reference BKM120 | 390 | 640 | 250 |
| 1* | 149 | 340 | 190 |
| 1 | 108 | 196 | 8 |
| 2 | 34 | 80 | 59 |
| 3 | 231 | 105 | 8 |
| 4 | 178 | 135 | nd |
| 5 | 85 | 135 | nd |
| 6 | 155 | 215 | 23 |
| 7 | 59 | 97 | 71 |
| 8 | 74 | 68 | 10 |
| 9 | 35 | 72 | 24 |

TABLE 12-continued

Results of in-cell Western Blot and mTOR binding

| Compound | In-cell Western blot pPKB S473 - IC$_{50}$ [nM] | pS6 S235/S236 - IC$_{50}$ [nM] | binding mTOR - IC$_{50}$ [nM] |
|---|---|---|---|
| 10 | 138 | 93 | nd |
| 11 | 61 | 96 | nd |
| 12 | 219 | 407 | 543 |
| 13 | 37 | 120 | 1015 |
| 14 | 349.5 | 883 | nd |
| 15 | 49 | 286 | nd |
| 16 | 207 | 184 | 30 |
| 17 | 90 | 149 | 155 |
| 18 | 243 | 256 | 31 |
| 19 | 78 | 147 | 158 |
| 20 | 146 | 250 | 13 |
| 21 | 57 | 216 | 54 |
| 22 | 57 | 216 | 18 |
| 23 | 285 | 230 | 40 |
| 24 | 84 | 167 | 35 |
| 25 | 303 | 294 | 32 |
| 26 | 87 | 191 | 47 |
| 27 | 614 | 766 | 65 |
| 28 | 77 | 146 | 23 |
| 31 | 146 | 124 | 15 |
| 32 | 100 | 387 | 293 |
| 37 | 533 | 268 | 49 |
| 38 | 219 | 79 | nd |
| 39 | 106 | 47 | 1 |
| 40 | 252 | 160 | 5 |
| 41 | 436 | 261 | 22 |
| 42 | 54 | 45 | 3 |
| 44 | 197 | 87 | 5 |
| 45 | 234 | 93 | 7 |
| 46 | 956 | 426 | 36 |
| 47 | 469 | 176 | 29 |
| 50 | 1561 | 407 | nd |
| 51 | 875 | 352 | nd |
| 52 | 1050 | 332 | nd |
| 53 | 1318 | 612 | nd |
| 54 | 354 | 209 | nd |
| 55 | 942 | 526 | nd |
| 56 | >10000 | >10000 | nd |
| 66 | 244 | 139 | 4 |
| 67 | 787 | 395 | nd |
| 68 | 682 | 415 | nd |
| 69 | 244 | 140 | 21 |
| 70 | 914 | 906 | nd |
| 71 | 2337 | 3141 | nd |
| 77 | 476 | | nd |
| 78 | 506 | 392 | 38 |
| 79 | 200 | 136 | 10 |
| 80 | 94 | 117 | nd |
| 82 | 329 | 169 | 40 |
| 83 | 379 | 294 | 32 |
| 84 | 116 | 146 | nd |
| 85 | 249 | 241 | nd |
| 86 | 231 | 236 | nd |
| 88 | 271 | 192 | 18 |

Example 3

A: Kinase Binding

In order to test binding of 1* to PI3K isoforms and related kinases, a biochemical assay was performed at DiscoveRx (Fremont, USA) (Table 13, Rows 1-7).

B: Kinase Inhibition

Furthermore, compound 1* and reference compounds were analyzed for their ability to inhibit kinase function of PIK3CA and related kinases (Proqinase, Germany) (Column3 of Table 13). Lipid kinases PIK3CA, PIK3CB, PIK3CG, PIK3CD, (PI3K α, β, γ and δδ), PIK3C$_2$A, PIK3C$_2$B, PIK3C$_2$G, PIK3C$_3$, PIK4B were tested in an ADP-Glo assay (Promega, USA). Protein kinases mTOR and DNAPK were tested in a radiometric $^{33}$P-γATP assay ($^{33}$PanQinase® Activity Assay, Proqinase, Germany). IC$_{50}$ values were measured by testing 10 semi-log concentrations of each compound in the range from 1×10-04 M to 3×10-09 M, in singlicate. Prior to testing, the compounds dissolved to 1×10-02M stock solutions in volumes of 100% DMSO as stated in the compound submission form (CSF). 100 1l of each stock solution were transferred into column 2 of a microtiter plate. Subsequently, the 1×10-02 M stock solutions in column 2 of the master plate were subjected to a serial, semi-logarithmic dilution using 100% DMSO as a solvent. This resulted in 10 distinct concentrations, with a dilution endpoint of 3×10-07 M/100% DMSO. Pure DMSO was used as control. Compounds were diluted with water and then transferred into the assay resulting in a 1% DMSO solution in a concentration range of 1×10-04 M to 3×10-09 M.

For measuring lipid kinase inhibition, assays were performed in 96-well half-area microtiter plates. The following solutions were mixed and incubated for 30° C. for 40 minutes: 10 µl of ATP solution (50 mM HEPES-NaOH, pH 7.5, 1 mM EGTA, 100 mM NaCl, 0.03% CHAPS, 2 mM DTT, ATP (PIK3C$_3$, 20 µM; PIK3CA, 150 µM, PIK3CB 300 µM, PIK3CG 500 µM, PIK3CG 100 µM), kinase (PK3C$_3$, 25 ng/25 µl; PIK3CA, 2 25 ng/25 µl, PIK3CB 10 25 ng/25 µl, PIK3CG 5 25 ng/25p, PIK3CG 40 25 ng/25 µl) and substrate (50 or 100 µM, respectively), 5 µl of test sample in 5% DMSO and 10 µl of enzyme/substrate mixture. The assay for PIK3C3 additionally contained 3 mM MnCl2, the assay for PIK3CA/PIK3R1, PIK3CB/PIK3R1, PIK3CD/PIK3R1 and PIK3CG additionally contained 3 mM MgCl2. 50 µl kinase detection reagent per well was added followed by an incubation for further 60 minutes at room temperature. Signal was measured with a microplate reader (Victor2, Perkin Elmer, Boston, Ma, USA), in luminescence mode.

For measuring protein kinase activity, the reaction mixture was pipetted into a 96 well plate in four steps in the following order: 20 µl of assay buffer, 5 µl of ATP solution (in H2O), 5 µl of test compound (in 10% DMSO), 20 µl enzyme/substrate mix. The assay for all protein kinases contained 70 mM HEPES-NaOH pH 7.5, 3 mM MgCl2, 3 mM MnCl2, 3 M Na-orthovanadate, 1.2 mM DTT, 50 g/ml PEG20000, 1 µM ATP, [γ-33P]-ATP (approx. 1.8×1006 cpm per well), protein kinase (0.1 nM DNA-PK; 2.4 nM mTOR), and substrate (2 µg/well for DNA-PK and 1 µg/well for mTOR). The DNA-PK assay additionally contained 2.5 µg/ml DNA. The reaction cocktails were incubated at 30° C. for 60 minutes. The reaction was stopped with 50 µl of 2% (v/v) H3PO4, plates were aspirated and washed two times with 200 µl 0.9% (w/v) NaCl. Incorporation of 33Pi was determined with a microplate scintillation counter (Microbeta, Wallac). All assays were performed with a Beckman Coulter/SAGIAN™ Core System.

The compound IC$_{50}$ values for all kinases tested were calculated using Quattro Workflow V3.1.0 (Quattro Research GmbH, Germany).

In order to specify the affinities of Compound 1* towards kinases that showed >50% inhibition in the Kinome Scan, dissociation constants (Kd) for Compound 1* were determined from dose-response curves with the KINOMEscan technology for the class I PI3Ks (α, β, γ and δ), for the class II PI3K PIK3C2B, for the class III PI3K PIK3C3 (Vps34), for the PIKKs (Class IV) mTOR and DNAPK and for the P14 phosphate kinase PIK4B. The smaller the dissociation constant, the higher is the affinity between test compound and kinase. Determination of Kd revealed that Compound 1* was binding with high affinities to the ATP-site of PI3K Class-I family PI3Kα, PI3Kβ, PI3Kγ and PI3Kδ with 0.002 µM, 0.011 µM, 0.025 µM and 0.025 µM, respectively (Table 13, Column 2). Weak binding was observed to Class II PIK3CB (Kd: 0.82 µM), and to the Class III family kinase PIK3C3 (Kd: 0.23 µM). Compound 1* showed high affinity to the Class-IV PIKK mTOR (Kd: 0.012 µM) while binding to the other PIKK-member, DNAPK, was about 130-fold weaker (Kd: 1.6 µM) and no binding was observed to the P14 kinase PIK4B (Kd >40 µM).

In order to investigate its selectivity and interactions across the human kinome, Compound 1* was tested in the KINOMEscan™. Developed by DiscoveRx, KINOMEscan™ employs proprietary active-site dependent competition binding assays allowing the determination of affinities of compounds to the ATP site of protein and lipid kinases. KINOMEscan assays do not require ATP and thereby report true thermodynamic interaction affinities, as opposed to IC50 values, which can depend on the ATP concentration (See more at: htip://www.discoverx.com/technologies-platforms/competitive-binding-technology/kinomescan-technology-platform #sthash.TRzjYTmK.dpuf.

In a primary screen, Compound 1 was tested at a single concentration of 10.0 M against 456 human protein and lipid kinases. In these assays, binding of the test compound to a kinase results in reduction of the signal and the results for the primary screen are reported as % Ctrl (percentage of control), where lower numbers indicate stronger hits (FIG. 1).

TABLE 13

|  | Binding assay |  | Kinase assay |
| --- | --- | --- | --- |
|  | % inh @ 10 µM | Kd (µM) |  |
| PIK3CA | 100 | 0.002 | 0.03 |
| PIK3CA(C420R) | 100 | nd | nd |
| PIK3CA(E542K) | 100 | nd | nd |
| PIK3CA(E545A) | 100 | nd | nd |
| PIK3CA(E545K) | 100 | nd | nd |
| PIK3CA(H1047L) | 86 | nd | nd |
| PIK3CA(H1047Y) | 99 | nd | nd |
| PIK3CA(I800L) | 100 | nd | nd |
| PIK3CA(M1043I) | 87 | nd | nd |
| PIK3CA(Q546K) | 100 | nd | nd |
| PIK3CB | 97 | 0.011 | 0.66 |
| PIK3CG | 99 | 0.025 | 0.71 |
| PIK3CD | 97 | 0.025 | 0.45 |
| PIK3C2B | 59 | 0.82 | nd |
| PIK3C2G | 93 | n.d. | nd |
| PIK3C3 | nd | 0.23 | 8.5 |
| mTOR | 100 | 0.012 | 0.09 |
| DNAPK | nd | 1.6 | 8.6 |
| PIK4B | 5 | >40 | nd |

Binding assays: A11-point 3-fold serial dilution of each test compound was prepared in 100% DMSO at 100× final test concentration and subsequently diluted to 1× in the assay (final DMSO concentration=2.5%) as described by DiscoveRx (Fremont, USA) (Table 13). As shown in Table 13 (Column1), a potent inhibition of binding at 10.0 µM of Compound 1* was observed for the P3K Class-I family (PI3Kα, β, γ and δ), the relevant PI3Kα (PIK3CA) mutants as well as mTOR and to certain degree also Class-II (PIK3CB with a Kd=0.82 µM). Determination of Kd revealed that Compound 1* was binding to the ATP-site of P3K Class-I family PI3Kα, PI3Kβ, PI3Kγ and P3Kδ with 2 nM, 11 nM, 25 nM and 25 nM, respectively. Also potent binding to the ATP site of mTOR (Kd: 12 nM) was observed. Compound 1* inhibits potently the lipid kinase activity of all recombinantly produced PI3K Class-I subtypes including the mutant version of PI3Kα and mTOR with $IC_{50}$ in the nanomolar range [2 to 25 nM] and to certain degree also Class-II (PIK3CB with a Kd=0.82 µM) without affecting significantly other lipid and protein kinase tested in biochemical assays (456 kinases of Kinomescan, DiscoverX).

Kinase assay: We also analyzed Compound 1* for its ability to inhibit kinase function of PIK3CA and related kinases (Proqinase, Germany). Lipid kinases PIK3CA, PIK3CB, PIK3CG, PIK3CD, PIK3C2A, PIK3C2B, PIK3C2G, PIK3C3, PIK4B were tested in an ADP-Glo assay (Promega, USA). Protein kinases mTOR and DNAPK were tested in a radiometric $^{33}$P-γATP assay ($^{33}$PanQinase® Activity Assay, Proqinase, Germany). $IC_{50}$ values were measured by testing 10 semi-log concentrations of each compound in the range from 1×10-04 M to 3×10-09 M, in singlicate.

Example 4

Pig Skin Penetration of the Inventive Compounds

The assessment of percutaneous permeation is key to the successful development of new products and formulations intended for human use. Moreover, it is further important for bioequivalence assessments of locally acting products in the pharmaceutical industry. More commonly used models to conduct skin-permeation studies are ex vivo human or animal skin. Through the standardization of protocols and techniques, the available skin models can be useful as surrogate models for in vivo human skin to evaluate the bioequivalence of topical products. A wide range of animal models has been used as alternatives to human skin to evaluate percutaneous permeation of substances. Since porcine (pig) skin is histologically similar to human skin with a comparable SC thickness of 21-26 m. In addition, the average hair-follicle density in porcine ear skin is 20/cm$^2$ compared to 14-32/cm$^2$ in human forehead skin. As well as being similar to human skin, porcine ear skin is also convenient to obtain and has been widely used in skin-permeation studies. Therefore to mimic human skin penetration the use of pig skin either ex vivo or in vivo is sufficient and predictable.

Ex vivo and in vivo models to assess the penetration of various drug substances including the inventive compounds in the skin of pigs have been established. These pig models allow to assess the PK profile of several drug candidates including the inventive compounds in one subject, thereby enhancing comparability and avoiding inter-subject variability.

Figure 2:
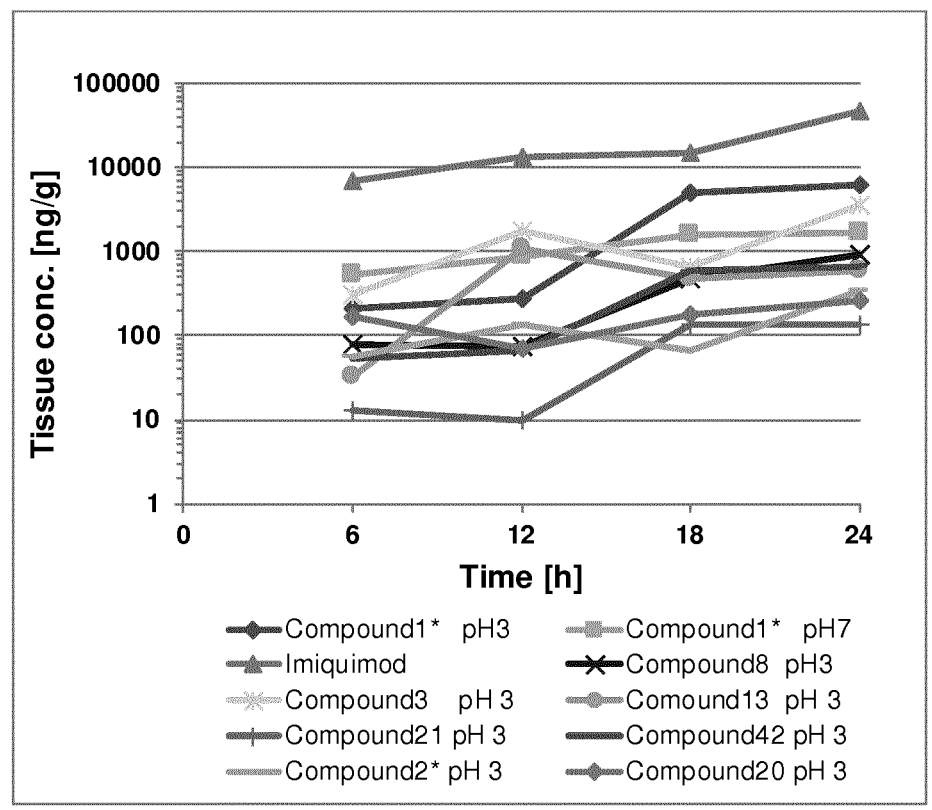
FIG. 2: PK profiles of nine formulations comprising the inventive compounds and control have been assessed. The control formulation Aldara (5% imiquimod) was applied to detect variations in skin permeability (local variability in the same animal and inter-subject variability). The stratum corneum was removed by tape stripping to avoid contamination during the biopsy extraction. From the application sites dosed with the 9 test formulations, 3 replicate biopsies were taken at 6 hours, 12 hours, 18 hours and 24 hours post dose. One biopsy was taken from each control site. Additionally, 5 blank samples were taken.

In the first study (FIG. 2, Table 15) the PK profiles of nine test formulations have been assessed using 80% SBECD either at pH3 or pH 7. 1* and 3 as 1% experimental formulations penetrated into pig skin (lower epidermis and dermis) to a significant extent ex vivo, despite drying up on the skin after a few hours post application. In comparison with Aldara, a cream containing 5% of the TLR7 agonist imiquimod, the intrinsic penetration properties of 1* were estimated to be similar to imiquimod, while those of 3 were slightly lower.

TABLE 15

Nine formulations comprising inventive compounds and one control formulation.

| Compound | Formulation | Nominal conc. [mg/mL] | Applied amount of formulation[1] | Applied amount of compound |
|---|---|---|---|---|
| 1* pH 3 | 1% (base, w/v) | 10.01 | 46 μL | 460.5 μg |
| 1* pH 7 | 1% (base, w/v) | 10.01 | 46 μL | 460.5 μg |
| 8 pH 3 | 0.5% (base, w/v) | 5.03 | 46 μL | 231.4 μg |
| 3 pH 3 | 1% (base, w/v) | 10.03 | 46 μL | 461.4 μg |
| 13 pH 3 | 0.5% (base, w/v) | 5.00 | 46 μL | 230.0 μg |
| 2* pH 3 | 0.2% (base, w/v) | 1.82 | 46 μL | 83.7 μg |
| 21 pH 3 | 0.1% (base, w/v) | 0.74 | 46 μL | 34.0 μg |
| 20 pH 3 | 0.5% (base, w/v) | 4.35 | 46 μL | 200.1 μg |
| 42 pH 3 | 0.5% (base, w/v) | 5.05 | 46 μL | 232.3 μg |
| Imiquimod (Aldara - MEDA AB, Sweden) | 5% cream | — | 56 mg | 2.8 mg |

Figure 3:
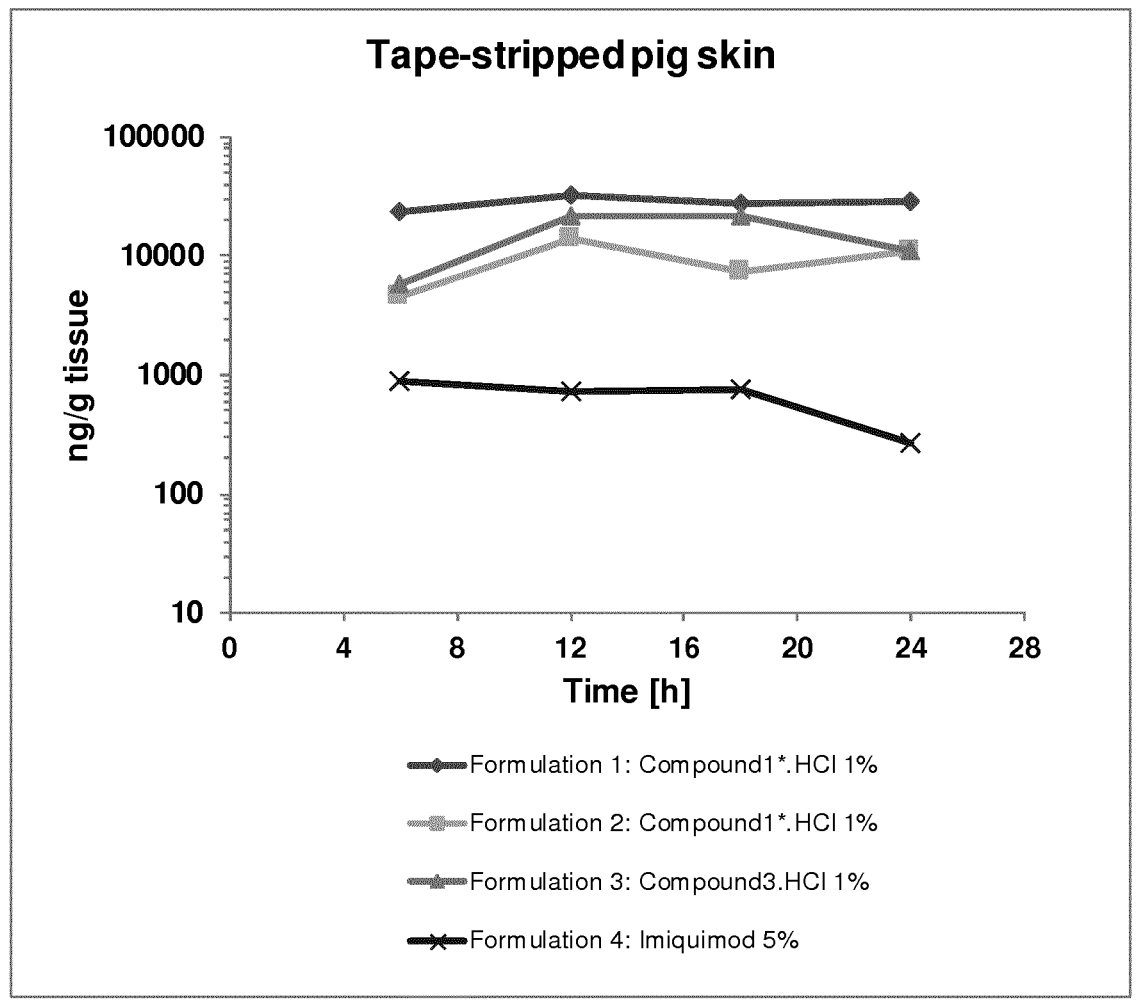
FIG. 3: PK profiles of three formulations comprising the inventive compounds. Excised pig skin was placed in a climate chamber to control temperature and humidity. From every application site (20×40 mm) three replicate biopsies were taken at 6 hours, 12 hours, 18 hours and 24 hours post dose. Before biopsies were taken the stratum corneum was removed by tape stripping and biopsies consisted of the remaining epidermis and entire dermis.

[1]Application area 4 cm × 2 cm = 8 $cm^2$; applied formulation of 5.75 μL/$cm^2$ or 7 mg/$cm^2$ corresponding to 46 μL or 56 mg A further study was performed to investigate the skin PK profile of 4 test formulations in ex vivo pig skin: 1% 1* in a 90% propylene glycol (PG)/10% oleyl alcohol (OA), 1% 1* in a 100% PG formulation, 1% 3 in a 90% PG/10% OA formulation and the control formulation Aldara (containing 5% imiquimod). The PK profiles are presented in Table 16 and in FIG. 3. 1* in a 90% PG and 10% OA formulation showed the highest skin penetration followed by the 3 in 90% PG and 10% OA. The skin concentration of 1* in 100% PG alone was lower compared with the preparation containing 10% OA, but was still much higher than the skin concentration of the control formulation Aldara. The skin PK profile of 3 in 100% PG was comparable to 1*.

TABLE 16

Three formulations comprising inventive compounds and one control formulation.

| Compound | Formulation | Nominal conc. [mg/mL] | Applied amount of formulation[1] | Applied amount of compound |
|---|---|---|---|---|
| 1* | 1% Cpd 1* in 90% PG and 10% OA | 10.0 | 46 μL | 460 μg |
| 1* (100% PG) | 1% Cpd 1* in 100% PG | 10.0 | 46 μL | 460 μg |
| 3 | 1% Cpd 3 in 90% PG and 10% OA | 10.0 | 46 μL | 460 μg |
| Imiquimod (Aldara, MEDA AB, Sweden) | 5% cream | — | 56 mg | 2.8 mg |

[1]Application area 4 cm × 2 cm = 8 $cm^2$; applied formulation of 5.75 μL/$cm^2$ or 7 mg/$cm^2$ corresponding to 46 μL or 56 mg In conclusion, topical treatment of pig skin ex vivo with 1* and 3 in 1% experimental preparations containing the standard solvent propylene glycol resulted in high drug concentrations in the lower epidermis and dermis, which were higher compared to skin concentrations achieved after topical treatment with the standard product Aldara (containing 5% imiquimod).

The aim of a further study is to measure the skin penetration of the same formulations of 1* and 3 in pigs in vivo. The following formulations were tested:
1% 1* in propylene glycol (PG)
1% 1* propylene glycol with thickener (PG+TH)
1% 1* in PEG
Imiquimod as control formulation (Aldara 5% cream)
Brief description of the pig in vivo model:

A 4 month old domestic pig was used for this study. Three days before study start the back and both flanks of the pig were shaved and the pig was anesthetized. The application sites were marked on the skin with a surgical stencil and the test formulations applied. At the end of the study the pig was euthanized, remaining experimental test preparations and control formulation removed from the application sites and the Stratum Corneum removed by tape stripping. From each application site three replicate biopsies were taken 6 hours, 9 hours, and 12 hours post dose. The biopsies were placed in cryotubes, weighed and analysed for compound concentrations.

Figure 4A:
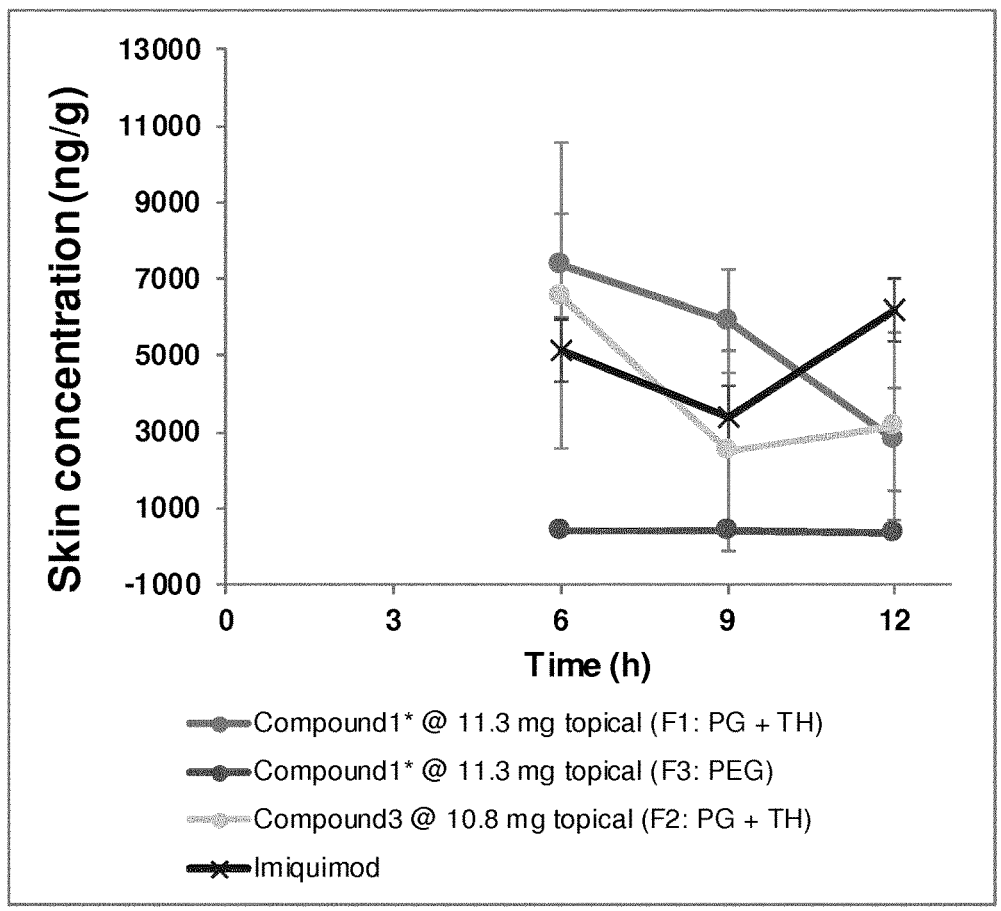
FIG. 4A: PK of 1% 1* in either propylene glycol or polyethylene glycol (PEG). A 30-45 kg domestic pig was anaesthetized for a duration of 12 hours. Each of the four formulations were applied 6 times (2 replicates for each of the three time points—6, 9 and 12 hours) on 24 different application sites At the end of the study the pig was sacrificed and stratum corneum removed by tape stripping.

Except for the PEG formulation high levels of 1* were found after the stratum corneum removed by tape stripping in epidermis and dermis of the living pig (FIG. 4A).

Figure 4B:
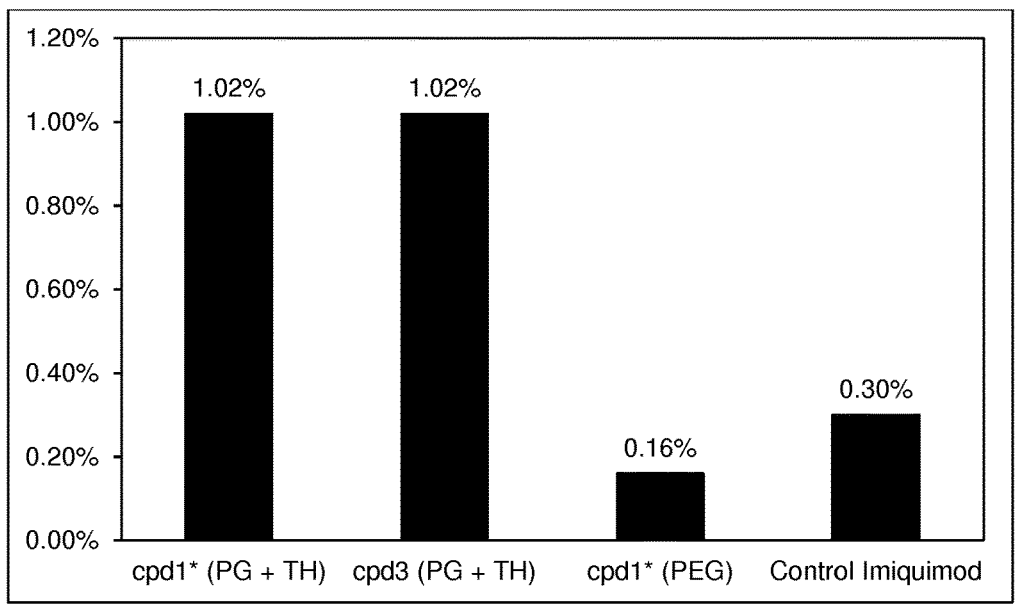
FIG. 4B: Absolute amount of compound in biopsy plotted relative to the amount of compound applied on the biopsy area for 12 hours for compounds 1* (PG+Thickener TH) and 3 (PG+Thickener TH), 1* (PEG) and control imiquimod (Aldara).

In turn, the absolute amount of compound in biopsy plotted relative to the amount of compound applied on the biopsy area for 12 hours for compounds 1* (PG+Thickener TH), 3 (PG+Thickener TH), 1* (PEG) and control imiquimod (Aldara) is shown in FIG. 4B.

In conclusion from this study, significant levels of 1* and 3 were found after the stratum corneum removed by tape stripping in epidermis and dermis of the living pig (FIG. 4B). Thus, both 1* and 3 in an experimental test preparation using a standard solvent like propylene glycol showed significant skin penetration after one single topical application in the in vivo pig model. Considering the absolute amount of drug in the skin vs the topically applied compound, it becomes evident that the PEG formulation 1* (PEG) is only slightly less penetrating than imiquimod in Aldara.

Example 5

In Vivo Pig Skin Penetration Assessment of the Inventive Compounds 1, 2 and 8 in Comparison to Sirolimus (Rapamycin)

Again a further study was performed to compare the skin PK profile of 3 test formulations with Sirolimus (Rapamycin) in in vivo pig skin: 1% 1* in 91.2% propylene glycol (PG)/7.5% Hydroxypropylcellulose M.W. 100'000 (HPC); 0.3% 2 in 91.2% PG/7.5% HPC; 1% 8 in 91.2% PG/7.5% HPC and 1% Sirolimus in 91.2% PG/7.5% HPC.

Figure 5:
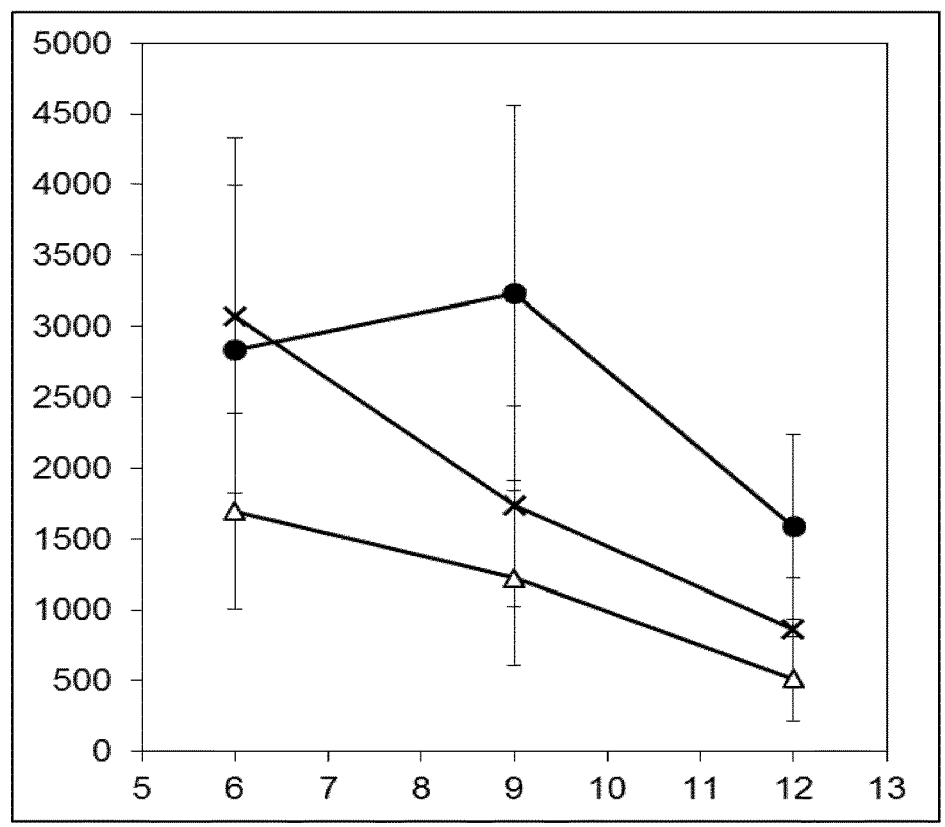
FIG. 5: Comparison of skin PK profiles of test formulations comprising the inventive compounds with Sirolimus in in vivo pig skin: 1% 1* in 91.2% propylene glycol (PG)/7.5% Hydroxypropylcellulose M.W. 100'000 (HPC); 0.3% 2 in 91.2% PG/7.5% HPC; and 1% Sirolimus in 91.2% PG/7.5% HPC. The inventive compounds showed a preferred penetration profile in terms of Cmax and AUC as compared to the reference compound Sirolimus. The skin concentration in ng/g is shown on the y-axis, whereas the x-axis refers to the time in hours. Compound 1* is shown as full black circles (●), compound 2 as crosses (x) and sirolimus as empty triangles (Δ).

The inventive compounds showed a preferred penetration profile in terms of exposure of compounds with respect to their maximal achievable concentration (Cmax) and total exposure as expressed as area under the curve (AUC) as compared to the reference compound Sirolimus (FIG. 5).

Example 6

Comparison Stress Stability of the Inventive Compound 1* and Sirolimus

Figure 6:
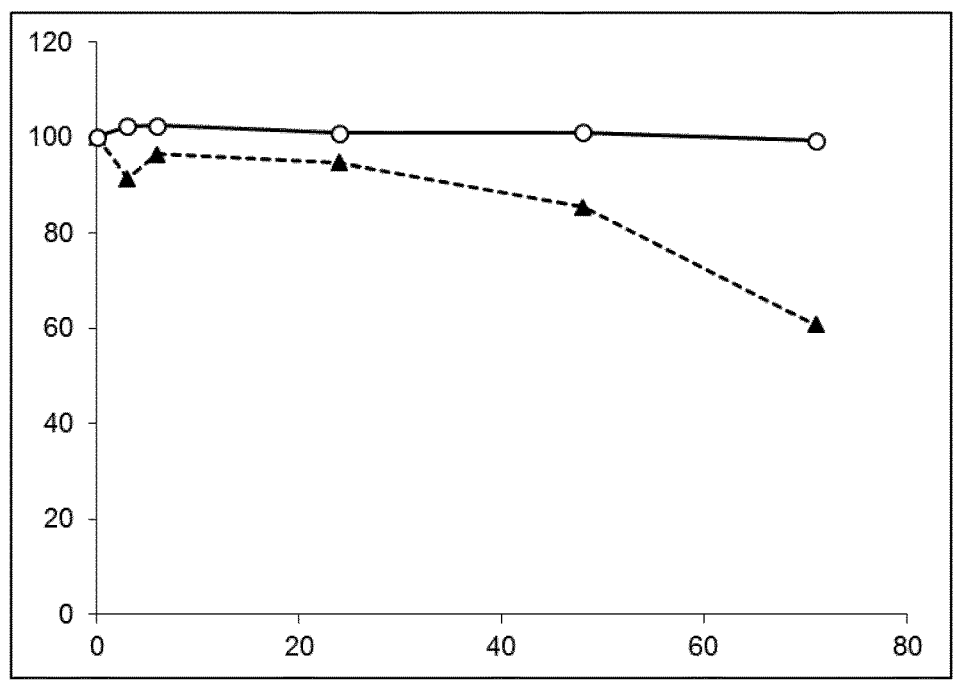
FIG. 6: Chemical stability of 1* in comparison to Sirolimus (Rapamycin) in propyleneglycol under stress conditions (60° C.). The fraction of residual test item was determined by HPLC. The y-axis shows the % area by HLPC. The x-axis shows the time in hours. During the observation period of 72 hrs. Compound 1* (shown as empty circles -o-) was degraded by 1%, whereas Sirolimus (shown as black triangles •••▲••) was degraded by 39%.

A study was performed to assess the chemical stability of 1* in comparison to Sirolimus (Rapamycin) in propyleneglycol under stress conditions (60° C.). Equal concentrations (1%) of the test items in propyleneglycol were heated to 60° C. and the fraction of residual test item was determined by HPLC. During the observation period (72 h) compound 1* was degraded by 1%, whereas Sirolimus was degraded by 39% (FIG. 6). Since chemical stability is a key aspect of a drug applied in a topical formulation, the data provided surprisingly indicate a superior stability property of the inventive compound 1*.

The invention claimed is:
1. A method of treating an angiofibroma in a subject in need thereof, comprising administering to the subject an effective amount of a compound of formula (I),

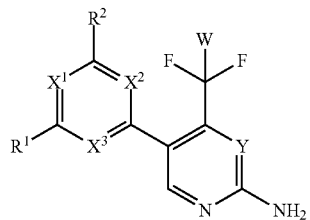

(I)

wherein
$X^1$, $X^2$ and $X^3$ are, independently of each other, N or CH; with the proviso that at least two of $X^1$, $X^2$ and $X^3$ are N;
Y is N or CH;
W is H or F; with the proviso that when W is F, then $X^1$, $X^2$ and $X^3$ are N;
$R^1$ and $R^2$ are independently of each other
  (i) a morpholinyl of formula (II)

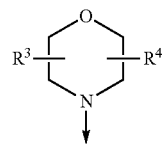

(II)

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy, $C_1$-$C_3$alkyl, CN, or C(O)O-$C_1$-$C_2$alkyl; or $R^3$ and $R^4$ form together a bivalent residue -$R^5R^6$-selected from $C_1$-$C_3$alkylene optionally substituted with 1 to 4 F, —CH$_2$—O—CH$_2$—, —CH$_2$—NH—CH$_2$—, or any of the structures

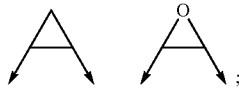

wherein the arrows denote the bonds in formula (II); or
  (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy, $C_1$-$C_3$alkyl, $C_3$-$C_6$cycloalkyl; or two $R^7$ substituents form together a bivalent residue -$R^8R^9$-selected from $C_1$-$C_3$alkylene optionally substituted with 1 to 4 F, —CH$_2$—O—CH$_2$— or —O—CH$_2$CH$_2$—O—;
with the proviso that at least one of $R^1$ and $R^2$ is a morpholinyl of formula II;
or a prodrug, metabolite, tautomer, solvate or pharmaceutically acceptable salt thereof.

2. A method of treating an angiofibroma in a subject in need thereof, comprising administering to the subject an effective amount of a compound of formula (I),

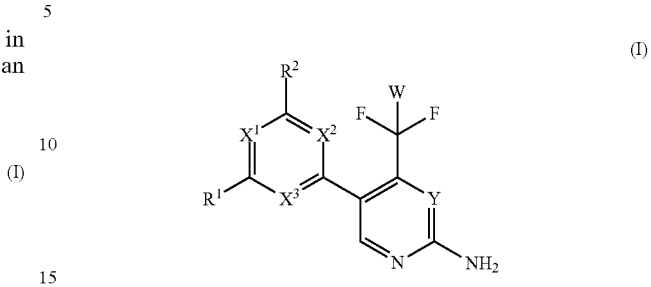

(I)

wherein
$X^1$, $X^2$ and $X^3$ are, independently of each other, N or CH; with the proviso that at least two of $X^1$, $X^2$ and $X^3$ are N;
Y is N or CH;
W is H or F; with the proviso that when W is F, then $X^1$, $X^2$ and $X^3$ are N;
$R^1$ and $R^2$ are independently of each other selected from:

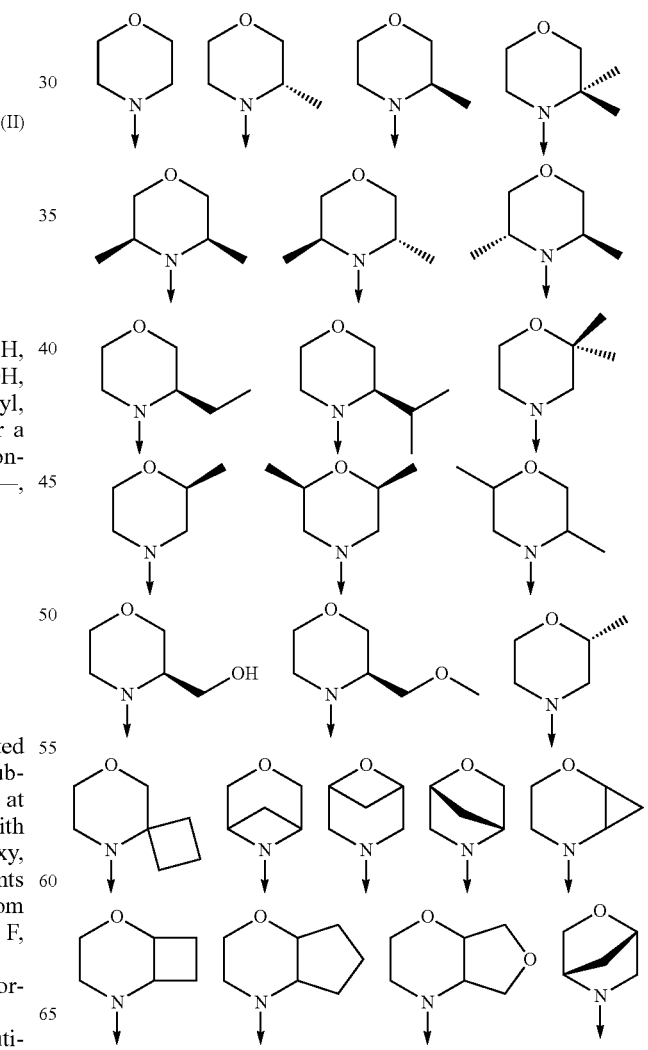

-continued

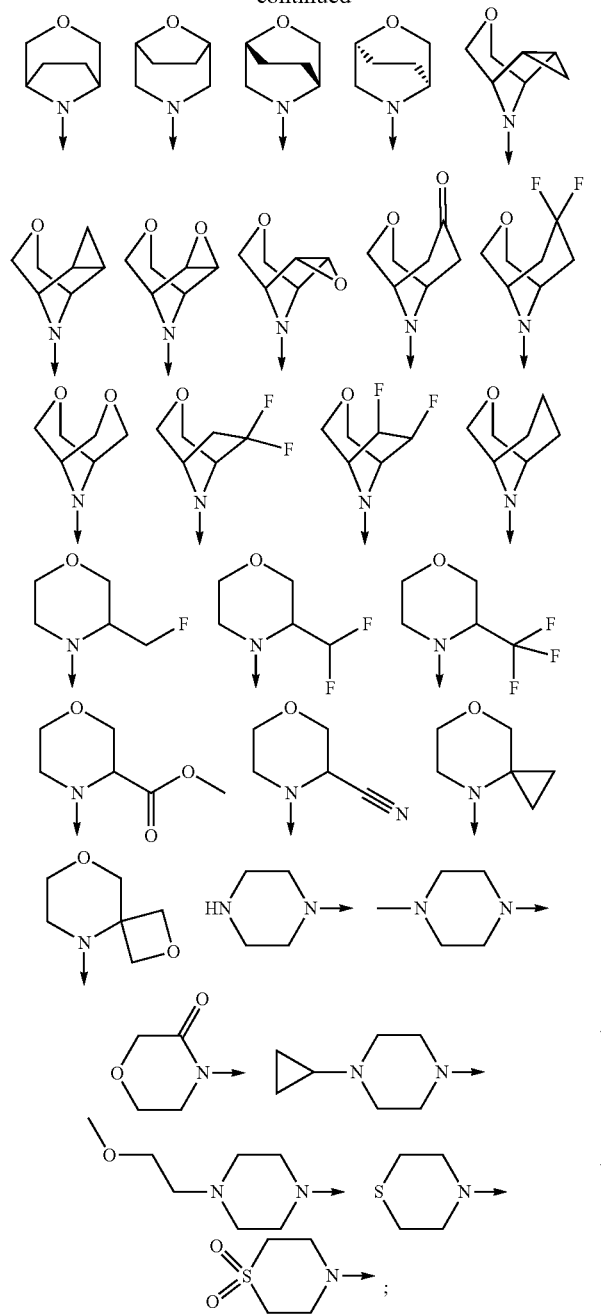

with the proviso that at least one of $R^1$ and $R^2$ is a morpholinyl of formula II

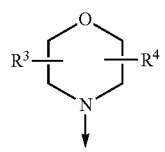
(II)

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy, $C_1$-$C_3$alkyl, CN, or C(O)O—$C_1$-$C_2$alkyl; or $R^3$ and $R^4$ form together a bivalent residue -$R^5R^6$-selected from $C_1$-$C_3$alkylene optionally substituted with 1 to 4 F, —$CH_2$—O—$CH_2$—, —$CH_2$—NH—$CH_2$—, or any of the structures

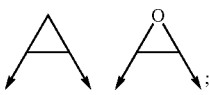

wherein the arrows denote the bonds in formula (II);
or a prodrug, metabolite, tautomer, solvate or pharmaceutically acceptable salt thereof.

3. The method according to claim 1, wherein $R^1$ and $R^2$ are independently of each other selected from

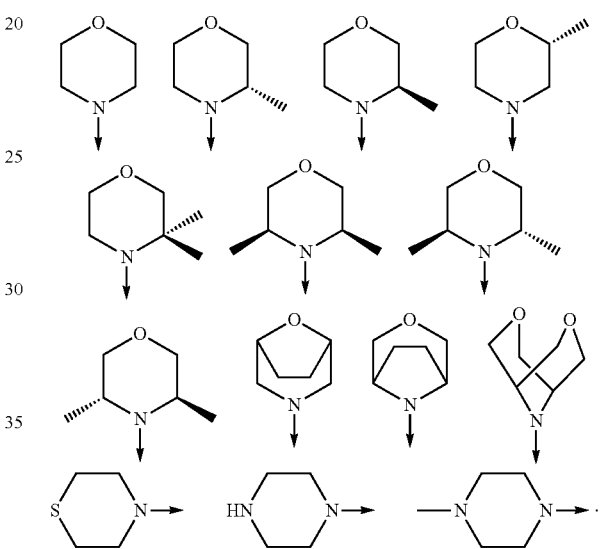

4. The method according to claim 1, wherein said compound is selected from
4-(difluoromethyl)-5-(4,6-dimorpholino-1,3,5-triazin-2-yl)pyridin-2-amine;
5-(4,6-dimorpholino-1,3,5-triazin-2-yl)-4-(trifluoromethyl)pyridin-2-amine;
4-(difluoromethyl)-5-(4,6-dimorpholino-1,3,5-triazin-2-yl)pyrimidin-2-amine;
5-(4,6-dimorpholino-1,3,5-triazin-2-yl)-4-(trifluoromethyl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyrimidin-2-amine;
5-(4,6-bis((S)-3-methylmorpholino)-1,3,5-triazin-2-yl)-4-(difluoromethyl)pyridin-2-amine;
5-[4,6-bis [(3 S)-3-methylmorpholin-4-yl]-1,3,5-triazin-2-yl]-4-(trifluoromethyl)pyridin-2-amine;
5-(4,6-bis((S)-3-methylmorpholino)-1,3,5-triazin-2-yl)-4-(difluoromethyl)pyrimidin-2-amine;

5-[4,6-bis [(3 S)-3-methylmorpholin-4-yl]-1,3,5-triazin-2-yl]-4-(trifluoromethyl)pyrimidin-2-amine;
(S)-4-(difluoromethyl)-5 -(4-(3-methylmorpholino)-6-morpholino- 1, 3, 5-triazin-2-yl)pyridin-2-amine;
5-[4-[(3 S)-3-methylmorpholin-4-yl]-6-morpholino- 1,3, 5-triazin-2-yl]-4-(trifluoromethyl)pyridin-2-amine;
(S)-4-(difluoromethyl)-5 -(4-(3-methylmorpholino)-6-morpholino- 1, 3, 5-triazin-2-yl)pyrimidin-2-amine;
5-[4-[(3 S)-3-methylmorpholin-4-yl]-6-morpholino- 1,3, 5-triazin-2-yl]-4-(trifluoromethyl)pyrimidin-2-amine;
5-(4-(3-oxa-8-azabicyclo[3.2.1] octan-8-yl)-6-((S)-3-methylmorpholino)- 1,3,5-triazin-2-yl)-4-(difluoromethyl)pyridin-2-amine;
5-(4-(3-oxa-8-azabicyclo[3.2.1] octan-8-yl)-6-((S)-3-methylmorpholino)- 1,3,5-triazin-2-yl)-4-(difluoromethyl)pyrimidin-2-amine;
4-(difluoromethyl)-5-(4-morpholino-6-(piperazin- 1-yl)-1,3, 5-triazin-2-yl)pyridin-2-amine;
5-(4-morpholino-6-piperazin-1-yl-1,3,5-triazin-2-yl)-4-(trifluoromethyl)pyridin-2-amine;
4-(difluoromethyl)-5-(4-morpholino-6-(piperazin- 1-yl)-1,3, 5-triazin-2-yl)pyrimidin-2-amine;
5-(4-morpholino-6-piperazin-1-yl-1,3,5-triazin-2-yl)-4-(trifluoromethyl)pyrimidin-2-amine;
(S)-4-(difluoromethyl)-5 -(4-(3-methylmorpholino)-6-(piperazin-1-yl)- 1,3,5 -triazin-2-yl)pyridin-2-amine;
(S)-4-(difluoromethyl)-5 -(4-(3-methylmorpholino)-6-(piperazin-1-yl)- 1,3,5 -triazin-2-yl)pyrimidin-2-amine;
4-(difluoromethyl)-5 -(2, 6-dimorpholinopyrimidin-4-yl) pyridin-2-amine;
4'-(difluoromethyl)-2,6-dimorpholino-[4,5'-bipyrimidin]-2'-amine;
4-(difluoromethyl)-5-(4,6-dimorpholino-pyrimidin-2-yl) pyridin-2-amine;
4'-(difluoromethyl)-4,6-dimorpholino-[2,5'-bipyrimidin]-2'-amine;
4-(difluoromethyl)-5-(4-morpholino-6-thiomorpholino-1,3,5-triazin-2-yl)pyridin-2-amine;
5-(4-morpholino-6-thiomorpholino-1,3,5-triazin-2-yl)-4-(trifluoromethyl)pyridin-2-amine;
4-(difluoromethyl)-5-(4-morpholino-6-thiomorpholino-1,3,5-triazin-2-yl)pyrimidin-2-amine;
5-(4-morpholino-6-thiomorpholino-1,3,5-triazin-2-yl)-4-(trifluoromethyl)pyrimidin-2-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
5-(2,6-bis((S)-3-methylmorpholino)-pyrimidin-4-yl)-4-(difluoromethyl)pyridin-2-amine;
4'-(difluoromethyl)-2,6-bis((S)-3-methylmorpholino)44,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;
5[4,6-bis(2,2-dimethylmorpholin-4-yl)-1,3,5-triazin-2-yl]-4-(difluoromethyl)-pyridin-2-amine;
(S)-4-(difluoromethyl)-5-(2-(3-methylmorpholino)-6-morpholinopyrimidin-4-yl)pyridin-2-amine;
(S)-4'-(difluoromethyl)-2-(3-methylmorpholino)-6-morpholino-[4,5'-bipyrimidin]-2'-amine;
4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine;
5[4,6-bis[(2R,6S)-2,6-dimethylmorpholin-4-yl]-1,3,5-triazin-2-yl]-4-(difluoromethyl)pyridin-2-amine;
5[4,6-bis(3,7-dioxa-9-azabicyclo[3.3.1]nonan-9-yl)-1,3,5-triazin-2-yl]-4-(difluoromethyl)pyridin-2-amine;
4-(difluoromethyl)-5[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;
5[4,6-bis(3,3-dimethylmorpholin-4-yl)-1,3,5-triazin-2-yl]-4-(difluoromethyl)-pyridin-2-amine;
5-[4,6-bis[(3R,5S)-3,5-dimethylmorpholin-4-yl]-1,3,5-triazin-2-yl]-4-(difluoromethyl)pyridin-2-amine;
5[4,6-bis[(3R)-3-methylmorpholin-4-yl]-1,3,5-triazin-2-yl]-4-(difluoromethyl)pyridin-2-amine;
4-(difluoromethyl)-5[4-(3,3-dimethylmorpholin-4-yl)-6-morpholino-1,3,5-triazin-2-yl]pyridin-2-amine;
4-(difluoromethyl)-5[4-[(3R,5S)-3,5-dimethylmorpholin-4-yl]-6-[(3R)-3-methylmorpholin-4-yl]-1,3,5-triazin-2-yl]pyridin-2-amine;
4-(difluoromethyl)-5[4-(3,3-dimethylmorpholin-4-yl)-6-[(3R)-3-methylmorpholin-4-yl]-1,3,5-triazin-2-yl]pyridin-2-amine;
4-(difluoromethyl)-5[4-[(3R)-3-(methoxymethyl)morpholin-4-yl]-6-[(3R)-3-methylmorpholin-4-yl]-1,3,5-triazin-2-yl]pyridin-2-amine;
4-(difluoromethyl)-5[4-(3,7-dioxa-9-azabicyclo[3.3.1]nonan-9-yl)-6-[(3R)-3-methylmorpholin-4-yl]-1,3,5-triazin-2-yl]pyridin-2-amine;
4-(difluoromethyl)-5[4-[(3R)-3-methylmorpholin-4-yl]-6-(3-oxa-6-azabicyclo[3.1.1]heptan-6-yl)-1,3,5-triazin-2-yl]pyridin-2-amine;
4-(difluoromethyl)-5[4-[(3R)-3-methylmorpholin-4-yl]-6-(6-oxa-3-azabicyclo[3.1.1]heptan-3-yl)-1,3,5-triazin-2-yl]pyridin-2-amine;
4-(difluoromethyl)-5[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine;
4-(difluoromethyl)-5[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine;
5[4,6-bis[(3R)-3-ethylmorpholin-4-yl]-1,3,5-triazin-2-yl]-4-(difluoromethyl)pyridin-2-amine;
5[4,6-bis(8-oxa-5-azaspiro[3.5]nonan-5-yl)-1,3,5-triazin-2-yl]-4-(difluoromethyl)pyridin-2-amine;
5-[4,6-bis[(3R)-3-isopropylmorpholin-4-yl]-1,3,5-triazin-2-yl]-4-(difluoromethyl)pyridin-2-amine;
4-(difluoromethyl)-5[4-(3,3-dimethylmorpholin-4-yl)-6-[(3R,5S)-3,5-dimethylmorpholin-4-yl]-1,3,5-triazin-2-yl]pyridin-2-amine;
4-(difluoromethyl)-5[4-(3,3-dimethylmorpholin-4-yl)-6-[(3R)-3-(methoxymethyl)morpholin-4-yl]-1,3,5-triazin-2-yl]pyridin-2-amine;
](3R)-4[4-[6-amino-4-(difluoromethyl)-3-pyridyl]-6-(3,3-dimethylmorpholin-4-yl)-1,3,5-triazin-2-yl]morpholin-3-yl]methanol;
4-(difluoromethyl)-5[4-(3,3-dimethylmorpholin-4-yl)-6-(3,7-dioxa-9-azabicyclo[3.3.1]nonan-9-yl)-1,3,5-triazin-2-yl]pyridin-2-amine;
5[4-(4-cyclopropylpiperazin-1-yl)-6-(3,3-dimethylmorpholin-4-yl)-1,3,5-triazin-2-yl]-4-(difluoromethyl)pyridin-2-amine;

4-(difluoromethyl)-5[4-(3,3-dimethylmorpholin-4-yl)-6 [4-(2-methoxyethyl)piperazin-1-yl]-1,3,5-triazin-2-yl] pyridin-2-amine;

[3R)-4-[4-[6-amino-4-(difluoromethyl)-3-pyridyl]-6-[(3R)-3-methylmorpholin-4-yl]-1,3,5-triazin-2-yl]morpholin-3-yl]methanol;

4-(difluoromethyl)-5[4-[(3R,5R)-3,5-dimethylmorpholin-4-yl]-6-[(3R)-3-methylmorpholin-4-yl]-1,3,5-triazin-2-yl]pyridin-2-amine;

4-(difluoromethyl)-5[4-[(3S,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-morpholino-6-(3-oxa-9-azabicyclo[3.3.1]nonan-9-yl)-1,3,5-triazin-2-yl]pyridin-2-amine;

4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;5-[4,6-bis[(3S,5S)-3,5-dimethylmorpholin-4-yl]-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-morpholino- 1,3,5-triazin-2-yl]pyridin-2-amine;

4-(difluoromethyl)-5-[4-[(3 S)-3-ethylmorpholin-4-yl]-6-[(3R)-3-methylmorpholin-4-yl]-1,3,5-triazin-2-yl]pyridin-2-amine;

4-(difluoromethyl)-5[4-[(3R)-3-ethylmorpholin-4-yl]-6-[(3R)-3-methylmorpholin-4-yl]-1,3,5-triazin-2-yl]pyridin-2-amine; and 4-(difluoromethyl)-5[4-[(3R)-3-methylmorpholin-4-yl]-6-(8-oxa-5-azaspiro[3.5]nonan-5-yl)- 1,3,5-triazin-2-yl]pyridin-2-amine;

or tautomer, solvate or pharmaceutically acceptable salt thereof.

5. The method according to claim 1, wherein said compound is selected from 4-(difluoromethyl)-5-(4,6-dimorpholino-1,3,5-triazin-2-yl)pyridin-2-amine;

5-(4,6-dimorpholino-1,3,5-triazin-2-yl)-4-(trifluoromethyl)pyridin-2-amine;

4-(difluoromethyl)-5-(4,6-dimorpholino-1,3,5-triazin-2-yl)pyrimidin-2-amine;

5-(4,6-dimorpholino-1,3,5-triazin-2-yl)-4-(trifluoromethyl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5 -[4,6-bis [(3 S)-3-methylmorpholin-4-yl]-1,3,5-triazin-2-yl]-4-(trifluoromethyl)pyridin-2-amine;

5-(4,6-bis((S)-3-methylmorpholino)-1,3,5-triazin-2-yl)-4-(difluoromethyl)pyrimidin-2-amine;

5-[4,6-bis[(3S)-3-methylmorpholin-4-yl]-1,3,5-triazin-2-yl]-4-(trifluoromethyl)pyrimidin-2-amine;

(S)-4-(difluoromethyl)-5-(4-(3-methylmorpholino)-6-morpholino-1,3,5-triazin-2-yl)pyridin-2-amine;

5-[4-[(3S)-3-methylmorpholin-4-yl]-6-morpholino-1,3,5-triazin-2-yl]-4-(trifluoromethyl)pyridin-2-amine;

(S)-4-(difluoromethyl)-5-(4-(3-methylmorpholino)-6-morpholino-1,3,5-triazin-2-yl)pyrimidin-2-amine;

5-[4-[(3S)-3-methylmorpholin-4-yl]-6-morpholino-1,3,5-triazin-2-yl]-4-(trifluoromethyl)pyrimidin-2-amine;

5-(4-morpholino-6-piperazin-1-yl-1,3,5-triazin-2-yl)-4-(trifluoromethyl)pyridin-2-amine;

4-(difluoromethyl)-5-(4-morpholino-6-(piperazin- 1-yl)-1,3, 5-triazin-2-yl)pyrimidin-2-amine;

5-(4-morpholino-6-piperazin-1-yl-1,3,5-triazin-2-yl)-4-(trifluoromethyl)pyrimidin-2-amine;

5-(4-morpholino-6-thiomorpholino-1,3,5-triazin-2-yl)-4-(trifluoromethyl)pyridin-2-amine;

5-(4-morpholino-6-thiomorpholino-1,3,5-triazin-2-yl)-4-(trifluoromethyl)pyrimidin-2-amine;

5[4,6-bis(3,7-dioxa-9-azabicyclo[3.3.1]nonan-9-yl)-1,3, 5-triazin-2-yl]-4-(difluoromethyl)pyridin-2-amine;

4-(difluoromethyl)-5[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;

5[4,6-bis(3,3-dimethylmorpholin-4-yl)-1,3,5-triazin-2-yl]-4-(difluoromethyl)-pyridin-2-amine;

5-[4,6-bis[(3R,5S)-3,5-dimethylmorpholin-4-yl]-1,3,5-triazin-2-yl]-4-(difluoromethyl)pyridin-2-amine;

5[4,6-bis[(3R)-3-methylmorpholin-4-yl]-1,3,5-triazin-2-yl]-4-(difluoromethyl)pyridin-2-amine;

4-(difluoromethyl)-5[4-(3,3-dimethylmorpholin-4-yl)-6-morpholino-1,3,5-triazin-2-yl]pyridin-2-amine;

4-(difluoromethyl)-5[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5[4-(3,3-dimethylmorpholin-4-yl)-6-[(3R)-3-methylmorpholin-4-yl]-1,3,5-triazin-2-yl]pyridin-2-amine;

4-(difluoromethyl)-5[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5[4-(3,7-dioxa-9-azabicyclo[3.3.1]nonan-9-yl)-6-[(3R)-3-methylmorpholin-4-yl]-1,3,5-triazin-2-yl]pyridin-2-amine;

4-(difluoromethyl)-5[4-(3,7-dioxa-9-azabicyclo[3.3.1]nonan-9-yl)-6-(3-oxa-9-azabicyclo[3.3.1]nonan-9-yl)-1,3, 5-triazin-2-yl]pyridin-2-amine, 5 -[4,6-bis[(3 S,5 S)-3,5-dimethylmorpholin-4-yl]-1,3,5-triazin-2-yl]-4-(difluoromethyl)pyridin-2-amine;

4-(difluoromethyl)-5[4-(3,7-dioxa-9-azabicyclo[3.3.1]nonan-9-yl)-6-morpholino-1,3,5-triazin-2-yl]pyridin-2-amine;

4-(difluoromethyl)-5-[4-[(3 S)-3-ethylmorpholin-4-yl]-6-[(3R)-3-methylmorpholin-4-yl]-1,3,5-triazin-2-yl]pyridin-2-amine;

4-(difluoromethyl)-5[4-[(3R)-3-ethylmorpholin-4-yl]-6-[(3R)-3-methylmorpholin-4-yl]-1,3,5-triazin-2-yl]pyridin-2-amine; and 4-(difluoromethyl)-5[4-[(3R)-3-methylmorpholin-4-yl]-6-(8-oxa-5-azaspiro[3.5]nonan-5-yl)- 1,3, 5-triazin-2-yl]pyridin-2-amine;

or a tautomer, solvate or pharmaceutically acceptable salt thereof.

6. The method according to claim 1, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine 3; (S)-4-(difluoromethyl)-5-(4-(3-methylmorpholino)-6-morpholino-1,3,5-triazin-2-yl)pyridin-2-amine 8; 4-(difluoromethyl)-5[4-[(3R,5S)-3,5-dimethylmorpholin-4-yl]-6-[(3R)-3-methylmorpholin-4-yl]-1,3,5-triazin-2-yl]pyridin-2-amine 44; and 5-(4,6-dimorpholino-1,3,5-triazin-2-yl)-4-(trifluoromethyl)pyridin-2-amine 1*; or a tautomer, solvate, or pharmaceutically acceptable salt thereof.

7. The method according to claim 1, wherein $R^1$ and $R^2$ are independently of each other a morpholinyl of formula (II).

8. The method according to claim 7, wherein $R^1$ is equal to $R^2$.

9. The method according to claim 7, wherein $R^1$ is not equal to $R^2$.

10. The method according to claim 1, wherein W is H.

11. The method according to claim 1, wherein said angiofibroma is a facial angiofibroma.

12. The method according to claim 1, wherein said method is a method of topically treating said angiofibroma in said subject.

13. The method according to claim 2, wherein said angiofibroma is a facial angiofibroma.

14. The method according to claim 2, wherein said method is a method of topically treating said angiofibroma in said subject.

15. The method according to claim 1, comprising administering to said subject an effective amount of a compound of formula (I) or a tautomer, solvate or pharmaceutically acceptable salt thereof.

16. The method according to claim 2, comprising administering to said subject an effective amount of a compound of formula (I) or a tautomer, solvate or pharmaceutically acceptable salt thereof.

17. The method according to claim 15, wherein said compound is 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; or a tautomer, solvate, or pharmaceutically acceptable salt thereof.

18. The method according to claim 15, wherein said compound is (S)-4-(difluoromethyl)-5-(4-(3-methylmorpholino)-6-morpholino-1,3,5-triazin-2-yl)pyridin-2-amine; or a tautomer, solvate, or pharmaceutically acceptable salt thereof.

19. The method according to claim 15, wherein said compound is 4-(difluoromethyl)-5[4-[(3R,5S)-3,5-dimethylmorpholin-4-yl]-6-[(3R)-3-methylmorpholin-4-yl]-1,3,5-triazin-2-yl]pyridin-2-amine; or a tautomer, solvate, or pharmaceutically acceptable salt thereof.

20. The method according to claim 15, wherein said compound is and 5-(4,6-dimorpholino-1,3,5-triazin-2-yl)-4-(trifluoromethyl)pyridin-2-amine; or a tautomer, solvate, or pharmaceutically acceptable salt thereof.

* * * * *

UNITED STATES PATENT AND TRADEMARK OFFICE
CERTIFICATE OF CORRECTION

PATENT NO. : 11,414,426 B2　　　　　　　　　　　　　　　　　　　　Page 1 of 1
APPLICATION NO. : 16/765077
DATED : August 16, 2022
INVENTOR(S) : Doriano Fabbro, Petra Hillmann-Wüllner and Anton Stütz It is certified that error appears in the above-identified patent and that said Letters Patent is hereby corrected as shown below:

In the Claims

Claim 1, Column 147, Line 42: replace "C1-C2fluoroalkyl, C1-C2alkoxy, C1-C2alkoxy, C1-C3alkyl," with -- C1-C2fluoroalkyl, C1-C2alkoxy, C1-C3alkyl --

Claim 2, Column 150, Line 1: replace "C1-C2fluoroalkyl, C1-C2alkoxy, C1-C2alkoxy, C1-C3alkyl," with -- C1-C2fluoroalkyl, C1-C2alkoxy, C1-C3alkyl --

Claim 4, Column 151, Lines 57-58: replace "4'-(difluoromethyl)-2,6-bis((S)-3-methylmorpholino)44, 5'-bipyrimidin]-2'-amine;" with -- 4'-(difluoromethyl)-2,6-bis((S)-3-methylmorpholino)-[4,5'-bipyrimidin]-2'-amine; --

Claim 4, Column 152, Lines 59-61: replace "] (3R)-4[ 4-[ 6-amino-4-(difluoromethyl)-3-pyridyl]-6-(3, 3-dimethylmorpholin-4-yl)-1,3,5-triazin-2-yl]morpholin-3-yl]methanol;" with -- [(3R)-4 [ 4-[ 6-amino-4-(difluoromethyl)-3-pyridyl]-6-(3, 3-dimethylmorpholin-4-yl)-1,3,5-triazin-2-yl]morpholin-3-yl] methanol; --

Claim 4, Column 153, Lines 4-6: replace"[3R)-[4-[6-amino-4-(difluoromethyl)-3-pyridyl]-6-[(3R)-3-methylmorpholin-4-yl]-1,3,5-triazin-2-yl] morpholin-3-yl]methanol;" with -- [(3R)-4-[4-[6-amino-4-(difluoromethyl)-3-pyridyl]-6-[(3R)-3-methylmorpholin-4-yl]-1,3,5-triazin-2-yl] morpholin-3-yl]methanol; --

Claim 5, Column 154, Lines 35-39: replace "4-(difluoromethyl)-5 [ 4-(3, 7-dioxa-9-azabicyclo[3.3.1]nonan-9-yl)-6-(3-oxa-9-azabicyclo[3.3.1 ]nonan-9-y 1)-1,3, 5-triazin-2-yl]pyridin-2-amine, 5 -[ 4,6-bis[(3S,5S)-3,5-dimethylmorpholin-4-yl]-1,3,5-triazin-2-yl]-4-(difluoromethyl) pyridin-2-amine;" with -- 4-(difluoromethyl)-5 [ 4-(3, 7-dioxa-9-azabicyclo[3.3.1]nonan-9-y 1)-6-(3-oxa-9-azabicyclo[3.3.1 ]nonan-9-y1)-1,3,5-triazin-2-yl]pyridin-2-amine; 5-[4,6-bis[(3S,5S)-3,5-dimethylmorpholin-4-yl]-1,3,5-triazin-2-yl]-4-(difluoromethyl)pyridin-2-amine; --

Signed and Sealed this
Fifteenth Day of November, 2022

Katherine Kelly Vidal
*Director of the United States Patent and Trademark Office*